(12) United States Patent
Holsing et al.

(10) Patent No.: US 10,977,789 B2
(45) Date of Patent: Apr. 13, 2021

(54) SYSTEMS, METHODS AND DEVICES FOR FORMING RESPIRATORY-GATED POINT CLOUD FOR FOUR DIMENSIONAL SOFT TISSUE NAVIGATION

(71) Applicant: Veran Medical Technologies, Inc., St. Louis, MO (US)

(72) Inventors: Troy L. Holsing, Golden, CO (US); Mark Hunter, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 196 days.

(21) Appl. No.: 16/194,782

(22) Filed: Nov. 19, 2018

(65) Prior Publication Data

US 2019/0213735 A1    Jul. 11, 2019

Related U.S. Application Data

(63) Continuation of application No. 15/287,648, filed on Oct. 6, 2016, now Pat. No. 10,140,704, which is a
(Continued)

(51) Int. Cl.
*G06T 7/00* (2017.01)
*G06T 19/00* (2011.01)
(Continued)

(52) U.S. Cl.
CPC ............ *G06T 7/0012* (2013.01); *A61B 5/061* (2013.01); *A61B 5/062* (2013.01); *A61B 5/11* (2013.01);
(Continued)

(58) Field of Classification Search
CPC ... A61B 19/5244; A61B 5/061; A61B 5/0066; A61B 17/3478; A61B 17/32002;
(Continued)

(56) References Cited

U.S. PATENT DOCUMENTS 3,788,324 A    1/1974 Lim
4,421,106 A    12/1983 Uehara
(Continued)

FOREIGN PATENT DOCUMENTS

DE    19751761 A1    10/1998
DE    19725137 A1    1/1999
(Continued)

OTHER PUBLICATIONS

European Patent Office, Extended Search Report issued for EP 11818898.6, 6 pages dated Dec. 20, 2013.
(Continued)

*Primary Examiner* — Manav Seth
(74) *Attorney, Agent, or Firm* — Forsgren Fisher et al.; James M. Urzedowski; Daniel A. Tysver

(57) ABSTRACT

A surgical instrument navigation system is provided that visually simulates a virtual volumetric scene of a body cavity of a patient from a point of view of a surgical instrument residing in the cavity of the patient, wherein the surgical instrument, as provided, may be a steerable surgical catheter with a biopsy device and/or a surgical catheter with a side-exiting medical instrument, among others. Additionally, systems, methods and devices are provided for forming a respiratory-gated point cloud of a patient's respiratory system and for placing a localization element in an organ of a patient.

14 Claims, 52 Drawing Sheets

Related U.S. Application Data continuation of application No. 14/843,365, filed on Sep. 2, 2015, now abandoned, which is a continuation of application No. 13/773,984, filed on Feb. 22, 2013, now Pat. No. 9,138,165.

(60) Provisional application No. 61/602,007, filed on Feb. 22, 2012.

(51) Int. Cl.

| | | |
|---|---|---|
| *A61B 34/20* | (2016.01) | |
| *A61B 5/06* | (2006.01) | |
| *A61B 6/12* | (2006.01) | |
| *A61B 8/08* | (2006.01) | |
| *A61B 5/00* | (2006.01) | |
| *A61B 5/11* | (2006.01) | |
| *G06T 1/00* | (2006.01) | |
| *A61B 17/00* | (2006.01) | |
| *A61B 17/29* | (2006.01) | |
| *G06T 7/11* | (2017.01) | |
| *G06T 7/149* | (2017.01) | |
| *A61B 18/00* | (2006.01) | |
| *A61B 6/00* | (2006.01) | |
| *A61B 90/00* | (2016.01) | |
| *A61B 17/3207* | (2006.01) | |
| *A61B 5/113* | (2006.01) | |
| *A61M 25/01* | (2006.01) | |
| *A61B 5/318* | (2021.01) | |
| *A61B 5/01* | (2006.01) | |
| *A61B 17/32* | (2006.01) | |
| *A61B 17/34* | (2006.01) | |
| *A61B 18/02* | (2006.01) | |
| *A61B 18/14* | (2006.01) | |
| *A61B 18/18* | (2006.01) | |
| *A61B 18/24* | (2006.01) | |
| *A61N 5/10* | (2006.01) | |
| *A61B 10/06* | (2006.01) | |
| *G06K 9/46* | (2006.01) | |
| *G06T 11/60* | (2006.01) | |
| *A61B 6/03* | (2006.01) | |

(52) U.S. Cl.
CPC .............. *A61B 5/7285* (2013.01); *A61B 6/12* (2013.01); *A61B 8/0841* (2013.01); *A61B 34/20* (2016.02); *G06T 1/00* (2013.01); *G06T 19/00* (2013.01); *A61B 5/0066* (2013.01); *A61B 5/01* (2013.01); *A61B 5/113* (2013.01); *A61B 5/318* (2021.01); *A61B 5/6852* (2013.01); *A61B 5/725* (2013.01); *A61B 5/7264* (2013.01); *A61B 5/7292* (2013.01); *A61B 5/742* (2013.01); *A61B 6/032* (2013.01); *A61B 6/485* (2013.01); *A61B 6/487* (2013.01); *A61B 6/5223* (2013.01); *A61B 8/483* (2013.01); *A61B 10/06* (2013.01); *A61B 17/29* (2013.01); *A61B 17/32002* (2013.01); *A61B 17/3478* (2013.01); *A61B 18/02* (2013.01); *A61B 18/1492* (2013.01); *A61B 18/1815* (2013.01); *A61B 18/24* (2013.01); *A61B 2017/003* (2013.01); *A61B 2017/00314* (2013.01); *A61B 2017/00323* (2013.01); *A61B 2017/00398* (2013.01); *A61B 2017/00685* (2013.01); *A61B 2017/00694* (2013.01); *A61B 2017/00809* (2013.01); *A61B 2017/2927* (2013.01); *A61B 2017/320775* (2013.01); *A61B 2018/00541* (2013.01); *A61B 2034/2051* (2016.02); *A61B 2034/2072* (2016.02); *A61B 2090/061* (2016.02); *A61B 2090/3925* (2016.02); *A61B 2090/3966* (2016.02); *A61M 25/0108* (2013.01); *A61N 5/1007* (2013.01); *G06K 9/46* (2013.01); *G06K 2009/4666* (2013.01); *G06T 7/11* (2017.01); *G06T 7/149* (2017.01); *G06T 11/60* (2013.01); *G06T 2200/28* (2013.01); *G06T 2207/10028* (2013.01); *G06T 2207/10088* (2013.01); *G06T 2207/10121* (2013.01); *G06T 2207/10132* (2013.01); *G06T 2207/20124* (2013.01); *G06T 2207/30061* (2013.01); *G06T 2210/41* (2013.01); *G06T 2210/56* (2013.01)

(58) Field of Classification Search
CPC .. A61B 7/29; A61B 10/04; A61B 8/12; A61B 8/0841; A61B 6/485; A61B 6/12; A61B 5/489; A61B 5/11; A61B 5/062; A61B 5/05; A61B 5/0402; A61B 5/03; A61B 10/0283; A61B 5/0084; A61B 10/06; A61B 5/7292; A61B 5/113; A61B 17/32053; A61B 2010/0216; A61B 2017/003; A61B 2017/00685; A61B 2017/00694; A61B 2017/00809; A61B 2017/320775; A61B 2019/461; A61B 2019/5272; A61B 2019/5425; A61B 2019/5466; A61B 18/1815; A61B 18/1492; A61B 18/02; A61B 5/6852; A61B 18/24; A61B 2018/00541; A61B 34/20; A61B 5/725; A61B 5/7264; A61B 5/7285; A61B 5/742; A61B 6/032; A61B 6/487; A61B 17/29; A61B 2034/2051; A61B 2034/2072; A61B 2090/061; A61B 2090/3925; A61B 2090/3966; A61B 5/01; A61B 6/5223; A61B 8/483; A61B 2017/00314; A61B 2017/00323; A61B 2017/00398; A61B 2017/2927; G06T 1/00; G06T 7/0083; G06T 7/0089; G06T 19/00; G06T 2207/20124; G06T 2210/41; G06T 2210/56; G06T 7/0012; G06T 7/12; G06T 7/11; G06T 7/149; G06T 7/33; G06T 11/60; G06T 2200/28; G06T 2207/10028; G06T 2207/10121; G06T 2207/10132; G06T 2207/30061; A61N 5/1007; A61M 25/01; A61M 25/0108; G06K 9/46; G06K 9/6201; G06K 9/6267; G06K 2009/4666; A61L 35/11

See application file for complete search history.

(56) References Cited

U.S. PATENT DOCUMENTS

| | | |
|---|---|---|
| 4,583,538 A | 4/1986 | Onik et al. |
| 5,053,042 A | 10/1991 | Bidwell |
| 5,081,997 A | 1/1992 | Bosley, Jr. et al. |
| 5,103,488 A | 4/1992 | Gemello et al. |
| 5,158,088 A | 10/1992 | Nelson et al. |
| 5,186,174 A | 2/1993 | Schlondorff et al. |
| 5,238,804 A | 8/1993 | Maskasky et al. |
| 5,251,165 A | 10/1993 | James, III |
| 5,251,635 A | 10/1993 | Dumoulin et al. |
| 5,265,610 A | 11/1993 | Darrow et al. |
| 5,295,493 A | 3/1994 | Radisch, Jr. |
| 5,348,011 A | 9/1994 | NessAiver |
| 5,359,513 A | 10/1994 | Kano et al. |
| 5,377,678 A | 1/1995 | Dumoulin et al. |
| 5,391,199 A | 2/1995 | Ben-Haim |
| 5,437,292 A | 8/1995 | Kipshidze et al. |
| 5,483,691 A | 1/1996 | Heck et al. |
| 5,483,961 A | 1/1996 | Kelly et al. |

(56) References Cited

U.S. PATENT DOCUMENTS

| | | |
|---|---|---|
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,674,498 A | 10/1997 | Inoue et al. |
| 5,718,241 A | 2/1998 | Ben-Haim et al. |
| 5,730,129 A | 3/1998 | Darrow et al. |
| 5,740,080 A | 4/1998 | Shook et al. |
| 5,740,808 A | 4/1998 | Panescu et al. |
| 5,765,561 A | 6/1998 | Chen et al. |
| 5,769,789 A | 6/1998 | Wang et al. |
| 5,769,861 A | 6/1998 | Vilsmeier |
| 5,771,306 A | 6/1998 | Stork et al. |
| 5,787,886 A | 8/1998 | Kelly et al. |
| 5,803,089 A | 9/1998 | Ferre et al. |
| 5,814,022 A | 9/1998 | Antanavich et al. |
| 5,814,066 A | 9/1998 | Spotnitz |
| 5,833,608 A | 11/1998 | Acker |
| 5,840,025 A | 11/1998 | Ben-Haim |
| 5,868,673 A | 2/1999 | Vesely |
| 5,928,248 A | 7/1999 | Acker |
| 5,951,461 A | 9/1999 | Nyo et al. |
| 5,978,696 A | 11/1999 | VomLehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa, Jr. et al. |
| 6,122,541 A | 9/2000 | Cosman et al. |
| 6,129,508 A | 10/2000 | Bahr et al. |
| 6,132,396 A | 10/2000 | Antanavich et al. |
| 6,139,508 A | 10/2000 | Simpson et al. |
| 6,144,875 A | 11/2000 | Schweikard et al. |
| 6,167,296 A | 12/2000 | Shahidi |
| 6,173,201 B1 | 1/2001 | Front |
| 6,188,355 B1 | 2/2001 | Gilboa |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin et al. |
| 6,246,898 B1 | 6/2001 | Vesely et al. |
| 6,253,770 B1 | 7/2001 | Acker et al. |
| 6,254,550 B1 | 7/2001 | McNamara et al. |
| 6,267,769 B1 | 7/2001 | Truwit |
| 6,275,560 B1 | 8/2001 | Blake et al. |
| 6,282,442 B1 | 8/2001 | DeStefano et al. |
| 6,285,902 B1 | 9/2001 | Kienzle, III et al. |
| 6,298,259 B1 | 10/2001 | Kucharczyk et al. |
| 6,314,310 B1 | 11/2001 | Ben-Haim et al. |
| 6,314,311 B1 | 11/2001 | Williams et al. |
| 6,314,312 B1 | 11/2001 | Wessels et al. |
| 6,317,616 B1 | 11/2001 | Glossop |
| 6,317,619 B1 | 11/2001 | Boemert et al. |
| 6,330,356 B1 | 12/2001 | Sundareswaran et al. |
| 6,332,089 B1 | 12/2001 | Acker et al. |
| 6,332,891 B1 | 12/2001 | Himes |
| 6,335,617 B1 | 1/2002 | Osadchy et al. |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson et al. |
| 6,368,331 B1 | 4/2002 | Front et al. |
| 6,369,571 B1 | 4/2002 | Damadian et al. |
| 6,369,574 B1 | 4/2002 | Ederlov et al. |
| 6,373,998 B2 | 4/2002 | Thirion et al. |
| 6,379,302 B1 | 4/2002 | Kessman et al. |
| 6,380,732 B1 | 4/2002 | Gilboa |
| 6,381,485 B1 | 4/2002 | Hunter et al. |
| 6,402,762 B2 | 6/2002 | Hunter et al. |
| 6,418,238 B1 | 7/2002 | Shiratani et al. |
| 6,421,551 B1 | 7/2002 | Kuth et al. |
| 6,424,856 B1 | 7/2002 | Vilsmeier et al. |
| 6,425,865 B1 | 7/2002 | Salcudean et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen et al. |
| 6,468,265 B1 | 10/2002 | Evans et al. |
| 6,469,508 B1 | 10/2002 | Damadian et al. |
| 6,470,066 B2 | 10/2002 | Takagi et al. |
| 6,470,207 B1 | 10/2002 | Simon et al. |
| 6,473,635 B1 | 10/2002 | Rasche |
| 6,477,400 B1 | 11/2002 | Barrick |
| 6,478,793 B1 | 11/2002 | Cosman et al. |
| 6,478,802 B2 | 11/2002 | Kienzle, III et al. |
| 6,483,948 B1 | 11/2002 | Spink et al. |
| 6,484,049 B1 | 11/2002 | Seeley et al. |
| 6,485,413 B1 | 11/2002 | Boppart et al. |
| D466,609 S | 12/2002 | Glossop |
| D466,610 S | 12/2002 | Ashton et al. |
| 6,490,467 B1 | 12/2002 | Bucholz et al. |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,498,944 B1 | 12/2002 | Ben-Haim et al. |
| 6,501,981 B1 | 12/2002 | Schweikard et al. |
| 6,504,893 B1 | 1/2003 | Flohr |
| 6,504,894 B2 | 1/2003 | Pan et al. |
| 6,516,213 B1 | 2/2003 | Nevo |
| 6,517,485 B2 | 2/2003 | Torp et al. |
| 6,527,443 B1 | 3/2003 | Vilsmeier et al. |
| 6,535,756 B1 | 3/2003 | Simon |
| 6,538,634 B1 | 3/2003 | Chui et al. |
| 6,539,127 B1 | 3/2003 | Roche et al. |
| 6,541,947 B1 | 4/2003 | Dittmer et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,562,059 B2 | 5/2003 | Edwards et al. |
| 6,567,687 B2 | 5/2003 | Front et al. |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,593,884 B1 | 7/2003 | Gilboa et al. |
| 6,606,513 B2 | 8/2003 | Lardo et al. |
| 6,609,022 B2 | 8/2003 | Vilsmeier et al. |
| 6,615,155 B2 | 9/2003 | Gilboa |
| 6,636,757 B1 | 10/2003 | Jascob et al. |
| 6,650,924 B2 | 11/2003 | Kuth et al. |
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,702,780 B1 | 3/2004 | Gilboa et al. |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,723,207 B2 | 4/2004 | Laser |
| 6,725,080 B2 | 4/2004 | Melkent et al. |
| 6,738,656 B1 | 5/2004 | Ferre et al. |
| 6,774,624 B2 | 8/2004 | Anderson et al. |
| 6,782,287 B2 | 8/2004 | Grzeszczuk et al. |

(56) References Cited

U.S. PATENT DOCUMENTS

| | | |
|---|---|---|
| 6,796,988 B2 | 9/2004 | Melkent et al. |
| 6,799,569 B2 | 10/2004 | Danielsson et al. |
| 6,823,207 B1 | 11/2004 | Jensen et al. |
| 6,826,423 B1 | 11/2004 | Hardy et al. |
| 6,833,814 B2 | 12/2004 | Gilboa et al. |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,899,672 B2 | 5/2005 | Chin et al. |
| 6,907,281 B2 | 6/2005 | Grzeszczuk |
| 6,920,347 B2 | 7/2005 | Simon et al. |
| 6,925,200 B2 | 8/2005 | Wood et al. |
| 6,934,575 B2 | 8/2005 | Ferre et al. |
| 6,947,788 B2 | 9/2005 | Gilboa et al. |
| 6,968,224 B2 | 11/2005 | Kessman et al. |
| 6,978,166 B2 | 12/2005 | Foley et al. |
| 6,982,090 B2 | 1/2006 | Gillespie |
| 6,989,303 B2 | 1/2006 | Mori |
| 6,992,477 B2 | 1/2006 | Govari |
| 6,996,430 B1 | 2/2006 | Gilboa et al. |
| 7,015,859 B2 | 3/2006 | Anderson |
| 7,015,907 B2 | 3/2006 | Tek et al. |
| 7,035,683 B2 | 4/2006 | Guendel |
| 7,050,845 B2 | 5/2006 | Vilsmeier |
| 7,115,100 B2 | 10/2006 | McRury et al. |
| 7,130,700 B2 | 10/2006 | Gardeski et al. |
| 7,139,601 B2 | 11/2006 | Bucholz et al. |
| 7,153,297 B2 | 12/2006 | Peterson |
| 7,171,257 B2 | 1/2007 | Thomson |
| 7,174,201 B2 | 2/2007 | Govari |
| 7,233,820 B2 | 6/2007 | Gilboa |
| 7,260,426 B2 | 8/2007 | Schweikard et al. |
| 7,300,428 B2 | 11/2007 | Ingenito |
| 7,339,587 B2 | 3/2008 | Kropfeld |
| 7,357,807 B2 | 4/2008 | Donohoe et al. |
| 7,366,562 B2 | 4/2008 | Dukesherer et al. |
| 7,371,067 B2 | 5/2008 | Anderson et al. |
| 7,398,116 B2 | 7/2008 | Edwards |
| 7,481,805 B2 | 1/2009 | Magnusson |
| 7,505,806 B2 | 3/2009 | Masutani et al. |
| 7,555,330 B2 | 6/2009 | Gilboa et al. |
| 7,594,925 B2 | 9/2009 | Danek et al. |
| 7,599,730 B2 | 10/2009 | Hunter et al. |
| 7,641,609 B2 | 1/2010 | Ohnishi et al. |
| 7,659,912 B2 | 2/2010 | Akimoto et al. |
| 7,697,972 B2 | 4/2010 | Verard et al. |
| 7,708,712 B2 | 5/2010 | Phan et al. |
| 7,756,563 B2 | 7/2010 | Higgins et al. |
| 7,778,691 B2 | 8/2010 | Zhang et al. |
| 7,835,493 B2 | 11/2010 | Keall et al. |
| 7,889,905 B2 | 2/2011 | Higgins et al. |
| 7,901,348 B2 | 3/2011 | Soper et al. |
| 7,949,385 B2 | 5/2011 | Khamene et al. |
| 7,962,193 B2 | 6/2011 | Edwards et al. |
| 7,969,143 B2 | 6/2011 | Gilboa |
| 7,979,244 B2 | 7/2011 | Fang et al. |
| 7,985,187 B2 | 7/2011 | Wibowo et al. |
| 7,988,639 B2 * | 8/2011 | Starks .................. G06T 17/20 600/508 |
| 7,998,062 B2 | 8/2011 | Gilboa |
| 8,002,465 B2 | 8/2011 | Ahn |
| 8,016,749 B2 | 9/2011 | Clerc et al. |
| 8,046,052 B2 | 10/2011 | Verard et al. |
| 8,049,777 B2 | 11/2011 | Akimoto et al. |
| 8,064,669 B2 | 11/2011 | Higgins et al. |
| 8,088,126 B2 | 1/2012 | Fugo |
| 8,096,957 B2 | 1/2012 | Conquergood et al. |
| 8,102,416 B2 | 1/2012 | Ito et al. |
| 8,150,138 B2 | 4/2012 | Ohnishi |
| 8,150,495 B2 | 4/2012 | Edwards et al. |
| 8,199,988 B2 | 6/2012 | Marshall et al. |
| 8,202,213 B2 | 6/2012 | Ito et al. |
| 8,214,015 B2 | 7/2012 | Macaulay et al. |
| 8,218,846 B2 | 7/2012 | Trumer et al. |
| 8,218,847 B2 | 7/2012 | Averbuch et al. |
| 8,219,179 B2 | 7/2012 | Ganatra et al. |
| 8,229,188 B2 | 7/2012 | Rusko et al. |
| 8,311,303 B2 | 11/2012 | Suehling et al. |
| 8,311,307 B2 | 11/2012 | Kitamura |
| 8,317,149 B2 | 11/2012 | Greenburg et al. |
| 8,317,726 B2 | 11/2012 | Timberlake et al. |
| 8,382,662 B2 | 2/2013 | Soper et al. |
| 8,428,328 B2 | 4/2013 | Averbuch et al. |
| 8,452,062 B2 | 5/2013 | Gogin et al. |
| 8,468,003 B2 | 6/2013 | Gibbs et al. |
| 8,473,032 B2 | 6/2013 | Averbuch |
| 8,483,801 B2 | 7/2013 | Edwards |
| 8,494,246 B2 | 7/2013 | Trumer et al. |
| 8,494,612 B2 | 7/2013 | Vetter et al. |
| 8,515,133 B2 | 8/2013 | Kitamura |
| 8,611,983 B2 | 12/2013 | Glossop |
| 8,611,984 B2 | 12/2013 | Greenburg et al. |
| 8,632,461 B2 | 1/2014 | Glossop |
| 8,672,836 B2 | 3/2014 | Higgins et al. |
| 8,675,935 B2 | 3/2014 | Higgins et al. |
| 8,696,548 B2 | 4/2014 | Gilboa |
| 8,696,685 B2 | 4/2014 | Gilboa |
| 8,700,132 B2 | 4/2014 | Ganatra et al. |
| 8,793,107 B2 | 7/2014 | Miller et al. |
| 8,965,108 B2 | 2/2015 | Chabanas et al. |
| 9,138,165 B2 * | 9/2015 | Holsing .................. G06T 19/00 |
| 9,171,377 B2 | 10/2015 | Kabus et al. |
| 9,265,468 B2 * | 2/2016 | Rai .......................... A61B 6/50 |
| 9,271,803 B2 | 3/2016 | Averbuch et al. |
| 9,390,552 B1 * | 7/2016 | Huang .................... G06T 17/00 |
| 9,404,734 B2 * | 8/2016 | Ramamurthy ..... A61B 1/00004 |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Kienzle, III et al. |
| 2001/0041835 A1 | 11/2001 | Front et al. |
| 2002/0044631 A1 | 4/2002 | Graumann et al. |
| 2002/0045812 A1 | 4/2002 | Ben-Haim et al. |
| 2002/0049375 A1 | 4/2002 | Strommer et al. |
| 2002/0049378 A1 | 4/2002 | Grzeszczuk et al. |
| 2002/0070970 A1 | 6/2002 | Wood et al. |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk |
| 2002/0085681 A1 | 7/2002 | Jensen |
| 2002/0143317 A1 | 10/2002 | Glossop |
| 2002/0161295 A1 | 10/2002 | Edwards et al. |
| 2002/0193685 A1 | 12/2002 | Mate et al. |
| 2003/0000535 A1 | 1/2003 | Galloway, Jr. et al. |
| 2003/0004411 A1 | 1/2003 | Govari et al. |
| 2003/0016852 A1 | 1/2003 | Kaufman et al. |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0029464 A1 | 2/2003 | Chen et al. |
| 2003/0032878 A1 | 2/2003 | Shahidi |
| 2003/0032936 A1 | 2/2003 | Lederman |
| 2003/0049667 A1 | 3/2003 | Wen-Tung et al. |
| 2003/0051733 A1 | 3/2003 | Kotmel et al. |
| 2003/0074011 A1 | 4/2003 | Gilboa et al. |
| 2003/0088179 A1 | 5/2003 | Seeley et al. |
| 2003/0114749 A1 | 6/2003 | Rahn |
| 2003/0125622 A1 | 7/2003 | Schweikard et al. |
| 2003/0130576 A1 | 7/2003 | Seeley et al. |
| 2003/0139663 A1 | 7/2003 | Graumann |
| 2003/0199785 A1 | 10/2003 | Hibner et al. |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0013548 A1 | 1/2004 | Seto et al. |
| 2004/0034300 A1 | 2/2004 | Verard et al. |
| 2004/0044350 A1 | 3/2004 | Martin et al. |

(56) References Cited

U.S. PATENT DOCUMENTS

| | | |
|---|---|---|
| 2004/0049121 A1 | 3/2004 | Yaron |
| 2004/0076259 A1 | 4/2004 | Jensen et al. |
| 2004/0091143 A1 | 5/2004 | Hu |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jascob et al. |
| 2004/0122311 A1 | 6/2004 | Cosman |
| 2004/0138548 A1 | 7/2004 | Strommer et al. |
| 2004/0152970 A1 | 8/2004 | Hunter et al. |
| 2004/0152974 A1 | 8/2004 | Solomon |
| 2004/0167393 A1 | 8/2004 | Solar et al. |
| 2004/0193042 A1 | 9/2004 | Scampini et al. |
| 2004/0210125 A1 | 10/2004 | Chen et al. |
| 2004/0249267 A1 | 12/2004 | Gilboa |
| 2005/0010099 A1 | 1/2005 | Raabe |
| 2005/0020900 A1 | 1/2005 | Yngvesson et al. |
| 2005/0027186 A1 | 2/2005 | Chen et al. |
| 2005/0033149 A1 | 2/2005 | Strommer et al. |
| 2005/0065433 A1 | 3/2005 | Anderson |
| 2005/0085718 A1 | 4/2005 | Shahidi |
| 2005/0085793 A1 | 4/2005 | Glossop |
| 2005/0107679 A1 | 5/2005 | Geiger et al. |
| 2005/0107688 A1 | 5/2005 | Strommer |
| 2005/0113809 A1 | 5/2005 | Melkent et al. |
| 2005/0137661 A1 | 6/2005 | Sra |
| 2005/0143651 A1 | 6/2005 | Verard et al. |
| 2005/0169510 A1 | 8/2005 | Zuhars et al. |
| 2005/0182295 A1 | 8/2005 | Soper et al. |
| 2005/0182319 A1 | 8/2005 | Glossop |
| 2005/0187482 A1 | 8/2005 | Obrien et al. |
| 2005/0197568 A1 | 9/2005 | Vass et al. |
| 2005/0203368 A1 | 9/2005 | Verin |
| 2005/0203383 A1 | 9/2005 | Moctezuma de la Barrera et al. |
| 2005/0203413 A1 | 9/2005 | Fichtinger et al. |
| 2005/0216237 A1* | 9/2005 | Adachi .............. G06T 17/00 703/1 |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1 | 1/2006 | Saracen |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0135961 A1 | 6/2006 | Rosenman et al. |
| 2006/0142798 A1 | 6/2006 | Holman et al. |
| 2006/0173269 A1 | 8/2006 | Glossop |
| 2006/0173291 A1 | 8/2006 | Glossop |
| 2006/0184016 A1 | 8/2006 | Glossop |
| 2006/0189867 A1 | 8/2006 | Revie et al. |
| 2006/0247511 A1 | 11/2006 | Anderson |
| 2006/0258933 A1 | 11/2006 | Ellis et al. |
| 2006/0270976 A1 | 11/2006 | Savage et al. |
| 2007/0032723 A1 | 2/2007 | Glossop |
| 2007/0038058 A1 | 2/2007 | West |
| 2007/0066887 A1 | 3/2007 | Mire et al. |
| 2007/0110289 A1 | 5/2007 | Fu et al. |
| 2007/0129629 A1 | 6/2007 | Beauregard et al. |
| 2007/0135803 A1 | 6/2007 | Belson |
| 2007/0167714 A1 | 7/2007 | Kiraly et al. |
| 2007/0167738 A1 | 7/2007 | Timinger et al. |
| 2007/0167744 A1 | 7/2007 | Beauregard et al. |
| 2007/0197896 A1 | 8/2007 | Moll et al. |
| 2007/0219059 A1 | 9/2007 | Schwartz et al. |
| 2007/0225559 A1 | 9/2007 | Clerc et al. |
| 2007/0232896 A1 | 10/2007 | Gilboa et al. |
| 2007/0244355 A1 | 10/2007 | Shaw |
| 2007/0249896 A1 | 10/2007 | Goldfarb et al. |
| 2007/0276180 A1 | 11/2007 | Greenburg et al. |
| 2007/0293721 A1 | 12/2007 | Gilboa |
| 2008/0071142 A1 | 3/2008 | Gattani et al. |
| 2008/0071143 A1 | 3/2008 | Gattani et al. |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0140114 A1 | 6/2008 | Edwards et al. |
| 2008/0167639 A1 | 7/2008 | Gilboa |
| 2008/0183071 A1 | 7/2008 | Strommer et al. |
| 2008/0221442 A1 | 9/2008 | Tolkowsky et al. |
| 2008/0247622 A1 | 10/2008 | Aylward et al. |
| 2008/0255416 A1 | 10/2008 | Gilboa |
| 2008/0262297 A1 | 10/2008 | Gilboa et al. |
| 2008/0262342 A1 | 10/2008 | Averbruch |
| 2008/0262430 A1 | 10/2008 | Anderson et al. |
| 2008/0269561 A1 | 10/2008 | Banik et al. |
| 2008/0287803 A1 | 11/2008 | Li et al. |
| 2009/0054908 A1 | 2/2009 | Zand et al. |
| 2009/0062789 A1 | 3/2009 | Rioux et al. |
| 2009/0088600 A1 | 4/2009 | Meloul |
| 2009/0156895 A1 | 6/2009 | Higgins et al. |
| 2009/0156951 A1 | 6/2009 | Averbuch |
| 2009/0209817 A1 | 8/2009 | Averbuch |
| 2009/0227861 A1 | 9/2009 | Ganatra et al. |
| 2009/0240140 A1 | 9/2009 | Fitelzon et al. |
| 2009/0240198 A1 | 9/2009 | Averbuch |
| 2009/0284255 A1 | 11/2009 | Zur |
| 2009/0306644 A1 | 12/2009 | Mayse et al. |
| 2010/0016757 A1 | 1/2010 | Greenburg et al. |
| 2010/0036241 A1 | 2/2010 | Mayse et al. |
| 2010/0041949 A1 | 2/2010 | Tolkowsky |
| 2010/0137707 A1 | 6/2010 | Hunter et al. |
| 2010/0160733 A1 | 6/2010 | Gilboa |
| 2011/0054304 A1 | 3/2011 | Markowitz et al. |
| 2011/0054309 A1* | 3/2011 | Edwards .............. A61B 5/055 600/424 |
| 2011/0058721 A1* | 3/2011 | Zhang .............. A61B 5/091 382/131 |
| 2011/0102432 A1 | 5/2011 | Melkisetoglu et al. |
| 2011/0118593 A1 | 5/2011 | Melkent et al. |
| 2011/0158488 A1 | 6/2011 | Cohen et al. |
| 2011/0190660 A1 | 8/2011 | Levy |
| 2011/0301587 A1 | 12/2011 | Deem et al. |
| 2012/0046521 A1 | 2/2012 | Hunter et al. |
| 2012/0059220 A1 | 3/2012 | Holsing et al. |
| 2012/0059248 A1 | 3/2012 | Holsing et al. |
| 2012/0065481 A1 | 3/2012 | Hunter et al. |
| 2012/0071753 A1 | 3/2012 | Hunter et al. |
| 2012/0123296 A1 | 5/2012 | Hashimshony et al. |
| 2012/0275689 A1* | 11/2012 | Birtwistle .............. G06T 5/005 382/154 |
| 2013/0184569 A1 | 7/2013 | Strommer et al. |
| 2014/0343408 A1 | 11/2014 | Tolkowsky |

FOREIGN PATENT DOCUMENTS

| | | |
|---|---|---|
| DE | 19829224 A1 | 1/2000 |
| DE | 19909816 A1 | 5/2000 |
| DE | 199909816 | 5/2000 |
| DE | 10000937 A1 | 8/2001 |
| DE | 10136709 A1 | 2/2003 |
| DE | 10161160 A1 | 6/2003 |
| DE | 102005010010 A1 | 9/2005 |
| DE | 102004030836 A1 | 1/2006 |
| DE | 102005026251 A1 | 1/2006 |
| DE | 102005038394 A1 | 3/2006 |
| DE | 102005050286 A1 | 4/2006 |
| DE | 102004058122 A1 | 7/2006 |
| EP | 0501993 A1 | 9/1992 |
| EP | 0869745 A2 | 10/1998 |

(56) References Cited

FOREIGN PATENT DOCUMENTS

| | | |
|---|---|---|
| EP | 900048 A1 | 3/1999 |
| EP | 0928600 A2 | 7/1999 |
| EP | 977510 A1 | 2/2000 |
| EP | 1079240 A2 | 2/2001 |
| EP | 1152706 A1 | 11/2001 |
| EP | 1181897 A2 | 2/2002 |
| EP | 1274792 A1 | 1/2003 |
| EP | 1319368 A2 | 6/2003 |
| EP | 1374793 A1 | 1/2004 |
| EP | 1391181 A1 | 2/2004 |
| EP | 1421913 A1 | 5/2004 |
| EP | 1464285 A1 | 10/2004 |
| EP | 1504713 A1 | 2/2005 |
| EP | 1504726 A1 | 2/2005 |
| EP | 1519140 A1 | 3/2005 |
| EP | 1523951 A2 | 4/2005 |
| EP | 1561423 A1 | 8/2005 |
| EP | 1629774 A1 | 3/2006 |
| EP | 1629789 A1 | 3/2006 |
| EP | 2380550 A2 | 10/2011 |
| FR | 2876273 A1 | 4/2006 |
| JP | 2000023941 A | 1/2000 |
| QA | 9501757 A1 | 1/1995 |
| WO | 9424933 A1 | 11/1994 |
| WO | 9608209 A2 | 3/1996 |
| WO | 9610949 A1 | 4/1996 |
| WO | 9626672 A1 | 9/1996 |
| WO | 9729699 A1 | 8/1997 |
| WO | 9729709 A1 | 8/1997 |
| WO | 9836684 A1 | 8/1998 |
| WO | 9916352 A1 | 4/1999 |
| WO | 9927839 A2 | 6/1999 |
| WO | 9943253 A1 | 9/1999 |
| WO | 0016684 A1 | 3/2000 |
| WO | 0028911 A1 | 5/2000 |
| WO | 0047103 A2 | 8/2000 |
| WO | 0049958 A1 | 8/2000 |
| WO | 0057767 A2 | 10/2000 |
| WO | 0069335 A1 | 11/2000 |
| WO | 0101845 A2 | 1/2001 |
| WO | 0137748 A2 | 5/2001 |
| WO | 0162134 A2 | 8/2001 |
| WO | 0164124 A1 | 9/2001 |
| WO | 0176496 A1 | 10/2001 |
| WO | 0176497 A1 | 10/2001 |
| WO | 0187136 A2 | 11/2001 |
| WO | 0193745 A2 | 12/2001 |
| WO | 0200093 A2 | 1/2002 |
| WO | 0200103 A2 | 1/2002 |
| WO | 0219936 A2 | 3/2002 |
| WO | 0222015 A2 | 3/2002 |
| WO | 0224051 A2 | 3/2002 |
| WO | 06027781 | 3/2002 |
| WO | 06039009 | 3/2002 |
| WO | 06051523 | 3/2002 |
| WO | 02056770 A1 | 7/2002 |
| WO | 02064011 A2 | 8/2002 |
| WO | 02082375 A2 | 10/2002 |
| WO | 2098273 A2 | 12/2002 |
| WO | 2004046754 A2 | 6/2004 |
| WO | 2004060157 A1 | 7/2004 |
| WO | 2004062497 A1 | 7/2004 |
| WO | 2005016166 A2 | 2/2005 |
| WO | 200507293 | 8/2005 |
| WO | 2005070318 A1 | 8/2005 |
| WO | 2005101277 A2 | 10/2005 |
| WO | 2005111942 A1 | 11/2005 |
| WO | 2006002396 A2 | 1/2006 |
| WO | 2006005021 A2 | 1/2006 |
| WO | 2006039009 A2 | 4/2006 |
| WO | 2006051523 A2 | 5/2006 |
| WO | 2006090141 A1 | 8/2006 |
| WO | 2007002079 A2 | 1/2007 |
| WO | 2007031314 A2 | 3/2007 |
| WO | 2007033206 A2 | 3/2007 |
| WO | 2007062051 A2 | 5/2007 |
| WO | 2007084893 A2 | 7/2007 |
| WO | 2009158578 A1 | 12/2009 |
| WO | 2012024686 A2 | 2/2012 |

OTHER PUBLICATIONS

FDA Approves Lung Sealant, May 31, 2000 [online], [retrieved Oct. 17, 2008 from Internet]; http://www.meds.com/archive/mol-cancer/2000/05/msg01329.html Aug. 31, 2000.
Highlights from Presentation of 5th Joint Meeting of European Assn. For Cardio-Thoracic Surgery and European Society of Thoracic Surgeons "Evidence for Fleece-Bound Sealants in Cardiothoracic Surgery" Sep. 9-13, 2006 Sep. 9, 2006.
Medical Industry Today, "New Navigational Aid Could Improve Hip Replacement Outcomes," Jul. 22, 1997.
Moore, E. et al., Needle Aspiration Lung Biopsy: Re-evaluation of the blood patch technique in an equine model, Radiology, 196(1) Jul. 1, 1995.
Patent Cooperation Treaty, International Search Report and Written Opinion from PCT/US06/35548, dated Aug. 20, 2007, 7 pages.
Patent Cooperation Treaty, International Search Report from PCT/US11/48669, dated Apr. 9, 2012, 7 pages.
Nov. 29, 2017 USPTO Office Action (U.S. Appl. No. 13/773,981).
Dec. 4, 2015 USPTO Office Action (U.S. Appl. No. 13/773,981).
Feb. 11, 2016 USPTO Office Action (U.S. Appl. No. 13/773,997).
Apr. 30, 2019 USPTO Office Action (U.S. Appl. No. 13/773,990).
May 17, 2017 USPTO Office Action (U.S. Appl. No. 13/773,981).
Mar. 10, 2015 USPTO Office Action (U.S. Appl. No. 13/773,997).
Mar. 14, 2018 USPTO Office Action (U.S. Appl. No. 151287,648).
Mar. 15, 2018 USPTO Office Action (U.S. Appl. No. 13/773,990).
Mar. 29, 2016 USPTO Office Action (U.S. Appl. No. 13/773,990).
Jul. 7, 2015 USPTO Office Action (U.S. Appl. No. 13/773,990).
Aug. 4, 2014 USPTO Office Action (U.S. Appl. No. 13/773,990).
Sep. 9, 2016 USPTO Office Action (U.S. Appl. No. 13/773,981).

* cited by examiner

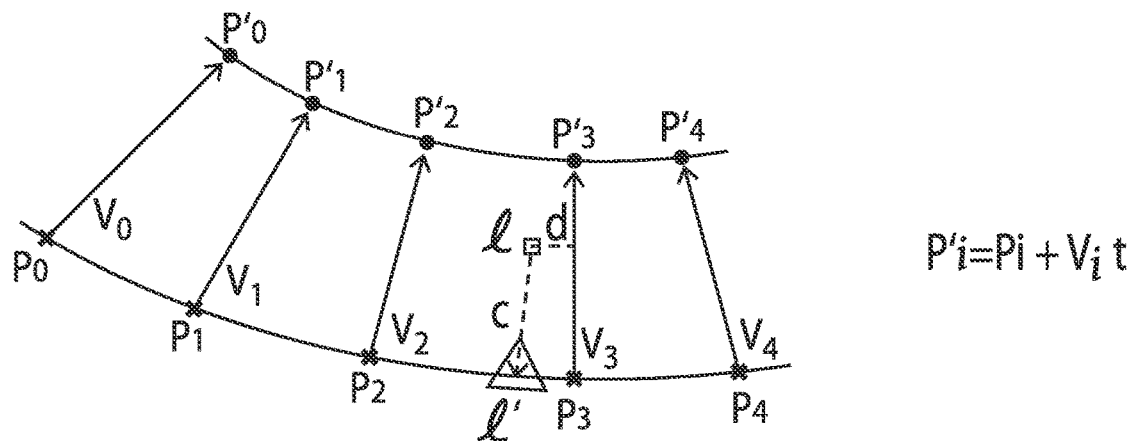

$P'_i = P_i + V_i t$ $P_i \equiv$ Data point in 4D-gated point cloud at expiration $P'_i \equiv$ Data point in 4D-gated point cloud at inspiration $V_i \equiv$ expiration to inspiration deformation vector $\ell \equiv$ 3D localized point $d \equiv$ distance to nearest $V_i$ (point to line)

$c \equiv$ real time respiration correction vector (variables and algorithm also applicable to heartbeat, vessel motion, etc.)

FIG. 9

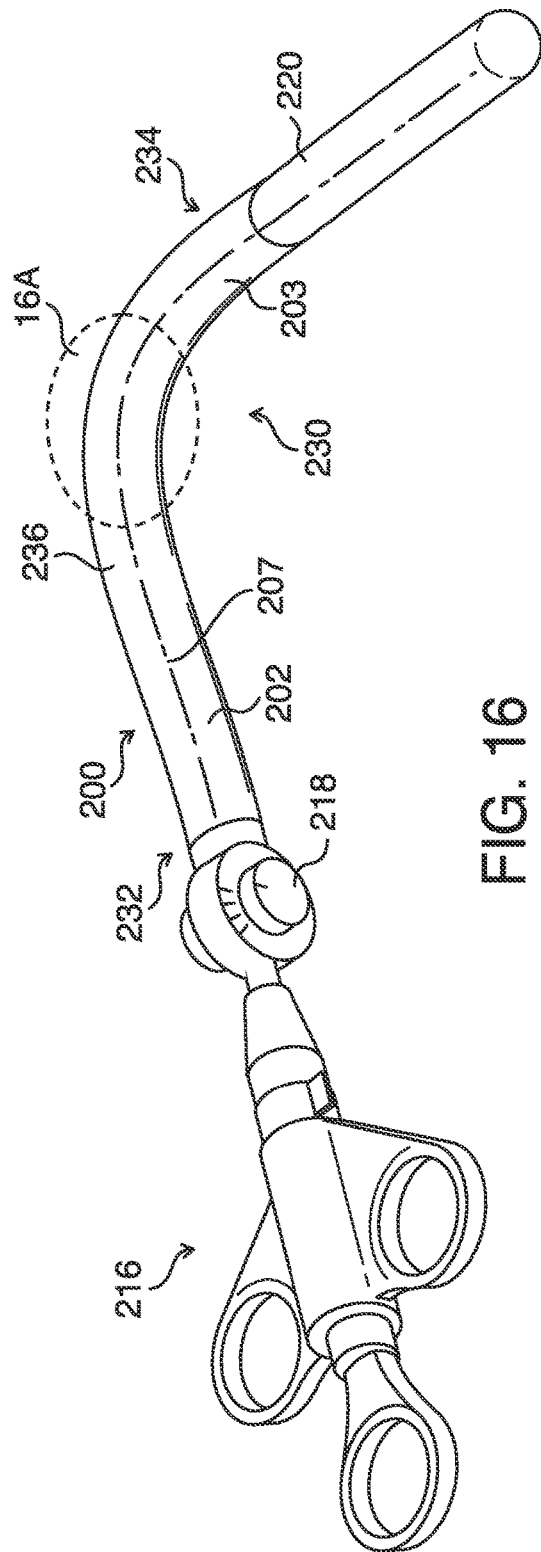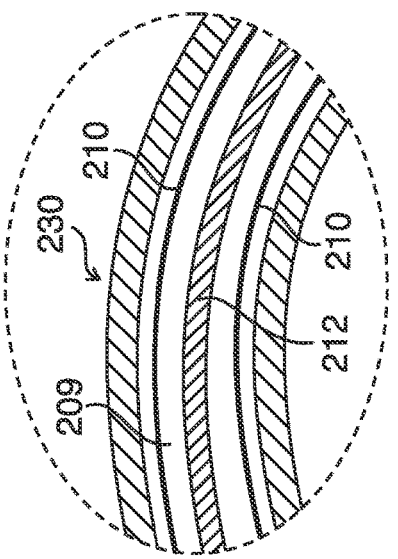
FIG. 16
FIG. 16A

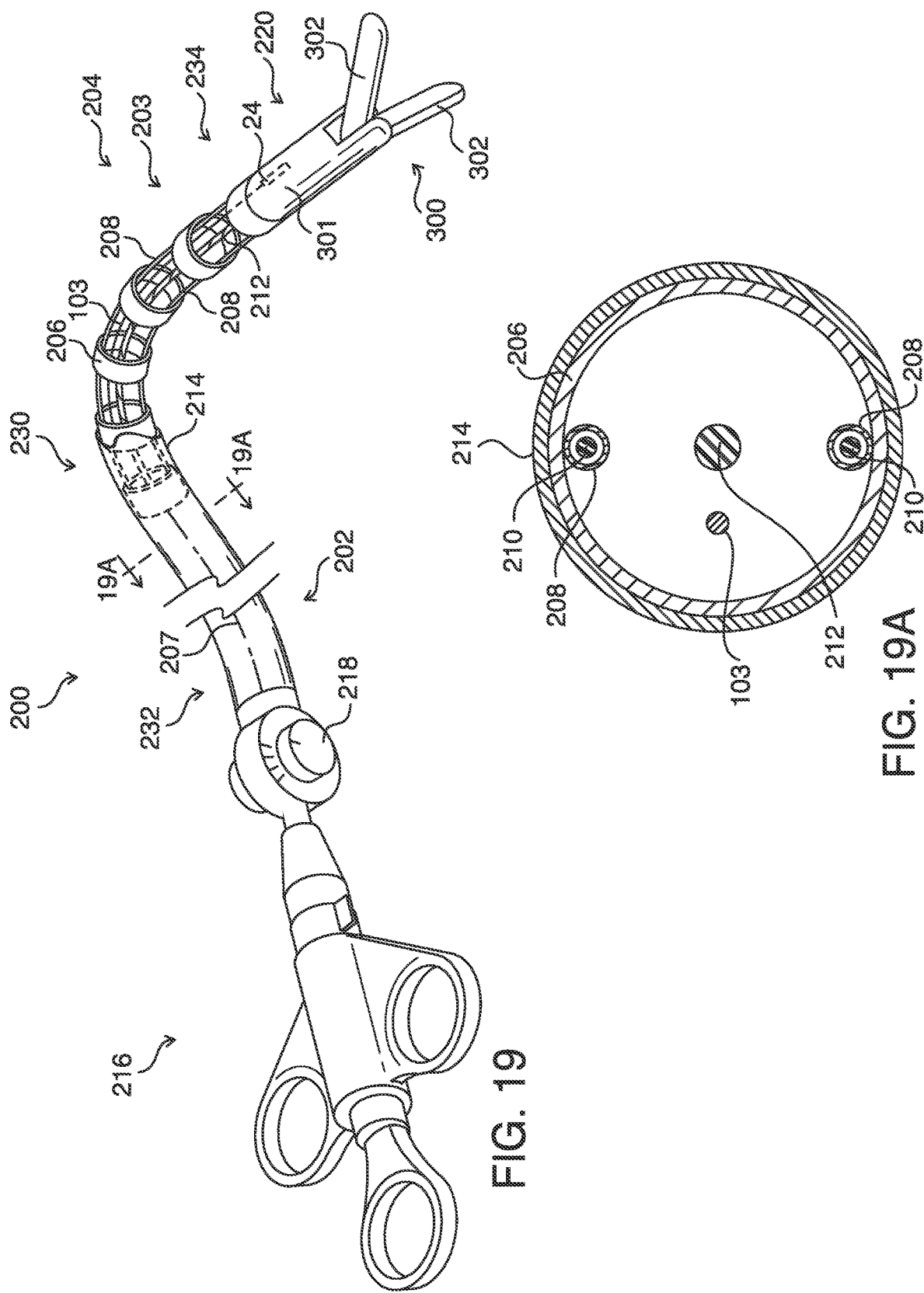

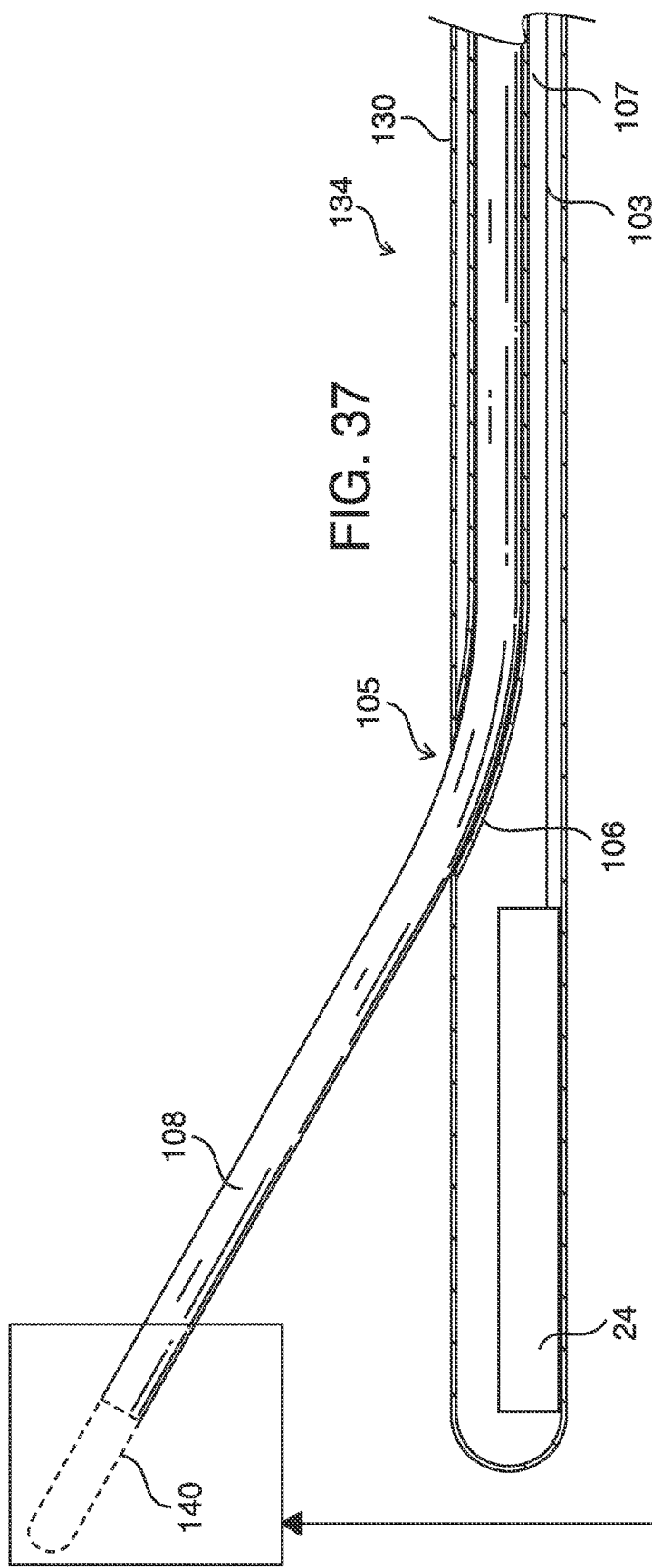
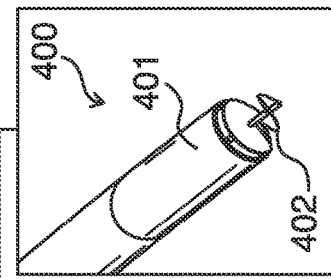
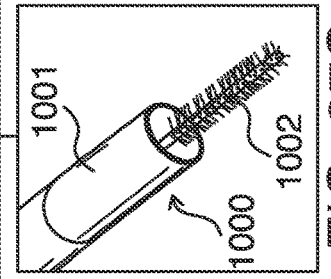
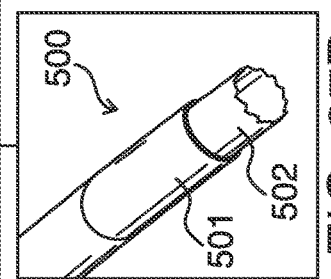
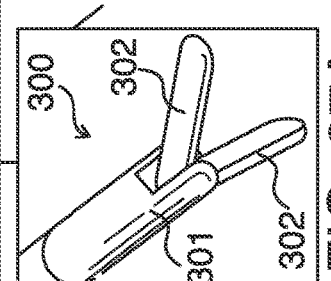

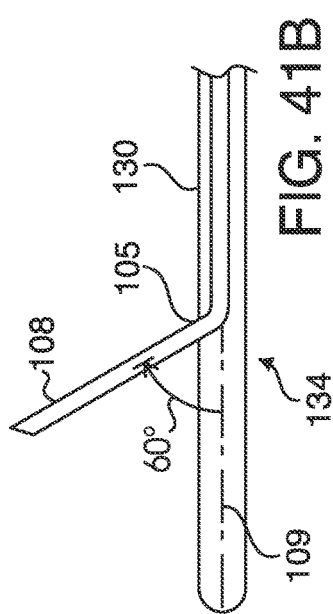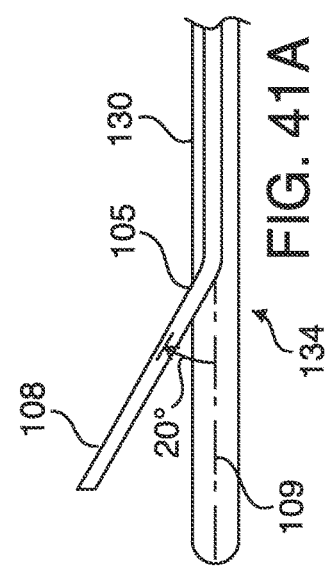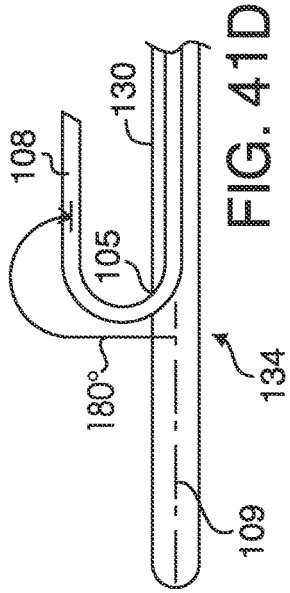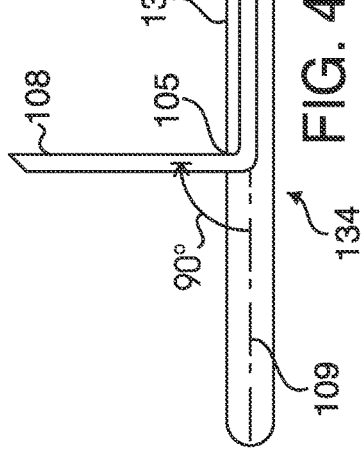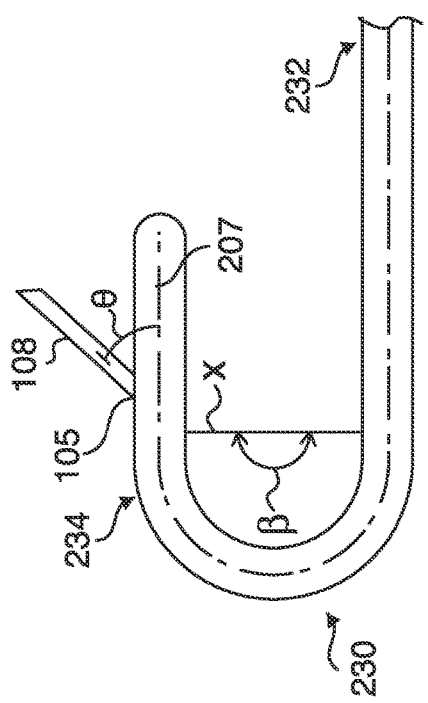

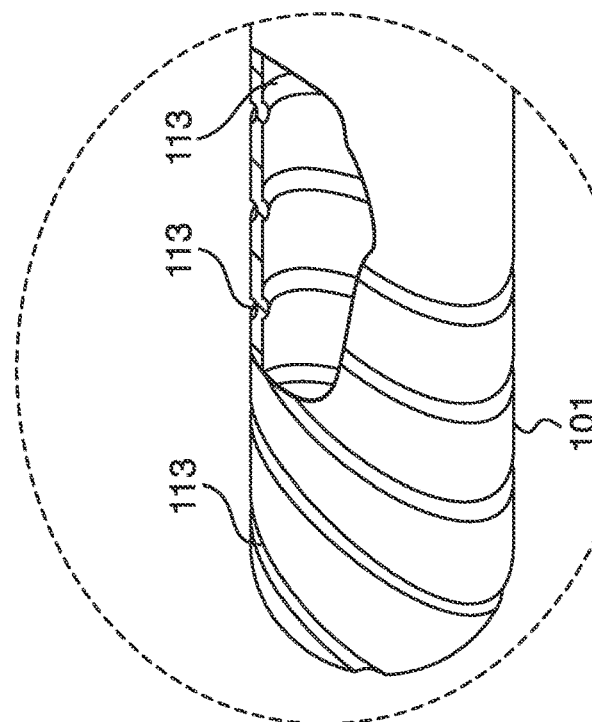
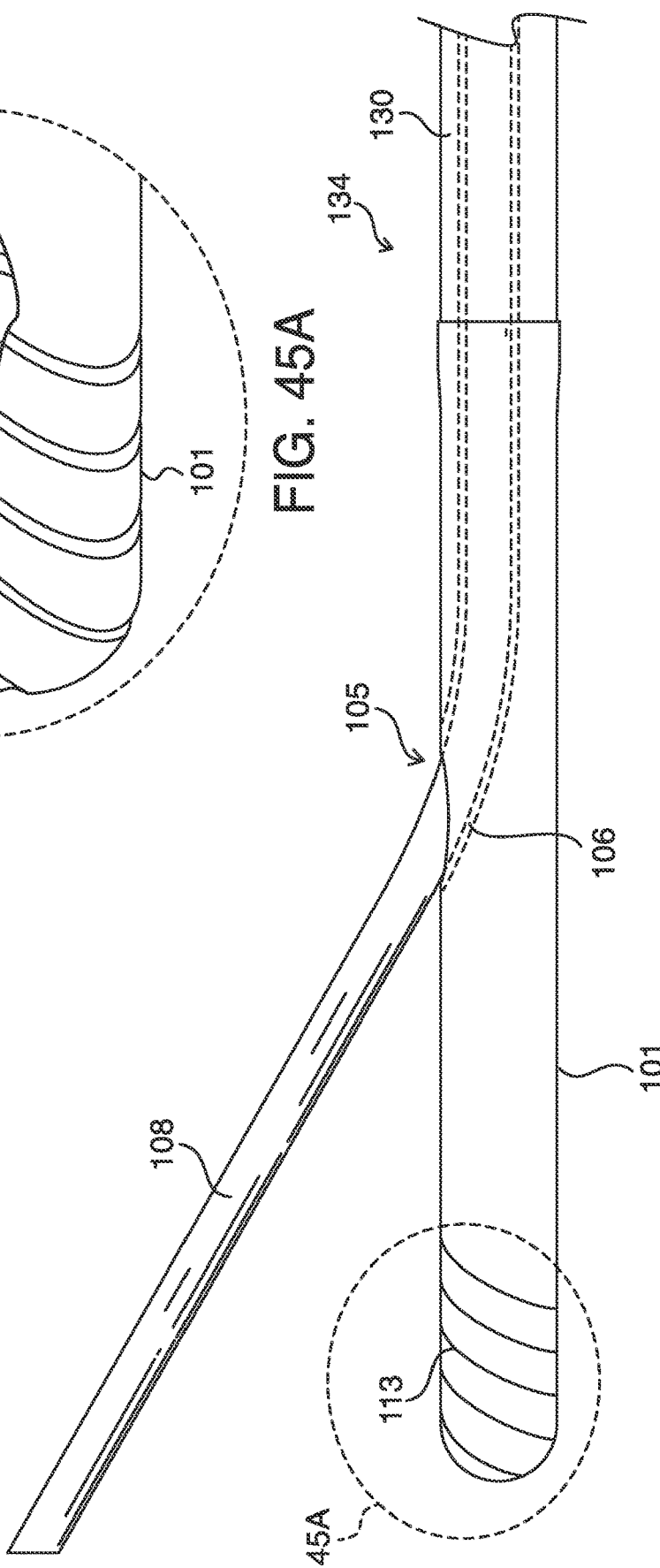

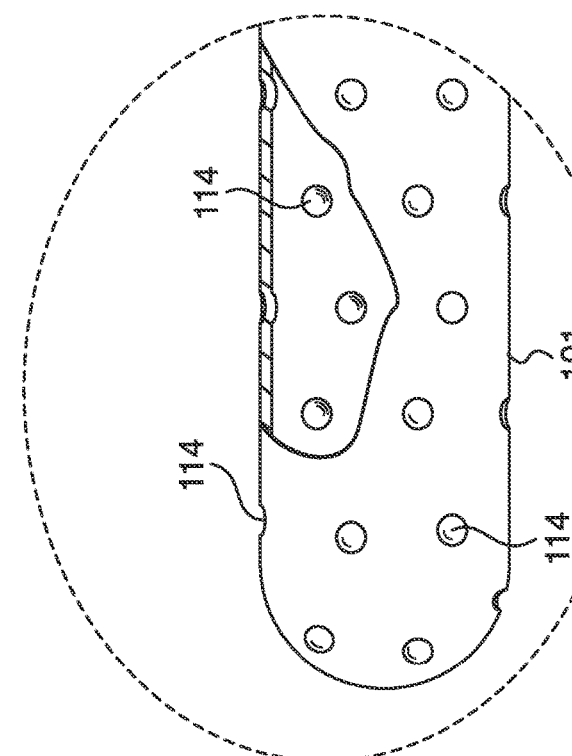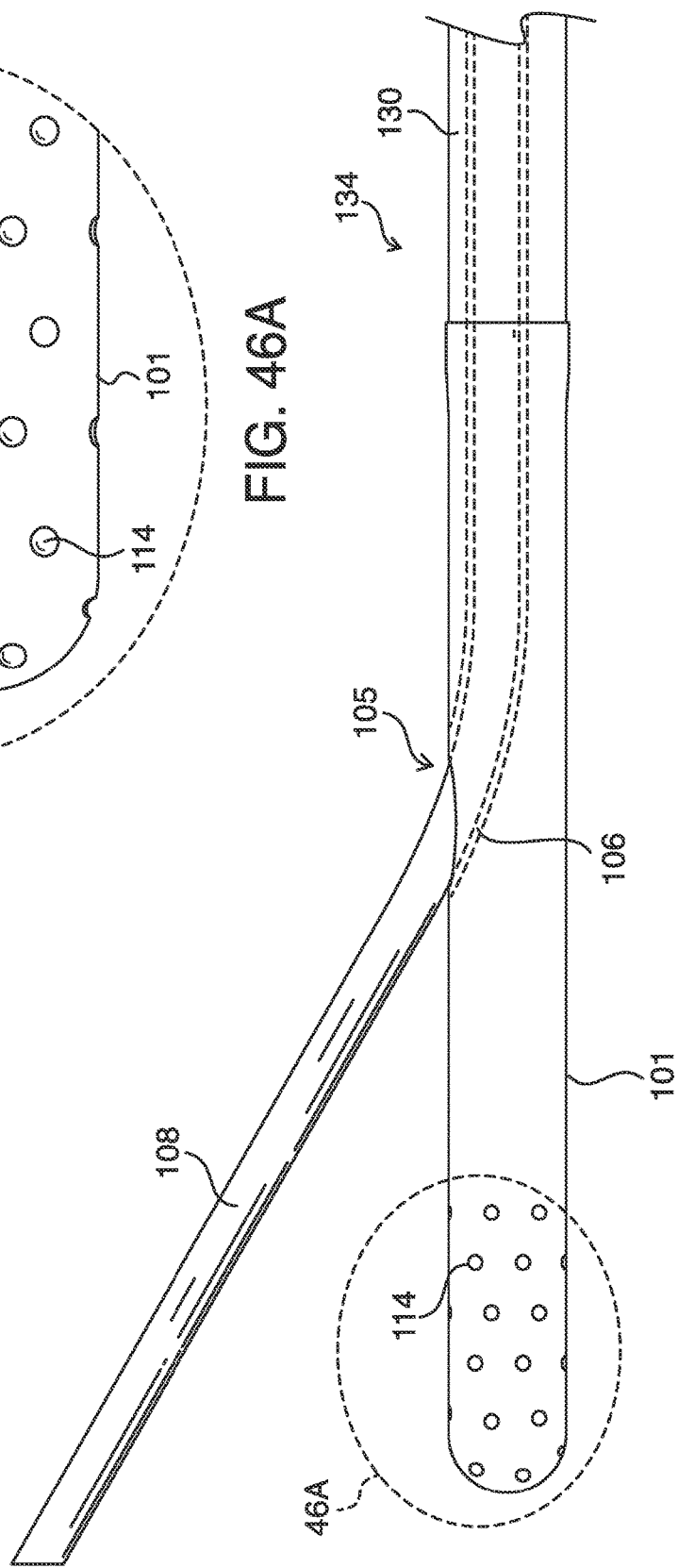

SYSTEMS, METHODS AND DEVICES FOR FORMING RESPIRATORY-GATED POINT CLOUD FOR FOUR DIMENSIONAL SOFT TISSUE NAVIGATION

FIELD OF INVENTION

The present invention generally relates to devices and methods associated with a medical procedure, and, in one embodiment, to medical devices for use in and methods associated with the respiratory system.

BACKGROUND

Image guided surgery (IGS), also known as image guided intervention (IGI), enhances a physician's ability to locate instruments within a patient's anatomy during a medical procedure. IGS can include 2-dimensional (2D), 3-dimensional (3D), and 4-dimensional (4D) applications. The fourth dimension of IGS can include multiple parameters either individually or together such as time, motion, electrical signals, pressure, airflow, blood flow, respiration, heartbeat, and other patient measured parameters.

Existing imaging modalities can capture the movement of dynamic anatomy. Such modalities include electrocardiogram (ECG)-gated or respiratory-gated magnetic resonance imaging (MRI) devices, ECG-gated or respiratory-gated computer tomography (CT) devices, standard computed tomography (CT), 3D Fluoroscopic images (Angio-suites), and cinematography (CINE) fluoroscopy and ultrasound. Multiple image datasets can be acquired at different times, cycles of patient signals, or physical states of the patient. The dynamic imaging modalities can capture the movement of anatomy over a periodic cycle of that movement by sampling the anatomy at several instants during its characteristic movement and then creating a set of image frames or volumes.

Although significant improvements have been made in these fields, a need remains for improved medical devices and procedures for visualizing, accessing and manipulating a targeted anatomical tissue.

SUMMARY OF THE INVENTION

Among the various aspects of the present invention may be noted devices for use in and methods associated with medical procedures; such devices and methods, for example, may include devices and methods that enhance a physician's ability to locate instruments within anatomy during a medical procedure, such as image guided surgery (IGS) or image guided intervention (IGI) and such devices and methods may further include devices and methods that facilitate accessing and manipulating a targeted anatomical tissue.

Briefly, therefore, one aspect of the present invention is a method for modifying or deforming a segmented image dataset for a region of a respiratory system of a patient to the corresponding anatomy of a patient's respiratory system. The method comprises (i) forming a respiratory-gated point cloud of data that demarcates anatomical features in a region of a patient's respiratory system at one or more discrete phases within a respiration cycle of a patient, (ii) density filtering the respiratory-gated point cloud, (iii) classifying the density filtered respiratory-gated point cloud according to anatomical points of reference in a segmented image dataset for the region of the patient's respiratory system, and (iv) modifying the segmented image dataset to correspond to the classified anatomical points of reference in the density filtered respiratory-gated point cloud.

Another aspect of the present invention is a method of preparing a segmented image dataset to match the anatomy of a patient's respiratory system. The method comprises forming a respiratory-gated point cloud of data that demarcates anatomical features in a region of a patient's respiratory system at one or more discrete phases within a respiration cycle of a patient. The method further comprises density filtering the respiratory-gated point cloud, classifying the density filtered respiratory-gated point cloud according to anatomical points of reference in a segmented image dataset for the region of the patient's respiratory system, registering the classified respiratory-gated point cloud to the segmented image dataset, comparing the registered respiratory-gated point cloud to a segmented image dataset to determine the weighting of points comprised by the classified respiratory-gated point cloud, distinguishing regions of greater weighting from regions of lesser weighting and modifying the segmented image dataset to correspond to the classified respiratory-gated point cloud.

A further aspect of the present invention is a method for simulating the movement of a patient's respiratory system during respiration. The simulation method comprises (i) forming a respiratory-gated point cloud of data that demarcates anatomical features in a region of a patient's respiratory system at one or more discrete phases within a respiration cycle of a patient, (ii) density filtering the respiratory-gated point cloud, (iii) classifying the density filtered respiratory-gated point cloud according to anatomical points of reference in a segmented image dataset for the region of the patient's respiratory system, (iv) creating a cine loop comprising a plurality of modified segmented image datasets through multiple modifications of the segmented image dataset to correspond to a plurality of classified anatomical points of reference in the respiratory-gated point cloud over the respiration cycle, and (v) displaying the cine loop comprising the plurality of modified segmented image datasets over the patient's respiration cycle.

A still further aspect of the present invention is a surgical catheter for use in medical procedures. The surgical catheter comprises an elongate flexible shaft having a longitudinal axis, a proximal end portion, a distal end portion, and a handle attached to the proximal end portion. The elongate flexible shaft further comprises an outer wall extending from the proximal end portion to the distal end portion. The surgical catheter further comprises a biopsy device at the distal end portion, and an actuation wire extending from the proximal end portion to the distal end portion to operate the biopsy device. Additionally, a steering mechanism is connected to the steering actuator wherein the distal end portion may be moved relative to the proximal end portion by manipulating the steering actuator.

A still further aspect of the present invention is an apparatus comprising a steerable catheter comprising a biopsy device for accessing or manipulating tissue.

A yet further aspect of the present invention is a surgical catheter for navigated surgery, the surgical catheter comprises an elongate flexible shaft having a longitudinal axis, a proximal end portion, a distal end portion, a side exit in the distal end portion, and a handle attached to the proximal end portion. The elongate flexible shaft further comprises an outer wall extending from the proximal end portion to the distal end portion, and an electromagnetic localization element at the distal end portion. A medical instrument housed within the elongate flexible shaft that is extendable along a path from a position within the outer wall and through the side exit to an extended position outside the outer wall, the medical instrument being disposed at an angle of at least 10 degrees relative to the longitudinal axis at the side exit when in the extended position. The position of the medical instrument along the path can be calibrated to the location of the electromagnetic localization element and displayed by a surgical instrument navigation system.

A further aspect of the present invention is a method of guiding a surgical instrument to a region of interest in a patient. The method comprises displaying an image of the region of the patient, inserting a flexible lumen into the region of the patient, inserting a surgical catheter comprising an electromagnetic localization element into the lumen, navigating the surgical catheter to the region of interest, detecting a location and orientation of the electromagnetic localization element, displaying, in real-time, a virtual representation of the surgical catheter and the medical instrument superimposed on the image based upon the location and orientation of the electromagnetic localization element, and performing a medical procedure at the region of interest.

A further aspect of the present invention is a method of placing a localization element in an organ of a patient for use in a medical procedure. The method comprises attaching a first localization element to tissue in a region of the organ of a patient using an endolumenal device. The attached localization element may be separate from the endolumenal device and is registered to a segmented image dataset. The body of the patient may then be modified such that the body does not match the segmented image dataset, and the position of the first localization element is identified from outside the patient's organ using a second localization element to facilitate a medical procedure.

Other objects and features will be in part apparent and in part pointed out hereinafter.

BRIEF DESCRIPTION OF THE DRAWINGS

The details of the present invention, both as to its construction and operation can best be understood with reference to the accompanying drawings, in which like numerals refer to like parts, and in which:

FIG. 9 depicts an exemplary real-time respiration compensation algorithm according to an embodiment of the present invention;

FIGS. 16 and 16A show a side perspective view and a cutaway view of a steerable catheter according to an embodiment of the present invention;

FIGS. 19 and 19A are a top cutaway view and a cross-section view of a navigated steerable catheter wherein the steerable shaft portion comprises spline rings according to an embodiment of the present invention;

FIG. 37 is a side cutaway view of the surgical catheter wherein the medical instrument may comprise possible devices including a forceps device (FIG. 37A), a boring bit device (FIG. 37B), a brush device (FIG. 37C), and an auger device (FIG. 37D) according to various embodiment of the present invention;

FIGS. 41A-41D are side views of the medical instrument in the extended position disposed at various angles relative to the longitudinal axis of an elongate flexible shaft at a side exit according to an embodiment of the present invention;

FIG. 41E is a side view of the medical instrument in the extended position disposed at an angle relative to the longitudinal axis of an elongate flexible shaft at a side exit wherein an arc is introduced into the elongate flexible shaft according to an embodiment of the present invention;

FIGS. 45 and 45A are a side view, and detailed partially cut-away view of the surgical catheter comprising an echogenic pattern visible via ultrasonic imaging according to an embodiment of the present invention;

FIGS. 46 and 46A are a side view, and detailed partially cut-away view of the surgical catheter comprising an echogenic pattern of partially spherical indentations visible via ultrasonic imaging according to an embodiment of the present invention;

DETAILED DESCRIPTION

Figure 1:
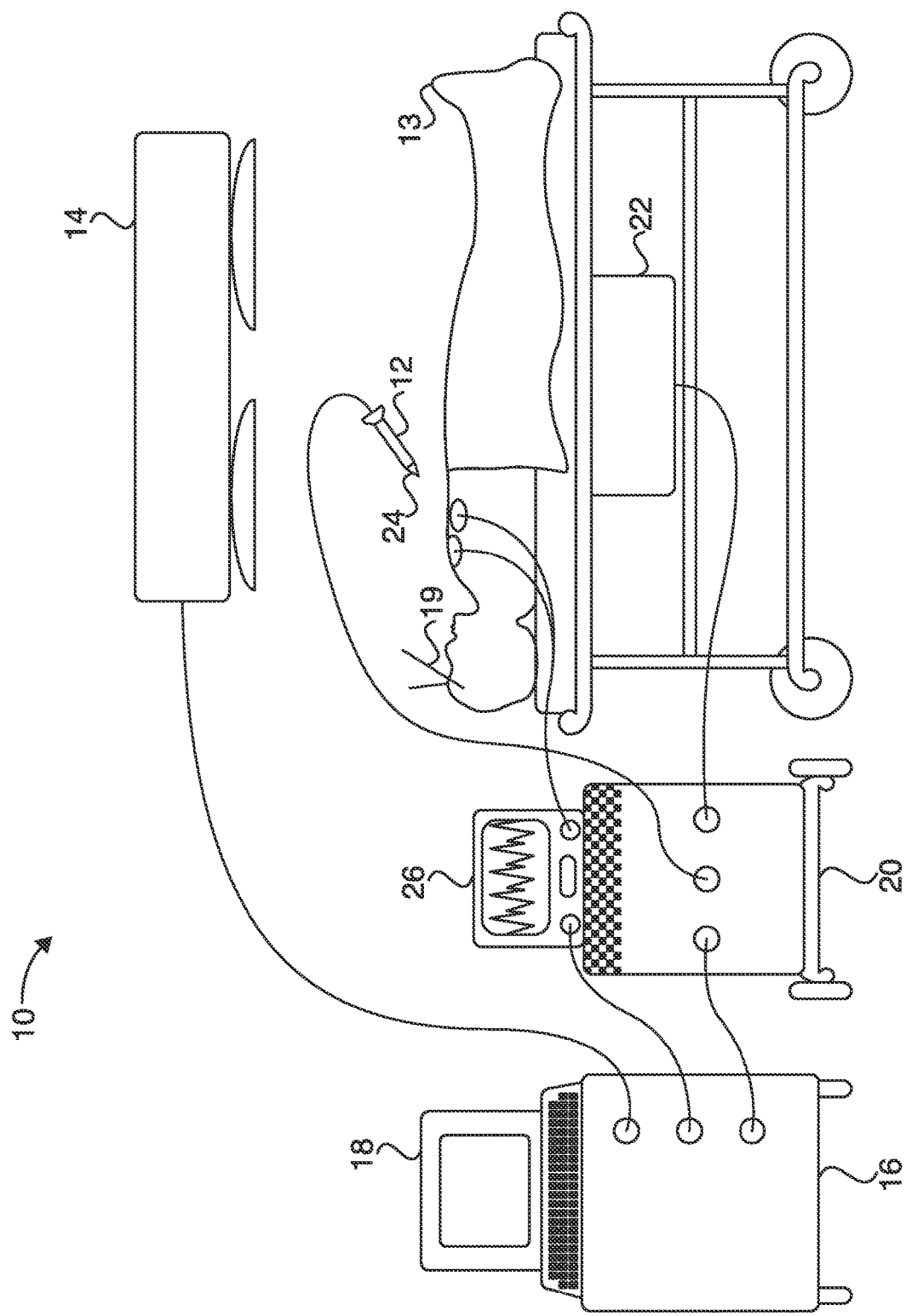
FIG. 1 is a schematic illustration of an exemplary surgical instrument navigation system according to an embodiment of the present invention.

Referring now to FIG. 1, a surgical instrument navigation system 10 in accordance with one embodiment of the present invention is operable to visually simulate a virtual volumetric scene within the body of a patient, such as an internal body cavity, from a point of view of a surgical instrument 12 residing in the cavity of a patient 13. The surgical instrument navigation system 10 comprises a surgical instrument 12, a processor 16 having a display 18, and a tracking subsystem 20. The surgical instrument navigation system 10 may further include (or is accompanied by) an imaging device 14 that is operable to provide image data to the system.

Imaging device 14 can be used to capture images or data of patient 13. Imaging device 14 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, or any other suitable medical imaging device. In one embodiment, imaging device 14 is a computed tomography—positron emission tomography device that produces a fused computed tomography—positron emission tomography image dataset. Imaging device 14 is in communication with processor 16 and can send, transfer, copy and/or provide image data taken (captured) of patient 13 to processor 16.

Processor 16 includes a processor-readable medium storing code representing instructions to cause processor 16 to perform a process. Processor 16 may be, for example, a commercially available personal computer, or a less complex computing or processing device that is dedicated to performing one or more specific tasks. For example, processor 16 may be a terminal dedicated to providing an interactive graphical user interface (GUI). Alternatively, processor 16 may be a commercially available microprocessor, an application-specific integrated circuit (ASIC) or a combination of ASICs, which are designed to achieve one or more specific functions, or enable one or more specific devices or applications. In yet another embodiment, processor 16 may be an analog or digital circuit, or a combination of multiple circuits.

Processor 16 preferably includes a memory component (not shown) comprising one or more types of memory devices. For example, the memory component may comprise a read only memory (ROM) device and/or a random access memory (RAM) device. The memory component may also comprise other types of memory devices that may be suitable for storing data in a form retrievable by processor 16. For example, the memory component may comprise electronically programmable read only memory (EPROM), erasable electronically programmable read only memory (EEPROM), flash memory, as well as other suitable forms of memory. The memory component may also comprise a non-transitory processor-readable medium. Processor 16 may also include a variety of other components, such as for example, coprocessors, graphic processors, etc., depending upon the desired functionality of the code. Processor 16 can store data in or retrieve data from the memory component.

Processor 16 may also comprise components to communicate with devices external to processor 16 by way of an input/output (I/O) component (not shown). According to one or more embodiments of the invention, the I/O component can include a variety of suitable communication interfaces. For example, the I/O component can include wired connections, such as standard serial ports, parallel ports, universal serial bus (USB) ports, S-video ports, local area network (LAN) ports, and small computer system interface (SCSI) ports. Additionally, the I/O component may include, for example, wireless connections, such as infrared ports, optical ports, Bluetooth® wireless ports, wireless LAN ports, or the like.

In one embodiment, processor 16 is connected to a network (not shown), which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

In one embodiment, processor 16 can receive image data from imaging device 14 and generate a segmented image dataset using various segmentation techniques, such as Hounsfield unit thresholding, convolution, connected component, or other combinatory image processing and segmentation techniques. For example, in one embodiment processor 16 can determine a distance and direction between the position of any two data points within a respiratory-gated point cloud (as described in greater detail elsewhere herein) during multiple instants in time, and store the image data, as well as the position and distance data, within the memory component. Multiple images can be produced providing a visual image at multiple instants in time through the path of motion of the patient's body.

Figure 10:
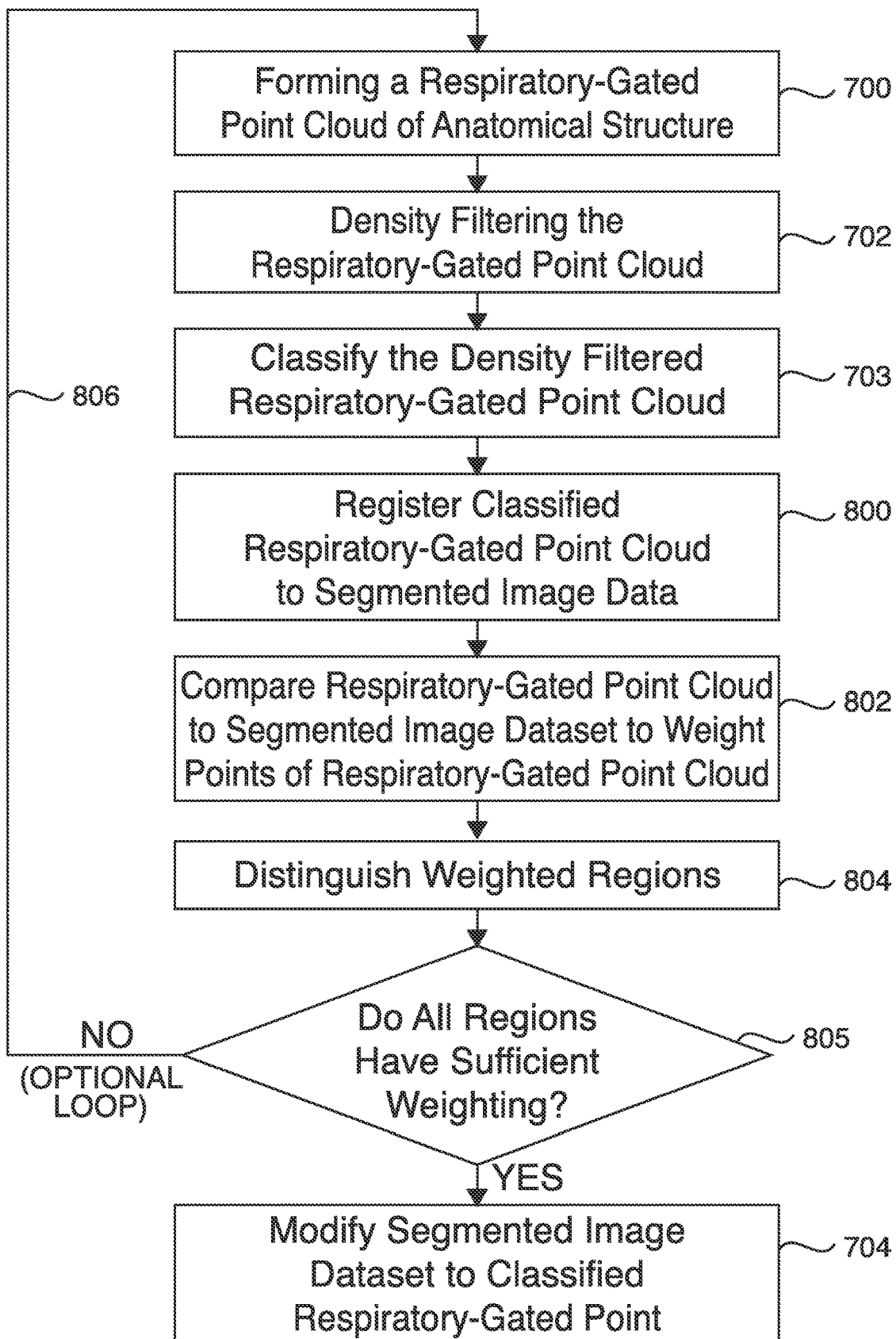
FIG. 10 is a flow chart depicting the registration of a respiratory-gated point cloud to a segmented image dataset and the subsequent deformation of a segmented image dataset to the respiratory-gated point cloud according to an embodiment of the present invention.

Surgical instrument 12 may be any medical device used in a medical procedure. In one embodiment, surgical instrument 12 comprises a relatively flexible catheter that may be guided to the region or tissue of interest. Thus, for example, surgical instrument 12 may comprise or be used to implant one or more surgical devices such as a guide wire, a pointer probe, a stent, a seed, an implant, or an endoscope. It is also envisioned that the surgical instruments may encompass medical devices which are used for exploratory purposes, testing purposes or other types of medical procedures. Additionally or alternatively, surgical instrument 12 may incorporate one or more localization elements 24 that are detectable by tracking subsystem 20. As illustrated in FIG. 10, surgical instrument 12 is connected by wire to tracking subsystem 20; in alternative embodiments, surgical instrument 12 may be wirelessly connected to tracking subsystem 20.

Imaging device 14 may be used to capture volumetric scan data (see box 32 of FIG. 2) representative of an internal region of interest within patient 13. The scan data, preferably three-dimensional data, may be obtained prior to and/or during surgery on patient 13 and stored in the memory component associated with processor 16. It should be understood that volumetric scan data may be acquired using various known medical imaging devices 14, including but not limited to a magnetic resonance imaging (MRI) device, a computed tomography (CT) imaging device, a positron emission tomography (PET) imaging device, a 2D or 3D fluoroscopic imaging device, and 2D, 3D or 4D ultrasound imaging devices. In the case of a two-dimensional ultrasound imaging device or other two-dimensional image acquisition device, a series of two-dimensional data sets may be acquired and then assembled into volumetric data as is well known in the art using a two-dimensional to three-dimensional conversion.

Dynamic reference frame 19 may be attached to patient 13 proximate to the region (tissue) of interest within the patient 13. For ease of illustration, dynamic reference frame 19 is attached to the forehead of patient 13 in FIG. 1; in an actual medical procedure, dynamic reference frame 19 may be located in a cavity, vessel or otherwise within patient 13. In one embodiment, dynamic reference frame 19 includes localization elements detectable by the tracking subsystem 20 to enable dynamic reference frame 19 to function as a point of reference for tracking subsystem 20 during the procedure as further described below.

Tracking subsystem 20 is also configured to track localization elements 24 associated with surgical instrument 12. In general, tracking subsystem 20 may comprise any tracking system typically employed in image guided surgery, including but not limited to an electromagnetic tracking system. An example of a suitable electromagnetic tracking subsystem is the AURORA electromagnetic tracking system, commercially available from Northern Digital Inc. in Waterloo, Ontario Canada. In one embodiment, tracking subsystem 20 is an electromagnetic tracking system, typically comprising an electromagnetic field generator 22 that emits a series of electromagnetic fields designed to engulf patient 13, and localization elements 24 coupled to surgical instrument 12 could be coils that would receive an induced voltage that could be monitored and translated into a coordinate position of localization elements 24. In certain embodiments, localization element 24 may be electrically coupled to twisted pair conductors to provide electromagnetic shielding of the conductors. This shielding prevents voltage induction along the conductors when exposed to the magnetic flux produced by the electromagnetic field generator. The twisted pair conductors extend from the localization element through surgical instrument 12.

Figure 2:
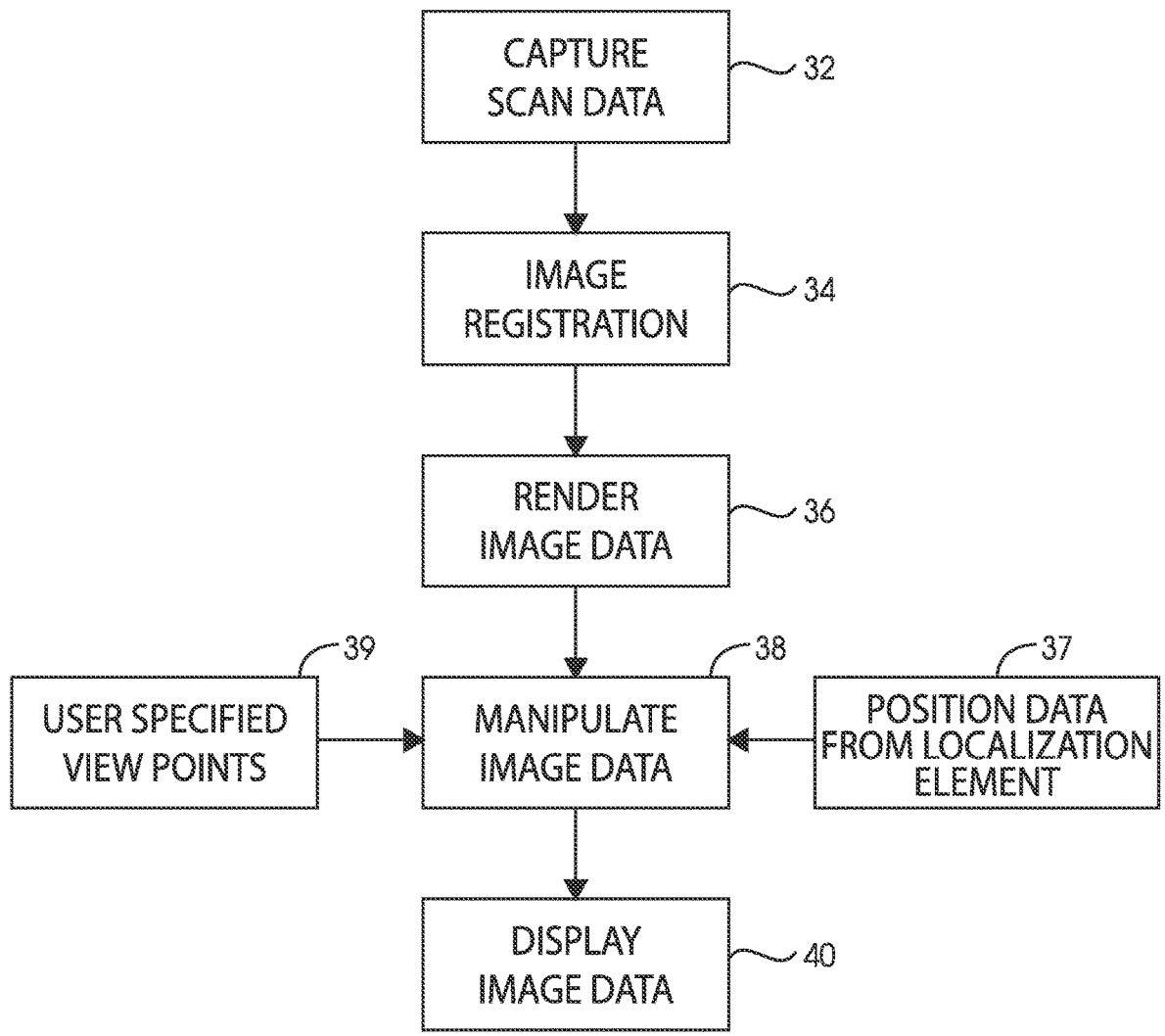
FIG. 2 is a flowchart that depicts a technique for simulating a virtual volumetric image of a body cavity from a point of view of a surgical instrument positioned within the patient according to an embodiment of the present invention.
Figure 3A:
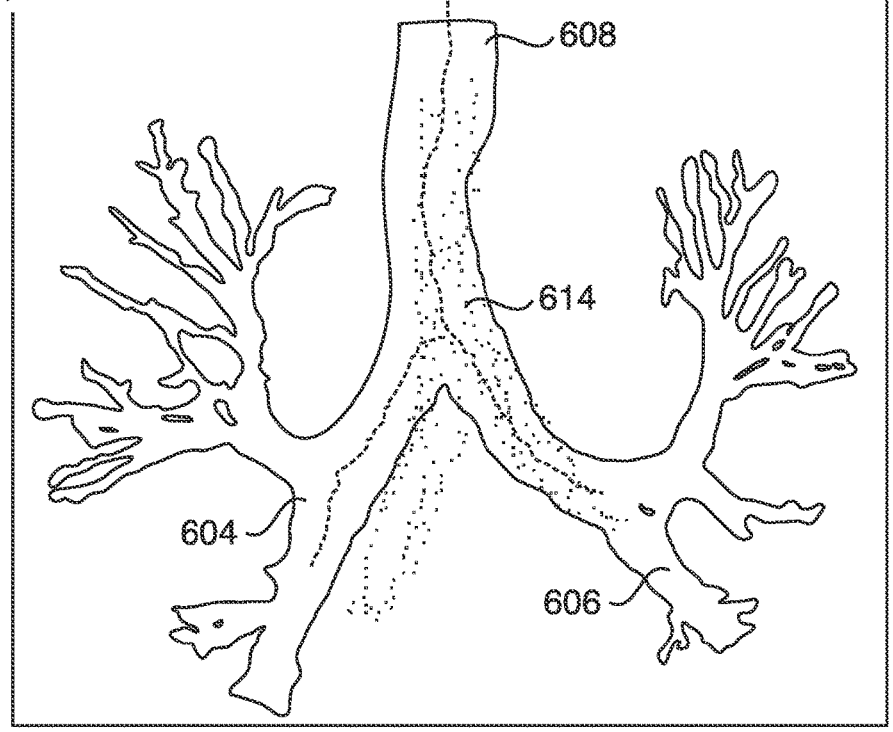
FIG. 3A is an illustration showing an initially collected respiratory-gated point cloud and FIG. 3B is an illustration showing a respiratory-gated point cloud registered to a patient's respiratory system according to an embodiment of the present invention.
Figure 3B:
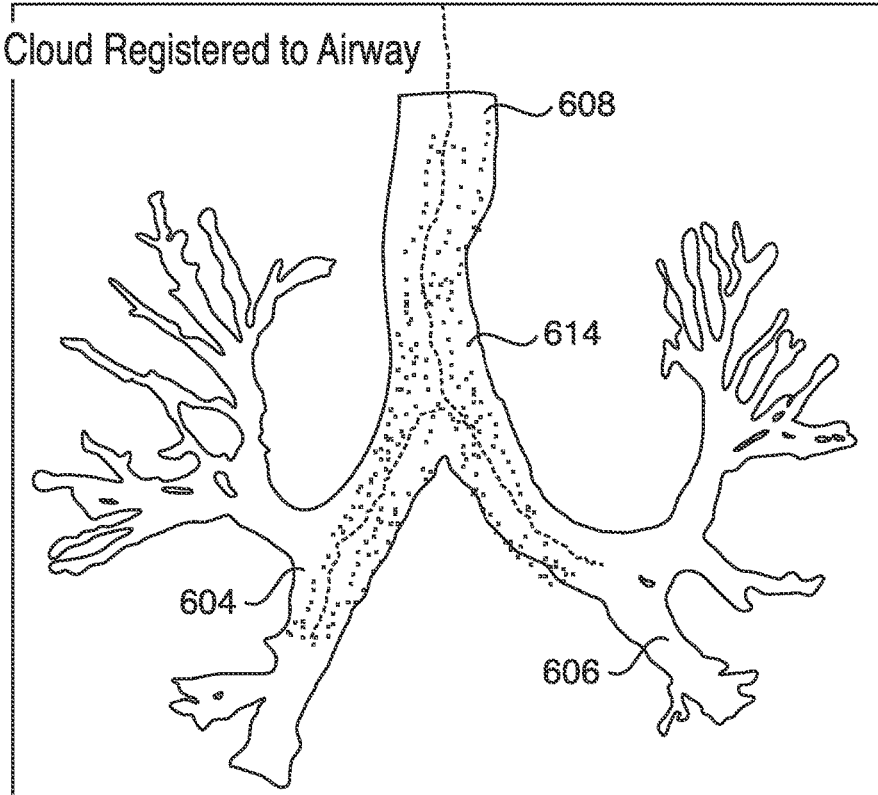

FIG. 2 illustrates a flowchart of a technique for simulating a virtual volumetric scene of a body cavity from a point of view of a surgical instrument positioned within the patient. Volumetric scan data captured by imaging device 14 (see box 32) may be registered to patient 13 (see box 34) using dynamic reference frame 19. This registration process is sometimes referred to as registering image space to patient space. Often, the volumetric scan data captured by imaging device 14 is also registered to other image datasets, typically an image dataset acquired at an earlier point time or an atlas. Registration of the image space to patient space is accomplished through knowledge of the coordinate vectors of at least three non-collinear points in the image space and the patient space. FIG. 3A, for example, illustrates an initially generated point cloud superimposed on a segmented image dataset of a patient's respiratory system and FIG. 3B illustrates a point cloud registered to a segmented image dataset of a patient's respiratory system.

Registration of image space to patient space for image guided surgery (see box 34 of FIG. 2) can be completed by different known techniques. Registration can be performed in multiple ways: point registration, pathway registration, 2D/3D image registration, etc. Such registration may be performed using 4D-gating information to track the patient's motion such as respiration and/or heartbeat. For example, point-to-point registration may be accomplished by identifying points in an image space and then touching the same points in patient space. These points are generally anatomical landmarks that are easily identifiable on the patient. By way of further example, surface registration involves the user's generation of a surface in patient space by either selecting multiple points or scanning, and then accepting the best fit to that surface in image space by iteratively calculating with the processor until a surface match is identified. By way of further example, repeat fixation devices entail the user repeatedly removing and replacing a device (i.e., dynamic reference frame, etc.) in known relation to the patient or image fiducials of the patient. By way of further example, automatic registration is accomplished by first attaching the dynamic reference frame to the patient prior to acquiring image data. It is envisioned that other known registration procedures are also within the scope of the present invention, such as that disclosed in U.S. Pat. No. 6,470,207, which is hereby incorporated by reference in its entirety. Once registration is complete the system can determine potential regions of the image dataset that may not match the patient's real-time anatomy. After image registration (see box 34 of FIG. 2) the image data may be rendered (see box 36 of FIG. 2) as a volumetric perspective image and/or a surface rendered image of the region of interest based on the scan data using rendering techniques well known in the art.

During surgery, surgical instrument 12 is directed by the physician or other healthcare professional to the region (or tissue) of interest within patient 13. Tracking subsystem 20 preferably employs electromagnetic sensing to capture position data (see box 37 of FIG. 2) indicative of the location and/or orientation of surgical instrument 12 within patient 13. Tracking subsystem 20 may be defined as an electromagnetic field generator 22 and one or more localization elements 24 (e.g., electromagnetic sensors) may be integrated into the items of interest, such as the surgical instrument 12. In one embodiment, electromagnetic field generator 22 may be comprised of three or more field generators (transmitters) mounted at known locations on a plane surface and localization elements (receivers) 24 are further defined as a single coil of wire. The positioning of the field generators (transmitter) and the localization elements (receivers) may also be reversed, such that the generators are associated with surgical instrument 12 and the receivers are positioned elsewhere. Although not limited thereto, electromagnetic field generator 22 may be affixed to an underneath side of the operating table that supports the patient.

In certain embodiments, localization element 24 comprises a six (6) degree of freedom (6DOF) electromagnetic sensor. In other embodiments, localization element 24 comprises a five (5) degree of freedom (5DOF) electromagnetic sensor. In other embodiments, localization element 24 comprises other localization devices such as radiopaque markers that are visible via fluoroscopic imaging and echogenic patterns that are visible via ultrasonic imaging. In yet other embodiments, localization elements 24 can be, for example, infrared light emitting diodes, and/or optical passive reflective markers. Localization elements 24 can also be, or be integrated with, one or more fiber optic localization (FDL) devices. In other embodiments surgical instrument 12 is non-navigated, such that it does not include any localization elements.

In operation, the field generators of localization device 22 generate magnetic fields which are detected by localization element 24. By measuring the magnetic field generated by each field generator at localization element 24, the location and orientation of localization element 24 may be computed, thereby determining position data for localization element 24 associated with surgical instrument 12. Although not limited thereto, exemplary electromagnetic tracking subsystems are further described in U.S. Pat. Nos. 5,913,820; 5,592,939; and 6,374,134 which are incorporated herein by reference in their entirety. In addition, it is envisioned that other types of position tracking devices are also within the scope of the present invention. For instance, tracking subsystem 20 may comprise a non-line-of-sight device based on sonic emissions or radio frequency emissions. In another instance, a rigid surgical instrument, such as a rigid endoscope may be tracked using a line-of-sight optical-based tracking subsystem (i.e., LED's, passive markers, reflective markers, etc.).

Position data for localization element 24, such as location and/or orientation data from the tracking subsystem 20 is in turn relayed to the processor 16. Processor 16 is adapted to receive position/orientation data (see box 37 of FIG. 2) from tracking subsystem 20 and the volumetric perspective and/or surface image data may be further manipulated (see box 38 of FIG. 2) based on the position/orientation data for surgical instrument 12 received from tracking subsystem 20. Specifically, the volumetric perspective or surface rendered image is rendered from a point of view which relates to position of the surgical instrument 12. For instance, at least one localization element 24 may be positioned at the distal end of surgical instrument 12, such that the image is rendered from a leading point on the surgical instrument. In this way, surgical instrument navigation system 10 of the present invention is able, for example, to visually simulate a virtual volumetric scene of an internal cavity from the point of view of surgical instrument 12 residing in the cavity without the use of an endoscope. It is readily understood that tracking two or more localization elements 24 which are embedded in surgical instrument 12 enables orientation of surgical instrument 12 to be determined by the system 10.

As surgical instrument 12 is moved by the physician or other healthcare professional within the region of interest, its position and orientation may be tracked and reported on a real-time basis by tracking subsystem 20. Referring again to FIG. 2, the volumetric perspective image may then be updated by manipulating (see box 38) the rendered image data (see box 36) based on the position of surgical instrument 12. The manipulated volumetric perspective image (see box 38) is displayed 40 as a primary image on a display device 18 associated with the processor 16. The display 18 is preferably located such that it can be easily viewed by the physician or other healthcare professional during the medical procedure. In one embodiment, the display 18 may be further defined as a heads-up display or any other appropriate display. The image may also be stored by processor 16 for later playback, should this be desired.

It is envisioned that the primary of the region of interest may be supplemented by other secondary images. For instance, known image processing techniques may be employed to generate various multi-planar images of the region of interest. Alternatively, images may be generated from different view points (see box 39) as specified by a physician or other healthcare professional, including views from outside of the vessel or cavity or views that enable the user to see through the walls of the vessel using different shading or opacity. In another instance, the location data of the surgical instrument may be saved and played back in a movie format. It is envisioned that these various secondary images may be displayed simultaneously with or in place of the primary perspective image.

In addition, surgical instrument 12 may be used to generate real-time maps corresponding to an internal path traveled by the surgical instrument or an external boundary of an internal cavity. Real-time maps may be generated by continuously recording the position of the instrument's localized tip and its full extent. A real-time map may be generated by the outermost extent of the instrument's position and minimum extrapolated curvature as is known in the art. The map may be continuously updated as the instrument is moved within the patient, thereby creating a path or a volume representing the internal boundary of the cavity. It is envisioned that the map may be displayed in a wire frame form, as a shaded surface or other three-dimensional computer display modality independent from or superimposed on the volumetric perspective image of the region of interest.

It is further envisioned that the map may include data collected from a localization element embedded into the surgical instrument, such as pressure data, temperature data or electro-physiological data. In this case, the map may be coded with a color or some other visual indicia to represent the collected data.

Figure 4:
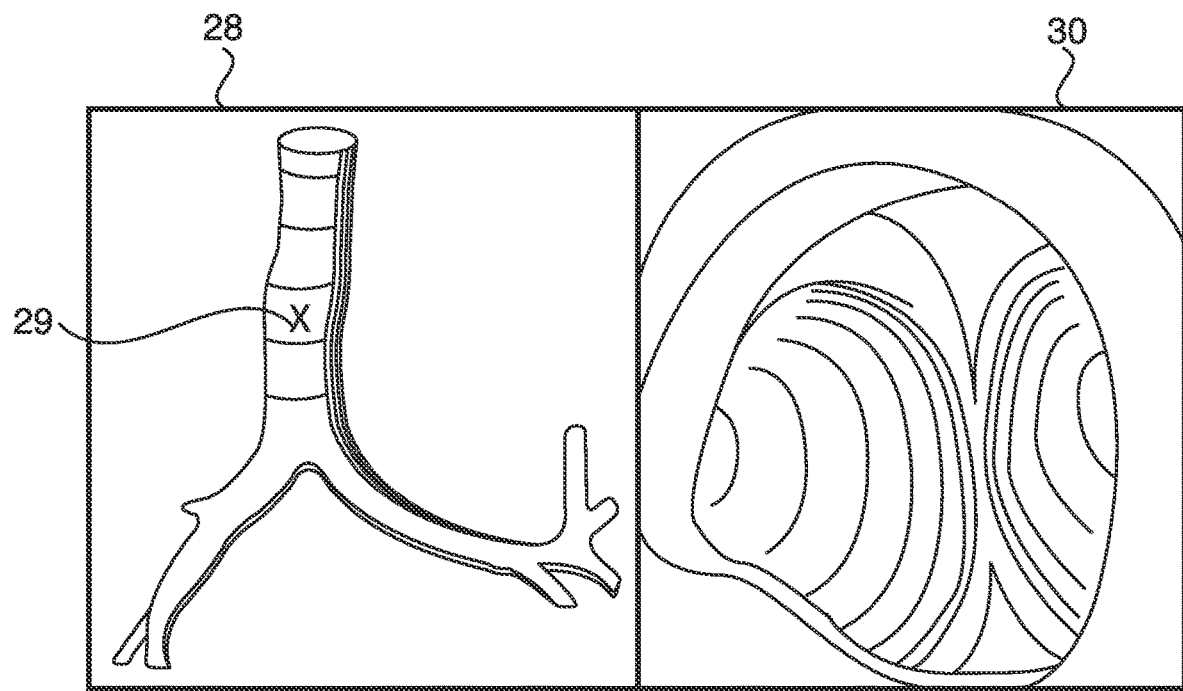
FIG. 4 is an exemplary display from the surgical instrument navigation system according to an embodiment of the present invention.

FIG. 4 illustrates another type of secondary image 28 which may be displayed in conjunction with the primary perspective image 30. In this instance, primary perspective image 30 is an interior view of an air passage within patient 13. Secondary image 28 is an exterior view of the air passage which includes an indicia or graphical representation 29 that corresponds to the location of surgical instrument 12 within the air passage. In FIG. 4, indicia 29 is shown as a crosshairs. It is envisioned that other indicia may be used to signify the location of the surgical instrument in the secondary image. As further described below, secondary image 28 may be constructed by superimposing indicia 29 of surgical instrument 12 onto the manipulated image data 38.

The displayed indicia 29 of surgical instrument 12 tracks the movement of surgical instrument 12 as it is moved by the physician or other healthcare professional within patient 13. In certain instances, the cardiac or respiration cycle of the patient may cause surgical instrument 12 to flutter or jitter within the patient. For instance, a surgical instrument 12 positioned in or near a chamber of the heart will move in relation to the patient's heart beat. In this instance, the indicia of the surgical instrument 12 will likewise flutter or jitter on the displayed image (see box 40 of FIG. 2). It is envisioned that other anatomical functions which may affect the position of the surgical instrument 12 within the patient are also within the scope of the present invention. Rather than display indicia 29 of surgical instrument 12 on a real-time basis, the display of indicia 29 of surgical instrument 12 is periodically updated based on a timing signal from timing signal generator 26. In one exemplary embodiment, the timing signal generator 26 is electrically connected to tracking subsystem 20.

Figure 5:
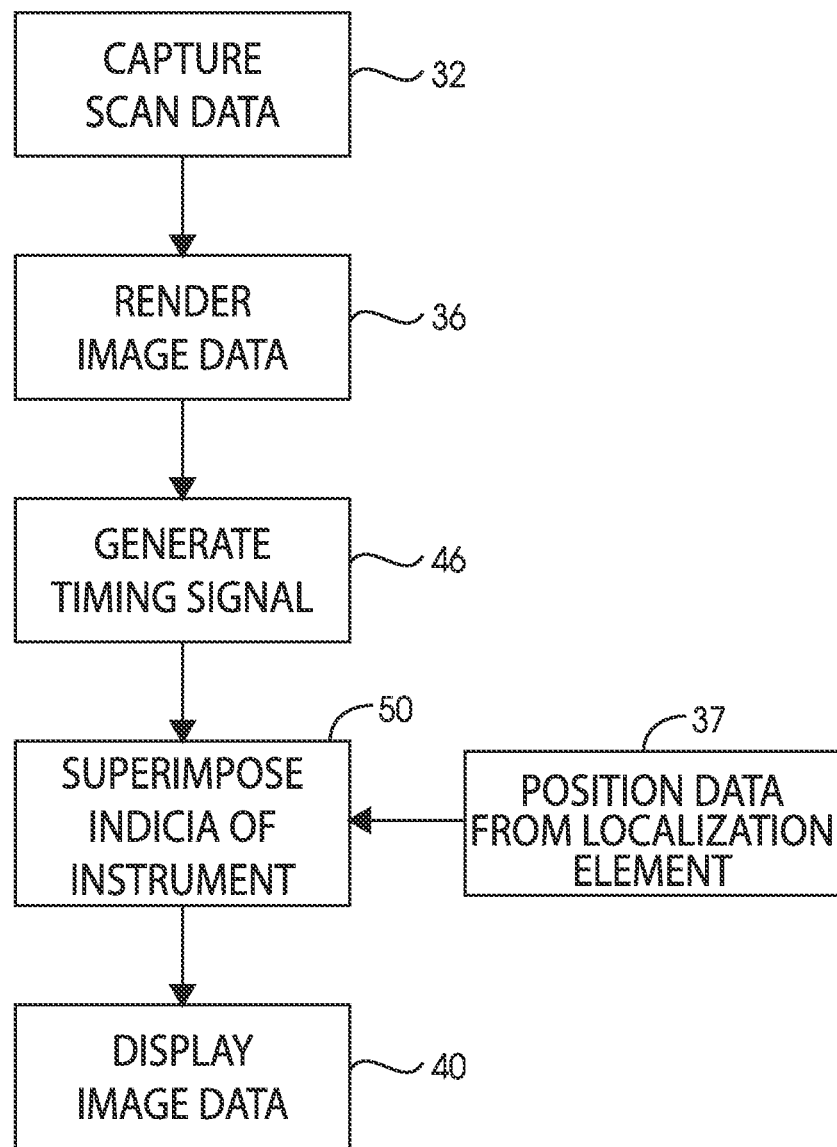
FIG. 5 is a flowchart that depicts a technique for synchronizing the display of an indicia or graphical representation of the surgical instrument with the cardiac or respiration cycle of the patient according to an embodiment of the present invention.

As shown by the flowchart of FIG. 5, another embodiment may be a technique for synchronizing the display of an indicia or graphical representation of surgical instrument 12 with cardiac or respiration cycle of the patient in order to reduce flutter. The display of an indicia of surgical instrument 12 may be synchronized with an anatomical function, such as the cardiac or respiration cycle of the patient. As described above, imaging device 14 may be used to capture (see box 32 of FIG. 5) volumetric scan data representative of an internal region of interest within a given patient. An may then be rendered (see box 36 of FIG. 5) from the volumetric scan data by processor 16. A timing signal generator 26 (not shown) may be operable to generate and transmit a timing signal (see box 46 of FIG. 5) that correlates to at least one of (or both) the cardiac cycle or the respiration cycle of patient 13. For a patient having a consistent rhythmic cycle, the timing signal might be in the form of a periodic clock signal. Alternatively, the timing signal may be derived from an electrocardiogram signal from the patient 13. One skilled in the art will readily recognize other techniques for deriving a timing signal that correlate to at least one of the cardiac or respiration cycle or other anatomical cycle of the patient. The acquisition of position data (see box 37 of FIG. 5) for surgical instrument 12 may then be synchronized to the timing signal.

Tracking subsystem 20 is, in turn, operable to report position data (see box 37 of FIG. 5) for surgical instrument 12 in response to a generated timing signal (see box 46 of FIG. 5) received from timing signal generator 26. The position of indicia 29 of surgical instrument 12 may then be updated and superimposed (see box 50 of FIG. 5) on the display of the image data (see box 40 of FIG. 5). It is readily understood that other techniques for synchronizing the display of indicia 29 of surgical instrument 12 based on the timing signal are within the scope of the present invention, thereby eliminating any flutter or jitter which may appear on the displayed image (see box 40 of FIG. 5). It is also envisioned that a path (or projected path) of surgical instrument 12 may also be illustrated on displayed image data (see box 40 of FIG. 5).

Figure 6:
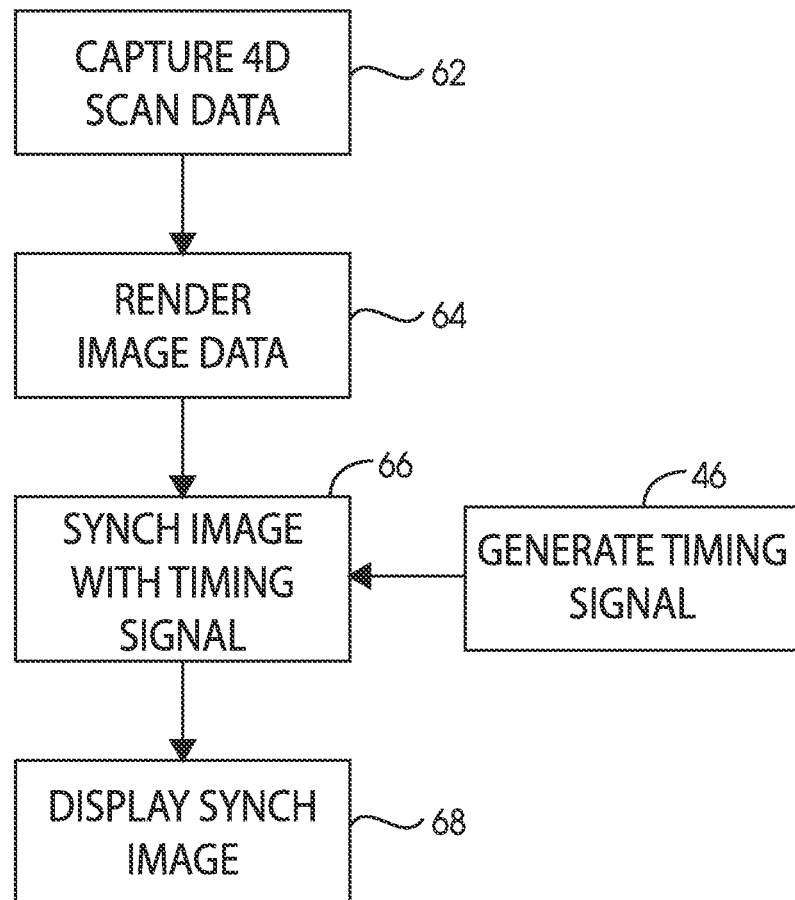
FIG. 6 is a flowchart that depicts a technique for generating four-dimensional image data that is synchronized with the patient according to an embodiment of the present invention.

In another aspect of the present invention, surgical instrument navigation system 10 may be further adapted to display four-dimensional image data for a region of interest as shown in the flowchart of FIG. 6. In this case, imaging device 14 is operable to capture 4D volumetric scan data (see box 62) for an internal region of interest over a period of time, such that the region of interest includes motion that is caused by either the cardiac cycle or the respiration cycle of patient 13. A volumetric perspective image of the region may be rendered (see box 64) from the captured 4D volumetric scan data (see box 62) by processor 16 as described above. The four-dimensional image data may be further supplemented with other patient data, such as temperature or blood pressure, using a color code or some other visual indicia.

The display of the volumetric perspective image may be synchronized (see box 66) in real-time with the cardiac or respiration cycle of patient 13 by adapting processor 16 to receive a generated timing signal (see box 46) from timing signal generator 26. As described above, the timing signal generator 26 is operable to generate and transmit a timing signal that correlates to either the cardiac cycle or the respiration cycle of patient 13. In this way, the 4D volumetric perspective image may be synchronized (see box 66) with the cardiac or respiration cycle of patient 13. The synchronized image is then displayed (see box 68) on the display 18 of the system. The four-dimensional synchronized image may be either (or both of) the primary image rendered from the point of view of the surgical instrument or the secondary image depicting the indicia of the position of surgical instrument 12 within patient 13. It is readily understood that the synchronization process is also applicable to two-dimensional image data acquire over time.

To enhance visualization and refine accuracy of the displayed image data, the surgical navigation system can use prior knowledge such as a segmented vessel or airway structure to compensate for error in the tracking subsystem or for inaccuracies caused by an anatomical shift occurring since acquisition of scan data. For instance, it is known that surgical instrument 12 being localized is located within a given vessel or airway and, therefore may be displayed within the vessel or airway. Statistical methods can be used to determine the most likely location; within the vessel or airway with respect to the reported location and then compensate so the display accurately represents surgical instrument 12 within the center of the vessel or airway. The center of the vessel or airway can be found by segmenting the vessels or airways from the three-dimensional datasets and using commonly known imaging techniques to define the centerline of the vessel or airway tree. Statistical methods may also be used to determine if surgical instrument 12 has potentially punctured the vessel or airway. This can be done by determining the reported location is too far from the centerline or the trajectory of the path traveled is greater than a certain angle (worse case 90 degrees) with respect to the vessel or airway. Reporting this type of trajectory (error) may be desired by the physicians or other healthcare professionals. The tracking along the center of the vessel or airway may also be further refined by correcting for motion of the respiratory or cardiac cycle, as described above. While navigating along the vessel or airway tree, prior knowledge about the last known location can be used to aid in determining the new location. Surgical instrument 12 or other navigated device follows a pre-defined vessel or airway tree and therefore cannot jump from one branch to the other without traveling along a path that would be allowed. The orientation of surgical instrument 12 or other navigated device can also be used to select the most likely pathway that is being traversed. The orientation information can be used to increase the probability or weight for selected location or to exclude potential pathways and therefore enhance system accuracy.

Surgical instrument navigation system 10 of the present invention may also incorporate atlas maps. It is envisioned that three-dimensional or four-dimensional atlas maps may be registered with patient specific scan data or generic anatomical models. Atlas maps may contain kinematic information (e.g., heart models) that can be synchronized with four-dimensional image data, thereby supplementing the real-time information. In addition, the kinematic information may be combined with localization information from several instruments to provide a complete four-dimensional model of organ motion. The atlas maps may also be used to localize bones or soft tissue which can assist in determining placement and location of implants.

In general, a consistent feature between lung scans is the existence of an airway tree within the lung tissue, consisting of multiple branches and carinas. The branches and carinas, however, move as a consequence of a patient's respiration. To provide more accurate navigation of an instrument through the airway tree of a patient, a set of data points may be collected from a patient pathway (e.g., an airway) and a model of points may be calculated to match the image dataset. In one embodiment, each discrete segment of the image dataset and its corresponding information are matched to the collected points, creating a "point cloud" of information. Then, the data points that create the outer region or shell of the point cloud are determined, followed by correlation or matching of the outer points to the patient's 3D image data sets.

A respiratory-gated point cloud comprises a plurality of data points corresponding to the internal volume of a patient's respiratory system measured by a localization element during the respiration cycle of a patient. Each data point of the respiratory-gated point cloud comprises three dimensional data (x, y, and z location) in reference to a 3D coordinate system. In this embodiment, each data point of the respiratory-gated point cloud may be gated to the respiration cycle of the patient. The respiratory-gated point cloud also comprises a fourth dimension representing the phase (inspiration, expiration, and, if desired, points in between) of the respiration cycle of the patient at which point the individual data point was generated. The phase information may be provided by a patient tracker that real-time tracks the patient's respiratory cycle. In certain embodiments, the generation of the individual data points in the point cloud may occur on a time-gated basis triggered by a physiological signal of the patient's respiration cycle. In other embodiments, a respiratory-gated point cloud can be collected at inspiration and another respiratory-gated point cloud collected at expiration. These two respiratory-gated point clouds can then be matched to an image dataset to assist registration. Alternatively, a single respiratory-gated point cloud can be collected including data points from both inspiration and expiration and matched to an image dataset.

Figure 7:
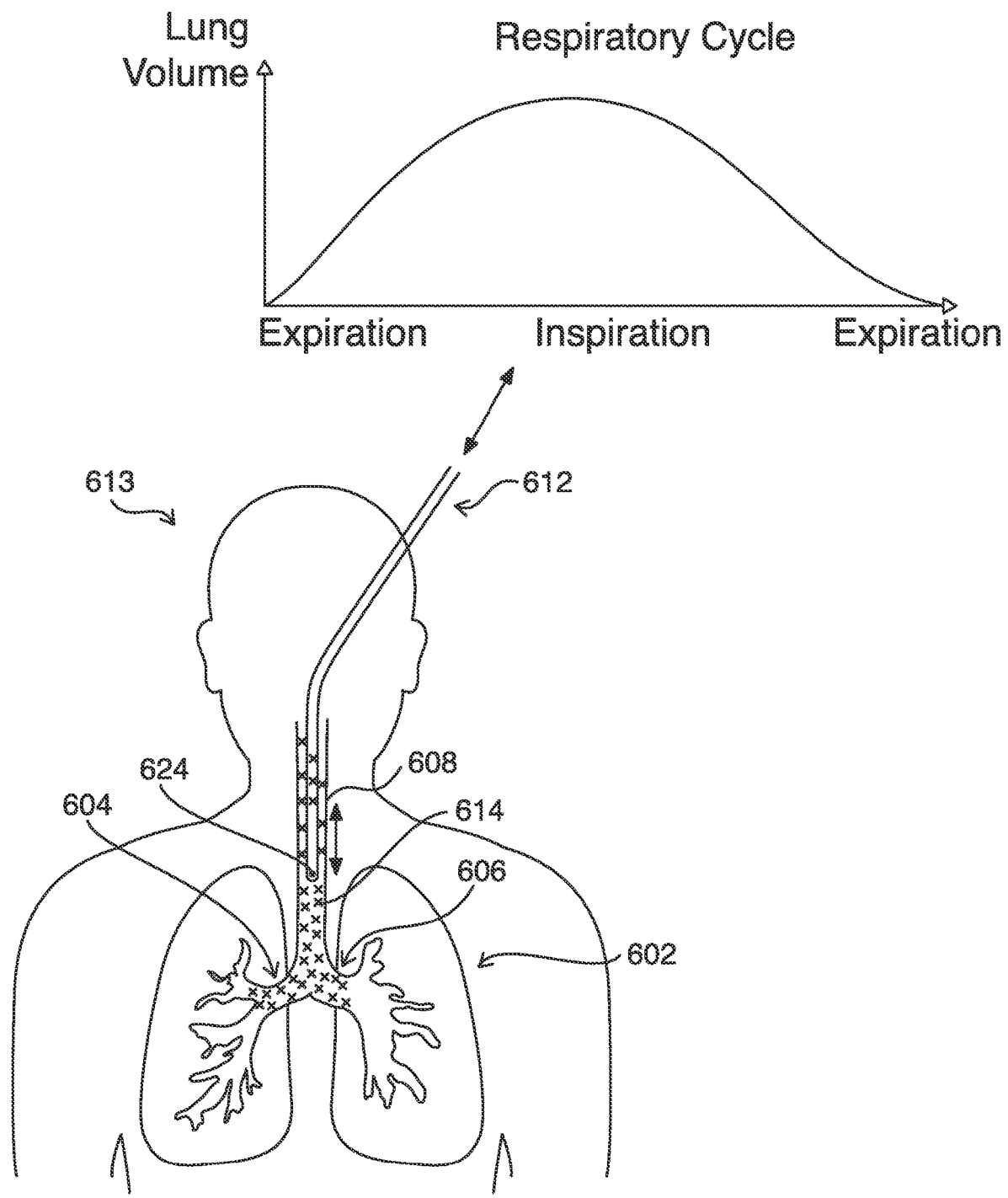
FIG. 7 is a front view of a patient during the generation of a respiratory-gated point cloud in the respiratory system of a patient using a catheter and a top panel illustrating that the respiratory-gated point cloud may be taken over the entire respiratory cycle of the patient according to an embodiment of the present invention.

Referring now to FIG. 7, a respiratory-gated point cloud can be collected in one embodiment using a surgical instrument navigation system 10 (not shown) comprising catheter 612 having localization element 624 at the distal end thereof. More specifically, a physician or other healthcare professional moves catheter 612 through a plurality of locations 614 within the branches of a patient's respiratory system 602, including trachea 608, right main bronchus (RMB) 604, and left main bronchus (LMB) 606 over a full respiration cycle of patient 613 to form respiratory-gated point cloud corresponding to position/orientation data of localization element 624. According to one particular embodiment, a respiratory signal is used to gate the localization information. Additionally or alternatively, the respiratory signal can be derived, for example, using a device that records the resistance between two locations on the patient; such a method is similar to a variable potentiometer in that the resistance of the patient changes between two fixed points as the patient inhales and exhales. Thus, the resistance can be measured to create a respiratory signal. When a signal indicating a particular phase of the respiration cycle is received, the processor begins acquiring valid position/orientation data regarding the localization element(s) 624 in catheter 612 through a plurality of locations 614 within the branches of a patient's respiratory system 602, thereby generating respiratory-gated point cloud. Once the respiration cycle moves outside of that phase, a stop signal halts the point cloud data collection. In this way, it is not necessary to track the motion of the patient's anatomy if the respiratory motion is the only motion occurring.

Density filtering of the generated respiratory-gated point clouds can reduce the number of duplicate data points generated which can significantly decrease the processing time. Depending on the desired strength of filtering, a duplicate data point in the respiratory-gated point is defined as having identical three dimensional coordinates (x, y, and z) to another data point in the respiratory-gated point cloud wherein both points were generated in the same respiratory phase or a duplicate data point in the respiratory-gated point is defined as having three dimensional coordinates x1, y1, and z1 within a certain distance to another data point in the respiratory-gated point cloud having three dimensional coordinates x2, y2, and z2 wherein both points were generated in the same respiratory phase. This duplicated data point, and any additional duplicate data points can be eliminated, leaving only one data point for each three dimensional coordinate and corresponding respiratory phase. In another embodiment, additional density filtering can be done by eliminating duplicate data points without reference to a given respiratory phase. This would eliminate duplicate data points from the respiratory-gated point cloud that were generated throughout multiple phases. By eliminating the duplicate data points, a processor need not perform subsequent calculations of unnecessary data points.

Additionally, in certain embodiments, the generated point cloud may be compared to the segmented image data to determine the strength or weighting of each point collected in the point cloud. Calculating the strength or weighting of discrete points in the point cloud can enhance registration accuracy. By way of example, collecting a single string of points that are only 1 mm wide to represent an airway that is 5-6 mm wide as determined in the image model would be an insufficient point cloud. Feedback can be provided to the user such as color coding or some other visual indicia to identify the strength of the point cloud.

In one exemplary embodiment, a physician or other healthcare professional captures a respiratory-gated point cloud and the captured cloud is density filtered as previously described to form a density-filtered point cloud comprising unclassified point cloud data points. The density-filtered point cloud may then be classified using a first k-means algorithm which performs orientation classification resulting in the data points in the respiratory-gated point cloud being classified into the trachea, the right main bronchus and the left main bronchus. A second k-means algorithm is performed to further classify the data points in the respiratory-gated point cloud into control points. The respiratory-gated point cloud may then be registered to a pre-existing image dataset and the data points of the respiratory-gated point cloud are weighted. Each data point in the respiratory-gated point cloud may then be displayed to the user with a color code or some other visual indicia corresponding to the calculated weight for each data point in the respiratory-gated point cloud. In certain embodiments, feedback may be provided to the physician or other healthcare professional indicating that additional respiratory-gated point cloud data points may be collected in locations having lesser weighting. This method may then be repeated until a desired weighting is achieved across the respiratory-gated point cloud.

Image datasets may not perfectly match if the image data was acquired at a different phase in the respiration cycle (e.g., full inspiration, partial inspiration, full expiration, etc.) or if the patient's anatomy has been changed due to positioning on the table, weight gain/loss, skin shift, delivery of drugs, etc. In such embodiments, an image dataset taken at a first time point can be modified or deformed to better correspond to the respiratory-gated point cloud generated during the medical procedure (i.e., a second and subsequent time point). Additionally, a sequence of motion of the respiratory-gated point cloud can be generated over the complete procedure or significant period of time. The distance, range, acceleration, and speed between one or more selected pairs of respiratory-gated data points within the point cloud generated by the localization element 624 (see FIG. 7) can be determined and various algorithms can be used to analyze and compare the distance between selected data points at given instants in time.

Figure 8:
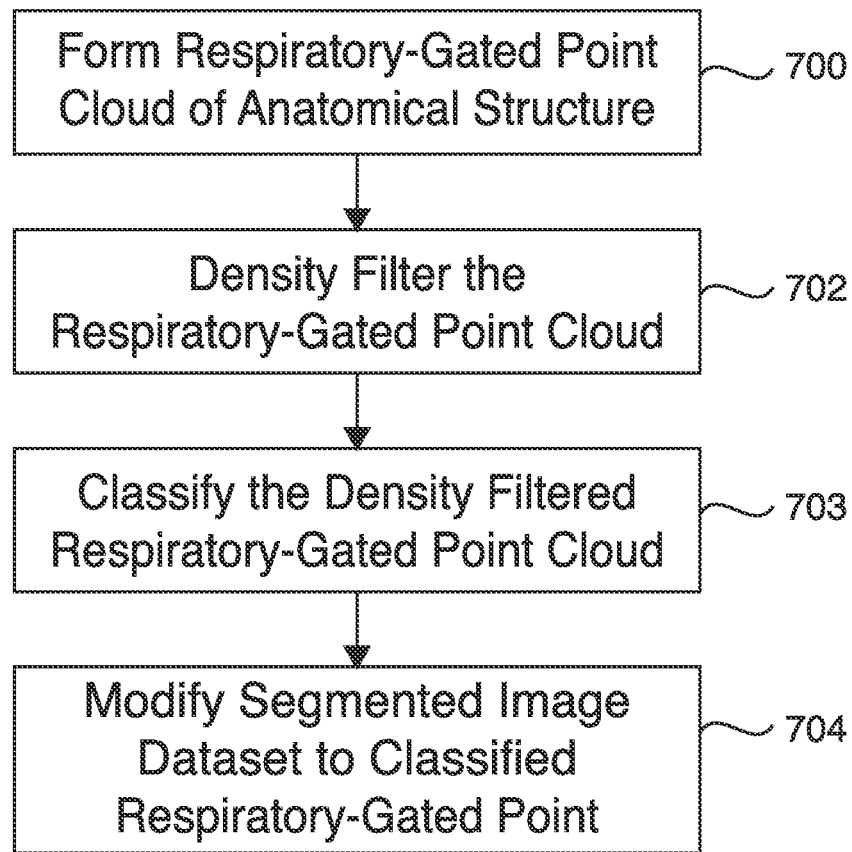
FIG. 8 is a flow chart depicting the deformation of a segmented image dataset to a respiratory-gated point cloud according to an embodiment of the present invention.

Referring now to FIG. 8, a method for modifying or deforming a segmented image dataset for a region of a respiratory system of a patient to the corresponding anatomy of a patient's respiratory system in one embodiment comprises forming (see box 700) a respiratory-gated point cloud of data that demarcates anatomical features in a region of a patient's respiratory system at one or more discrete phases within a respiration cycle of a patient. The respiratory-gated point cloud is then density filtered (see box 702). The density filtered point cloud is then classified (see box 703) according to anatomical points of reference in a segmented image dataset for the region of the patient's respiratory system (as described above), and a segmented image dataset for the region of the respiratory system is modified (or deformed) (see box 704) using a deformation vector field to correspond to the classified anatomical points of reference in the density filtered respiratory-gated point cloud. In certain embodiments, the phases at which the respiratory-gated point cloud is formed include inspiration, expiration and phases in between.

A deformation vector field can be calculated between a first set of points in the respiratory-gated point cloud that correspond to inspiration and a second set of points in the respiratory-gated point cloud that correspond to expiration. This deformation vector field may then be used to modify or deform a pre-existing or pre-acquired segmented image dataset, taken from a first time interval, to correspond to the correlated anatomical points of reference in the respiratory-gated point cloud, taken during a second time interval. In certain embodiments, the segmented image dataset to be modified is from a first discrete phase of the patient's respiration cycle and the respiratory-gated point cloud is from a second and different discrete phase of the patient's respiration cycle. Accordingly, a pre-existing or pre-acquired segmented image dataset can be from an inspiration phase and it can be modified or deformed to the expiration phase using the deformation vector field calculated from the respiratory-gated point cloud. Thus a segmented image dataset need not require an image for each phase of the patient's respiration cycle.

A deformation vector field can be calculated between data points in the respiratory-gated point cloud that correspond to different phases of the patient's respiratory cycle. The image dataset from a first time interval may then be modified or deformed by the deformation vector field to match the anatomy of the patient during the second time interval. This modification or deformation process can be done continuously during the medical procedure, producing simulated real-time, intra-procedural images illustrating the orientation and shape of the targeted anatomy as a catheter, sheath, needle, forceps, guidewire, fiducial delivery devices, therapy device (ablation modeling, drug diffusion modeling, etc.), or similar structure(s) is/are navigated to the targeted anatomy. Thus, during the medical procedure, the physician or other healthcare professional can view selected modified or deformed image(s) of the targeted anatomy that correspond to and simulate real-time movement of the anatomy. In addition, during a medical procedure being performed during the second time interval, such as navigating a catheter or other instrument or component thereof to a targeted anatomy, the location(s) of a localization element (e.g., an electromagnetic coil sensor) coupled to the catheter during the second time interval can be superimposed on an image of a catheter. The superimposed image(s) of the catheter can then be superimposed on the modified or deformed image(s) from the first time interval, providing simulated real-time images of the catheter location relative to the targeted anatomy. This process and other related methods are described in U.S. Pat. No. 7,398,116, the entire disclosure of which is incorporated herein by reference.

The deformation vector field may be calculated between a first set of points in the respiratory-gated point cloud that correspond to a first respiration phase and a second set of points in the respiratory-gated point cloud that correspond to a second respiration phase. Typically, the first respiration phase is inspiration and the second respiration phase is expiration. Additionally, the two phases can be reversed wherein the first phase is expiration and the second phase is inspiration. For example, the deformation vector field can be applied to modify or deform an image dataset of 3D fluoroscopic images or CT images in order to compensate for different patient orientations, patient position, respiration, deformation induced by the catheter or other instrument, and/or other changes or perturbations that occur due to therapy delivery or resection or ablation of tissue.

In some embodiments, for example, real-time respiration compensation can be determined by applying an inspiration-to-expiration deformation vector field. In combination with the respiratory signal, for example, the surgical instrument location can be calculated using the deformation vector field. A real-time surgical instrument tip correction vector can be applied to a 3D localized instrument tip. The real-time correction vector is computed by scaling an inspiration-to-expiration deformation vector (found from the inspiration-to-expiration deformation vector field) based on the respiratory-gated point cloud. This correction vector can then be applied to the 3D localized surgical instrument tip. This can further optimize accuracy during navigation.

An example of an algorithm for real-time respiration compensation can be found in FIG. 9. In accordance with this algorithm, for each 3D localized point $\ell$:

(a) find $v_i$ such that scalar d is minimized;
(b) compute c, wherein:

$$c = -v_i t$$

and (c) compute $\ell'$, wherein:

$$\ell' = \ell + c$$

Thus, $\ell'$ is a respiration compensated version of $\ell$.

Although FIG. 9 and the above discussion generally relate to real-time respiration motion, it will be understood that these calculations and determinations may also be applied to real-time heartbeat and/or vessel motion compensation, or any other motion of a dynamic body (e.g., the patient's body, an organ, or tissue thereof) as described herein. In one embodiment, for example, the deformation vector field is calculated based upon inspiration and expiration. In another embodiment, for example, the deformation vector field is calculated based upon heartbeat. In yet another embodiment, for example, the deformation vector field is based upon vessel motion. In these and other embodiments, it is also possible to extend these calculations and determinations to develop multiple deformation vector fields across multiple patient datasets, by acquiring the multiple datasets over the course of, for example, a single heartbeat cycle or a single respiration cycle.

Deformation of 2D images can also be calculated based upon therapeutic change of tissue, changes in Hounsfield units for images, patient motion compensation during the imaging sequence, therapy monitoring, and temperature monitoring with fluoroscopic imaging, among other things. One potential issue with conventional therapy delivery, for instance, is monitoring the therapy for temperature or tissue changes. In accordance with the methods described herein, this monitoring can be carried out using intermittent fluoroscopic imaging, where the images are compensated between acquisition times to show very small changes in image density, which can represent temperature changes or tissue changes as a result of the therapy and/or navigation.

Another method to modify/deform the image dataset and match to the patient is to segment the airway from the image dataset and skeletonize it to find the central airway tree. The physician or other healthcare professional can then modify/deform the image dataset by identifying points within the image space and patient space that match such as the main carina and/or collect multiple branch information that defines branches and carina points between branches. These points can be used to modify or deform the image dataset. Deformation of a complete 3D volume would be time consuming so methods to create deformation matrices for regions may be preferred.

In general, the embodiments described herein have applicability in "Inspiration to Expiration"-type CT scan fusion. According to various methods, the user navigates on the expiration CT scan to aid accuracy, while using the inspiration scan to aid airway segmentation. In one embodiment, for example, a user could complete planning and pathway segmentation on an inspiration scan of the patient. Preferably, a deformation vector field is created between at least two datasets. The deformation vector field may then be applied to the segmented vessels and/or airways and the user's planned path and target. In these and other embodiments, the deformation vector field can also be applied to multiple datasets or in a progressive way to create a moving underlying dataset that matches the patient's respiratory or cardiac motion. In other embodiments, using a respiratory-gated point cloud, a deformation vector field is calculated between a first set of points in the respiratory-gated point cloud that correspond to inspiration and a second set of points in the respiratory-gated point cloud that correspond to expiration. This deformation vector field may then used to modify or deform a pre-existing or pre-acquired segmented image dataset to correspond to the correlated anatomical points of reference in the respiratory-gated point cloud.

In accordance with various embodiments, "Inspiration to Expiration" CT fusion using the lung lobe centroid and vector change to modify an airway model may be used to translate and scale each airway based on the lung lobe change between scans. The lung is constructed of multiple lobes and these lobes are commonly analyzed for volume, shape, and translation change. Each lobe changes in a very different way during the patient's respiration cycle. Using this information to scale and translate the airways that are located in each lobe, it is possible to adapt for airway movement. This scaled airway model can then be linked to the 4D tracking of the patient as described herein. In accordance with various embodiments using a respiratory-gated point cloud, this technique may be used to translate and scale each airway based on the lung lobe change between respiration phases. The lung is constructed of multiple lobes and these lobes are commonly analyzed for volume, shape, and translation change. Each lobe changes in a very different way during the patient's respiration cycle. Using the respiratory-gated point cloud information to scale and translate the airways that are located in each lobe, it is possible to adapt for airway movement. This scaled airway model can then be linked to the 4D tracking of the patient as described herein.

In general, it may also be preferable to reduce the level of radiation that patients are exposed to before or during a procedure (or pre-procedural analysis) as described herein. One method of reducing radiation during the acquisition of a 3D fluoroscopic dataset (or other dataset described herein), for example, is to use a deformation vector field between data points in a respiratory-gated point cloud to reduce the actual number of 2D images that need to be acquired to create the 3D dataset. In one particular embodiment, the deformation field is used to calculate the deformation between images in the acquisition sequence to produce 2D images between the acquired slices, and these new slices can be used to calculate the 3D fluoroscopic dataset. For example, if 180 2D image slices were previously required, e.g., an image(s) taken every 2 degrees of a 360 degree acquisition sequence, in accordance with some embodiments 90 2D images can be acquired over a 360 degree acquisition sequence and the data from the images that would have ordinarily been acquired between each slice can be calculated and imported into the 3D reconstruction algorithm. Thus, the radiation is effectively reduced by 50%.

In another embodiment, illustrated by FIG. 10, a process of registration and deformation may assist the navigation of a surgical instrument. One method of preparing a segmented image dataset to match the anatomy of a patient's respiratory system comprises the steps of (i) forming (see box 700) a respiratory-gated point cloud of data that demarcates anatomical features in a region of a patient's respiratory system at one or more discrete phases within a respiration cycle of a patient, (ii) density filtering (see box 702) the respiratory-gated point cloud, (iii) classifying (see box 703) the density filtered respiratory-gated point cloud according to anatomical points of reference in a segmented image dataset for the region of the patient's respiratory system, (iii) registering (see box 800) the classified respiratory-gated point cloud to the segmented image dataset, (iv) comparing (see box 802) the registered respiratory-gated point cloud to a segmented image dataset to determine the weighting of points comprised by the classified respiratory-gated point cloud, (v) distinguishing (see box 804) regions of greater weighting from regions of lesser weighting and optionally increasing the data set comprised by the registered respiratory-gated point cloud for regions of lesser weighting, and (vi) modifying or deforming (see box 704) the segmented image dataset to correspond to the classified respiratory-gated point cloud. In alternative embodiments, the user may optionally perform a loop 806 and generate additional data points in the respiratory-gated point cloud to increase the weighting of certain points in the respiratory-gated point cloud. In certain embodiments, the phases at which the respiratory-gated point cloud is formed include inspiration, expiration and phases in between.

In addition to modifying or deforming the segmented image dataset, in one embodiment of the present invention the movement of a patient's respiratory system in the patient's respiration cycle over the patient's entire respiration cycle may be simulated in a method comprising (i) forming (see box 700 of FIG. 10) a respiratory-gated point cloud of data that demarcates anatomical features in a region of a patient's respiratory system at one or more discrete phases within a respiration cycle of a patient, (ii) density filtering (see box 702 of FIG. 10) the respiratory-gated point cloud, (iii) classifying (see box 703 of FIG. 10) the density filtered respiratory-gated point cloud according to anatomical points of reference in a segmented image dataset for the region of the patient's respiratory system, (iv) creating a cine loop comprising a plurality of modified segmented image datasets through multiple modifications of the segmented image dataset to correspond to a plurality of classified anatomical points of reference in the respiratory-gated point cloud over the respiration cycle, and (v) displaying the cine loop comprising the plurality of modified segmented image datasets over the patient's respiration cycle. In certain embodiments, the phases at which the respiratory-gated point cloud is formed include inspiration, expiration and phases in between. In certain embodiments, the plurality of modified segmented image datasets may be created by modifying a segmented image dataset according to the deformation vector field. In yet other embodiments, this simulated movement of the patient's respiratory system can be synchronized with the patient's respiration cycle. Accordingly, the gating information from the respiratory-gated point cloud is matched to a real-time gating signal corresponding to the patient's respiration cycle. The physician can then observe the modified or deformed image during the medical procedure on a targeted portion of the patient's body. Thus, during the medical procedure, the above simulation process can be continuously executed such that multiple modified images are displayed and modified images corresponding to real-time positions of the patient's body can be viewed. In certain embodiments, the plurality of modified segmented image datasets comprises 2 or more segmented image datasets. In other embodiments, the plurality of modified segmented image datasets comprises 3 or more segmented image datasets. In yet other embodiments, the plurality of modified segmented image datasets comprises 4 or more segmented image datasets. In certain embodiments, the creation and display of the cine loop comprising the plurality of modified segmented image datasets can be over the patient's entire respiratory cycle.

In another aspect, the system involves generating a respiratory-gated point cloud of a dynamic anatomy using implanted localization elements. In general, one or more (and typically multiple, e.g., 2, 3, 4, or more) localization elements may be placed in the organ and tracked continuously and registered to a discrete section of the organ. In this embodiment, the localization elements may have a pigtail or anchoring mechanism that allows it to be attached to an internal organ or along a vessel. Using image processing techniques, voxels from an image dataset, or set of voxels from an image dataset; multiple 3D data sets of the organ can be used to create discrete sections of the organ (i.e., in a grid-like pattern). For each section, a deformation vector field analysis can be performed between the phases of the organ and/or based upon the motion of the organ tracked by localization elements attached to or adjacent to a wall of the organ such that the motion of the organ is translated to the sensors. Each section will then have unique signature or deformation vector field, which can be matched to the tracked motion of the localization element(s) attached to the organ. For example, the wall localization element motion will match the space-time signature of the device. Preferably, a deformation vector field is created between at least two datasets. The deformation vector field may then be applied to the segmented vessels and/or airways and the user's planned path and target.

Another technique for maximizing registration accuracy is a centroid finding algorithm that can be used for refining point locations in a local area. Often, a user will want to select a vessel bifurcation. The vessel bifurcation will be seen as a bright white location on the CT and US images. An algorithm can be used to help the user select the center location for these locations. Once a user selects a point on the image, the local algorithm can be employed to find similar white voxels that are connected and, for that shape in the 3D space, refine the point to the centroid or any other point (such as, for example, the most anterior or most posterior point).

Skeletonization of the segmented image dataset can help refine the respiratory-gated point cloud. It may be difficult to capture a respiratory-gated point cloud that would match a patient image dataset due to the inability to physically touch the airway wall in many orientations. Therefore the system can use the calculated centerlines between the dataset and the respiratory-gated point cloud to refine accuracy. Various methods of skeletonization are well known in the art and can be applied to the image datasets of certain embodiments of the present invention.

In an alternative embodiment, registering the classified respiratory-gated point cloud to the segmented image dataset comprises registering the classified respiratory-gated point cloud representing at least one branch of the patient's respiratory system to corresponding anatomical points of reference in the registered segmented image data set representing the branch(es) of the patient's respiratory system. In certain embodiments, the classified respiratory-gated point cloud sections corresponding to the trachea, the right main bronchus (RMB), and the left main bronchus (LMB) are registered to a plurality of branches of the patient's respiratory system, wherein the plurality of branches comprise the trachea, the right main bronchus (RMB), and the left main bronchus (LMB). Rotational shifts may be found through lumen data collection. Matching the trachea, RMB, and LMB in patient space and image space will provide rotational registration refinement. While the lung is commonly defined as one organ, in certain embodiments separate registrations between the right and left lung or even different lobes of the lung can provide additional refinement. Carina touch points can be used to perform translational shifts to the registration between patient space and image space.

In one embodiment a lung atlas can be used to develop patient specific airway trees, lung regions, lobes, lymph nodes, vessels, and other structures. These structures can be key to things such as correctly staging lung cancer. Correctly identifying the spread of cancer to lymph nodes can determine the best course of patient treatment. Recording the sampled locations to determine a consistent staging methodology and correctly identifying the region of the lung is key. A lung atlas can also be used to automatically select registration points within a patient such as the Main Carina or other branch points that can be touched by the user to register a dataset to the patient space. Using a lung atlas with an airway tree segmented, a patient specific airway tree can be determined by deforming the lung atlas to the patient's dataset to produce a patient specific airway tree. This can be used for a navigation pathway map, initialization points for other image processing steps, or to produce an error metric for multiple algorithms. Accordingly, in certain embodiments, a lung atlas can be modified or deformed according to the respiratory-gated point cloud.

In another embodiment, 3D image datasets of an organ (e.g., the heart or lung(s)) are segmented to determine a center line of the pathway, such that a string of points, shape or diameter of the pathway can be determined. Patient image information can be matched to the localization information in order to match 3D image space to actual patient space. Thus, an airway shape may be provided along with discrete segments providing shape, orientation, and location information.

In yet another embodiment, 3D image datasets of an organ (e.g., the heart or lung(s)) are segmented to determine a wall, inner surface, or effective inner surface of the pathway, such that a shape or diameter of the pathway can be determined. An effective inner surface may be the representation of an airway that can be tracked based upon the instrumentation used to collect points. An instrument dragged through or passed through and airway may be limited to its ability to track exactly along the surface of the airway and is generally a fixed distance from the wall (i.e., a 5 mm diameter airway may only be tracked in a 3 mm diameter space as there is a 1 mm offset of the sensor from the instrument or device it is inserted to the outer wall). Patient image information may be matched to the localization information in order to match 3D image space to actual patient space. Thus, an airway shape is provided along with discrete segments providing shape, orientation, and location information.

In one embodiment, the tracking of therapy delivery such as energy, material, device, or drug is described. Delivery of a therapy for COPD, asthma, lung cancer and other lung diseases needs tracking of the delivery location and/or pattern. This can be done over treatment sessions (i.e., Bronchial Thermoplasty) or have a dynamically changing dose or energy (RF, cryo, microwave, steam, radiation, or drugs) based on location and trajectory of the delivery device. Using the tracking location and trajectory to modify the dose or energy real-time is described. The power of an ablation device can be changed as the device is directed at the target or can be turned off if outside a defined region. For delivery of therapy that is delivered over multiple sessions, the recorded locations of treated areas can be merged together for each session to give the patient a complete treatment. The treatments can also be modeled before delivery to determine a more effective delivery pattern, dose, or energy.

In another embodiment, a catheter used in the forming of the respiratory-gated point cloud can be integrated with one or more fiber optic localization (FDL) devices and/or techniques. In this way, the localization element (such as an electromagnetic (EM) sensor) provides the 3D spatial orientation of the device, while the FDL provides shape sensing of the airway, vessel, pathway, organ, environment and surroundings. Conventional FDL techniques can be employed. In various embodiments, for example, the FDL device can be used to create localization information for the complete pathway or to refine the localization accuracy in a particular segment of the pathway. By either using 3D localization information, shape, or both detected by the FDL device, the system can use a weighted algorithm between multiple localization devices to determine the location and orientation of the instrument in the patient. The FDL device can also be used as or in conjunction with the PTD to track the patient's motion such as respiration or heartbeat.

In other embodiments, surgical instrument 12 (see FIG. 1) may be a bronchoscope that can capture a video view. This embodiment may comprise, a guidewire or other navigated instrument with one to one rotation to continuously align a virtual display view to be consistent with the actual bronchoscopic video view. A similar technique can be used with OCT, IVUS, or EBUS devices to orient the virtual view to the image captured by the OCT, IVUS, or EBUS devices.

Still other embodiments involve using video input of the bronchoscope to adjust the virtual "fly-through" view to be consistent with the user's normal perspective. For example, conventional video processing and matching techniques can be used to align the real-time video and the virtual image.

Still other embodiments involve using bronchoscopic video to provide angular information at a current location to provide targeting or directional cues to the user. Angular information can be derived from the location of patient anatomy in the image and the relative size of each within the image. Using information extracted from the video captured by the bronchoscope, the system can determine the direction of the display. This can be done using, for example, translation, rotation, or a combination of both. By comparing the real-time image captured to the modified image constructed from the respiratory-gated point cloud, the system can use this information to align the modified image and/or enhance the system accuracy.

In yet another embodiment, a high-speed three-dimensional imaging device, such as an optical coherence tomography (OCT) device, can be tracked. In accordance with conventional methods, such a device can only view 1-2 mm below the surface. With a localization element (e.g., electromagnetic sensor) attached in accordance with the systems and methods described herein, multiple 3D volumes of data can be collected and a larger 3D volume of collected data can be constructed. Knowing the 3D location and orientation of the multiple 3D volumes will allow the user to view a more robust image of, for example, pre-cancerous changes in the esophagus or colon. This data can also be correlated to pre-acquired or intra-procedurally acquired CT, fluoroscopic, ultrasound, or 3D fluoroscopic images to provide additional information.

Among several potential enhancements that could be provided by a surgical instrument navigation system as described herein is that a user could overlay the planned pathway information on to the actual/real-time video image of the scope or imaging device (such as ultrasound based device). Additionally, the system and apparatus could provide a visual cue on the real-time video image showing the correct direction or pathway to take.

According to another particular embodiment, 3D location information may be used to extend the segmented airway model. The 3D airway can be extended as the instrument is passed along the airway by using this location information as an additional parameter to segment the airway from the CT data. Using an iterative segmentation process, for instance, the 3D location information of the instrument can be used to provide seed points, manual extension, or an additional variable of likelihood of a segmented vessel or airway existing in the 3D image volume. These added airways can be displayed in a different format or color (for example) or some other visual indicia to indicate to the user that they are extending the segmented airway using instrument location information.

The multi-dimensional imaging modalities described herein may also be coupled with digitally reconstructed radiography (DRR) techniques. In accordance with a fluoroscopic image acquisition, for example, radiation passes through a physical media to create a projection image on a radiation-sensitive film or an electronic image intensifier. Given a 3D or 4D dataset as described herein, for example, a simulated image can be generated in conjunction with DRR methodologies. DRR is generally known in the art, and is described, for example, by Lemieux et al. (Med. Phys. 21(11), Nov. 1994, pp. 1749-60).

When a DRR image is created, a fluoroscopic image is formed by computationally projecting volume elements, or voxels, of the 3D or 4D dataset onto one or more selected image planes. Using a 3D or 4D dataset of a given patient as described herein, for example, it is possible to generate a DRR image that is similar in appearance to a corresponding patient image. This similarity can be due, at least in part, to similar intrinsic imaging parameters (e.g., projective transformations, distortion corrections, etc.) and extrinsic imaging parameters (e.g., orientation, view direction, etc.). The intrinsic imaging parameters can be derived, for instance, from the calibration of the equipment.

Figure 11A:
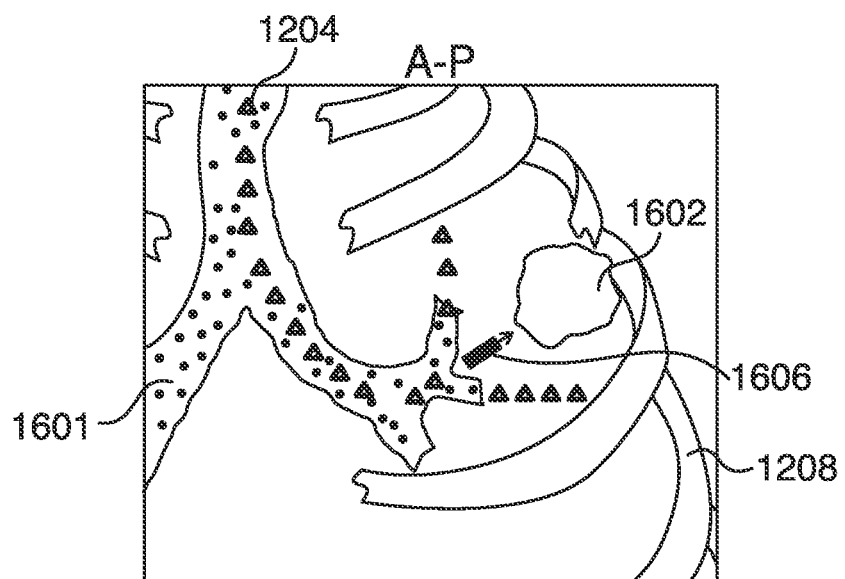
FIG. 11A illustrates a generated image of an anterior to posterior (A-P) view of a region (or tissue) of interest of a patient and FIG. 11B illustrates a generated image of a lateral view of a region (or tissue) of interest of a patient according to an embodiment of the present invention.
Figure 11B:
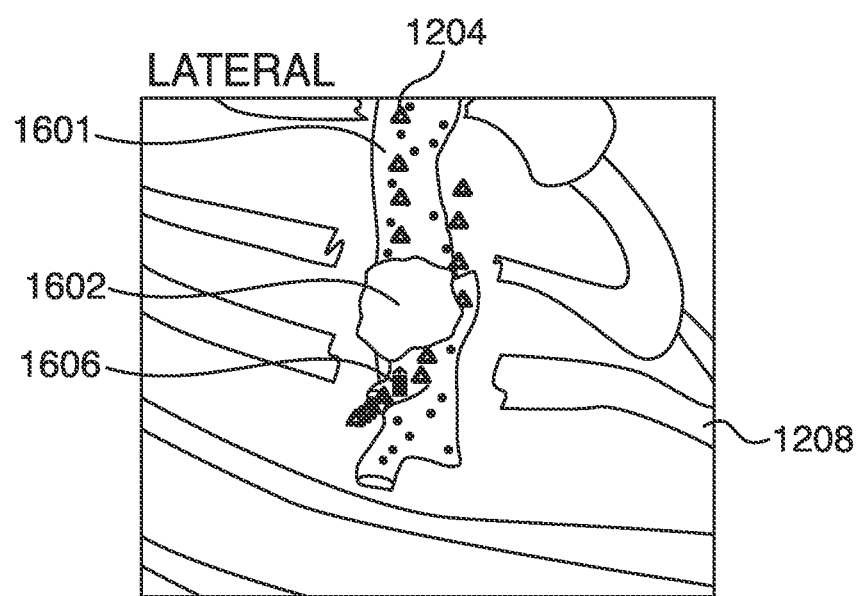

Referring now to FIGS. 11A and 11B, in one embodiment of the present invention, the generated DRR image simulates bi-planar fluoroscopy wherein an image of a region (or tissue) of interest 1602 near the ribs 1208 of a patient 13 can be displayed for two planes of a 3D or 4D image dataset. In certain embodiments, the two image planes of the simulated bi-planar fluoroscopy are oriented 90 degrees apart, however it is understood that other angles are contemplated. One image view that may be displayed is the anterior-to-posterior (A-P) plane (FIG. 11A) and another image view that may be displayed is the lateral plane (FIG. 11B). The display of these two image views provides another method to see the up-and-down (and other directional) movement of the surgical instrument 12 (not shown). This simulated bi-planar fluoroscopy further provides the ability to see how the surgical instrument 12 moves in an image(s), which translates to improved movement of surgical instrument 12 in a patient 13. Additional information can be simultaneously integrated with the simulated bi-planar fluoroscopy (in A-P and lateral views) using minP (minimum intensity projection or maxP (maximum intensity projection) volume, including one or more of: (i) the segmented airway 1601, (ii) the region (or tissue) of interest 1602, (iii) a real-time or simulated real-time rendering of the trajectory and location 1606 of surgical instrument 12, (iv) and the historical pathway 1204 of the surgical instrument 12. Displaying the historical pathway 1204 of surgical instrument 12 can assist the navigation of surgical instrument 12 in areas or situations in which there may be incomplete segmentation of the images of the patient's respiratory system. In another embodiment, a physician or other healthcare professional may be able to zoom in or out or pan through the simulated bi-planar fluoroscopy images.

Figure 12:
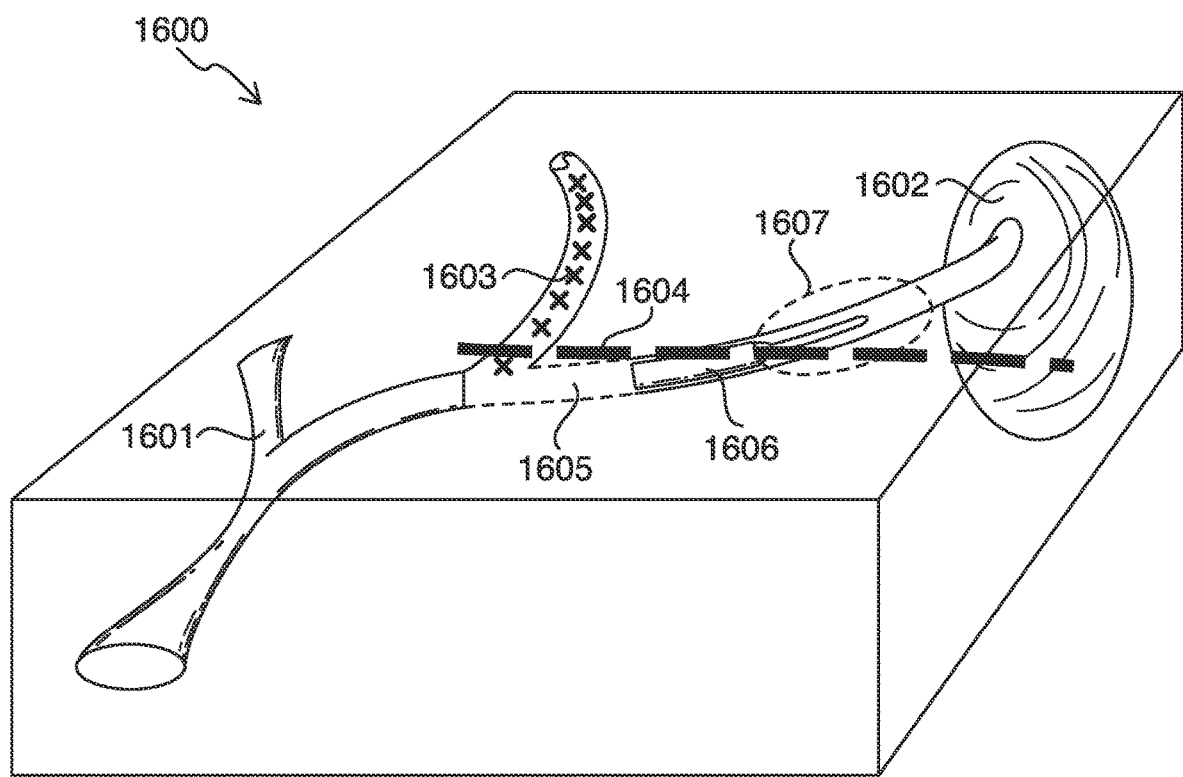
FIG. 12 is a perspective view of a generated image of a region (or tissue) of interest of a patient according to an embodiment of the present invention.

According to another embodiment of the present invention, FIG. 12 depicts a CT minP/maxP volume reading where precise navigation of a surgical instrument 12 (not shown) having a localization element 24 (e.g., using an electromagnetic sensor) (not shown) near a region(s) (or tissue) of interest is carried out with incomplete segmentation results. This embodiment may provide the physician or other healthcare professional with a view or image 1600 using minP (minimum intensity projection) or maxP (maximum intensity projection) volume renderings to simultaneously integrate one or more of the segmented airway 1601, the region(s) (or tissue) of interest 1602, and a visually distinct representation of previously traversed paths that are "bad" (i.e., incorrect) 1603. Additionally, this embodiment may also simultaneously integrate the distance and angle 1604 to the region(s) (or tissue) of interest 1602 (e.g., a target lesion or tumor) using a vector fit to the last 1 cm (or so) of travel (in addition to, or in place of, instantaneous orientation provided by a 5DOF localization element as described herein) and may incorporate user provided "way points" to create a final-approach tube 1605 to the region(s) (or tissue) of interest 1602. As described herein, the image 1600 may also provide a real-time or simulated real-time rendering the trajectory and location 1606 of surgical instrument 12 (e.g., the tip component as shown with a virtual extension 1607 to the region(s) (or tissue) of interest).

Figure 13A:
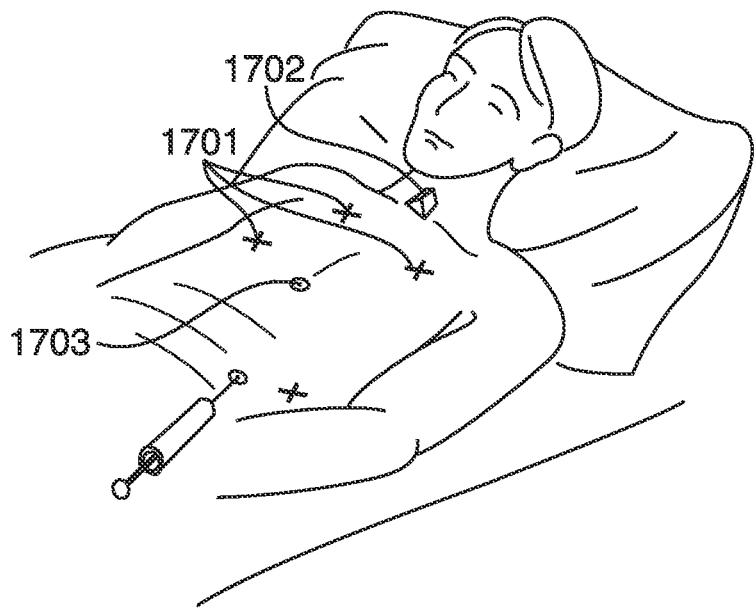
FIGS. 13A and 13B show an alternative method of generating a 4D dataset for 4D thoracic registration using surgical instrument navigation system according to an embodiment of the present invention.
Figure 13B:
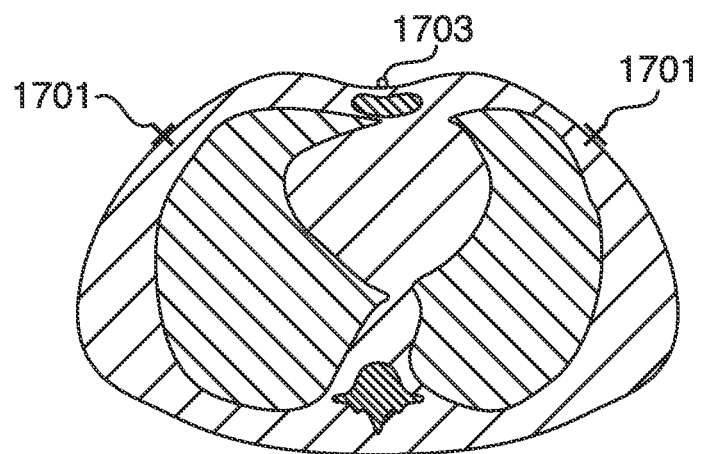

In another embodiment, an alternative method of generating a 4D dataset for 4D thoracic registration using surgical instrument navigation system 10 is illustrated by FIGS. 13A and 13B. In general, the 4D dataset may be acquired through respiratory gating or tracheal temporal registration. In accordance with the methods described herein, for example, acceleration of N data collectors (e.g., magnetic or MEMS accelerometers, for instance) are measured to register the thorax in time and space, using the general formula: $dataT_{thorax}=F(t)$. As shown in FIGS. 13A and 13B, the various sensors 1701 and tracheal sensor 1702 provide data as described herein, as does sternum sensor 1703 (e.g., x, y, and z dynamic tracking). The position and trajectory of a device (e.g., biopsy device or other device or medical instrument described herein) is further capable of being tracked as described herein.

Figure 14:
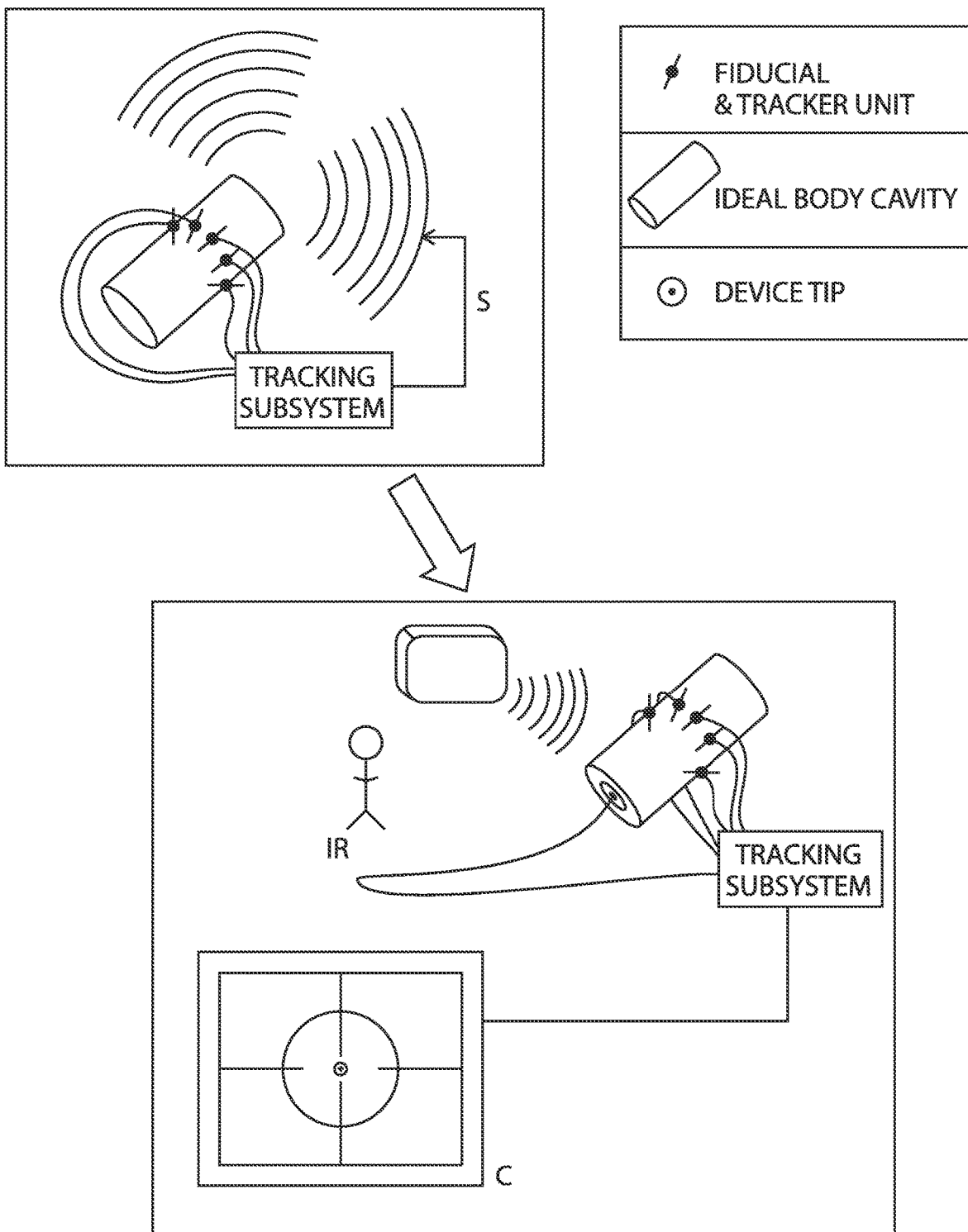
FIG. 14 shows an apparatus and method for respiratory 4D data acquisition and navigation according to an embodiment of the present invention.

FIG. 14 shows another embodiment of an apparatus and method for respiratory 4D data acquisition and navigation. As shown in the upper box, a respiratory problem or issue is scanned (e.g., by a CT and/or MR scanner) and signal S from the tracking subsystem is provide to the CT/IR unit (lower box). The 4D registration based on the motion of the fiducial and tracker units (which could be, e.g., electromagnetic sensors, MEMS devices, combinations thereof, and the like) is provided to the user (shown as an interventional radiologist (IR)) on computer C. The system is capable of displaying the current position of the device tip in the image data shown to the IR, using the fiducial or tracker locations in the scan coupled with the real-time motion information provided by the device tip (e.g., which can include a sensor as described herein), thus providing registration.

Other embodiments include, for example, using an electromagnetic sensor as an LC or energy transmission device. This stored energy could be used to actuate a sampling device such as forceps or power a diagnostic sensor.

In various aspects and embodiments described herein, one can use the knowledge of the path traveled by the surgical instrument and segmented airway or vessel from the acquired image (e.g., CT) to limit the possibilities of where the surgical instrument is located in the patient. The techniques described herein, therefore, can be valuable to improve virtual displays for users. Fly through, fly-above, or image displays related to segmented paths are commonly dependent upon relative closeness to the segmented path. For a breathing patient, for example, or a patient with a moving vessel related to heartbeat, the path traveled information can be used to determine where in the 4D patient motion cycle the system is located within the patient. By comparing the 3D location, the patient's tracked or physiological signal is used to determine 4D patient motion cycle, and with the instrument's traveled path, one can determine the optical location relative to a segmented airway or vessel and use this information to provide the virtual display.

The surgical instrument navigation system of certain embodiments of the present invention may also incorporate atlas maps. It is envisioned that three-dimensional or four-dimensional atlas maps may be registered with patient specific scan data, respiratory-gated point clouds, or generic anatomical models. Atlas maps may contain kinematic information (e.g., heart and lung models) that can be synchronized with four-dimensional image data, thereby supplementing the real-time information. In addition, the kinematic information may be combined with localization information from several instruments to provide a complete four-dimensional model of organ motion. The atlas maps may also be used to localize bones or soft tissue which can assist in determining placement and location of implants.

As noted herein, a variety of instruments and devices can be used in conjunction with the systems and methods described herein.

As a result of or in the course of certain surgical procedures, a patient's physical state may be changed relative to an acquired image dataset. Incisions, insufflations, and deflation of the lung and re-positioning of the patient are just some of the procedures that may cause a change in the patient's physical state. Such changes in physical state may make it more difficult to find a lesion or point in an organ of the patient. For example, in a lung wedge resection the thoracic surgeon is palpating the lung to find the lesion to resect; if this lesion is 1-2 cm under the surface it can be very difficult to find.

In one embodiment, a first localization element is placed at a location or region of interest (e.g., a tumor) within an organ of a patient and a second localization element is used to identify the location of the first localization element from outside the organ in which the first localization element has been positioned. Preferably, the first localization element is attached or otherwise connected to tissue or situated such that its position relative to the location or region of interest remains fixed. In some embodiments, for example, the first localization element can be sutured in place, and/or or may have barbs, hooks, flexed spring shape (bowed) and/or wires, or other suitable connection techniques, to hold it substantially in place.

Figure 15B:
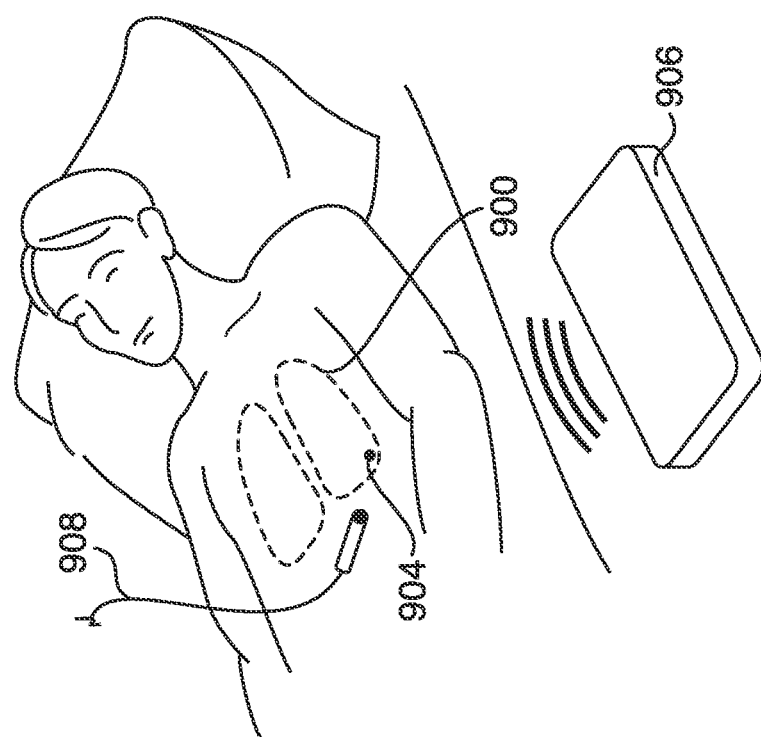
FIG. 15A is a side perspective view of the implanting of a first localization element and FIG. 15B is a side perspective view of locating the first localization element with a second localization element according to an embodiment of the present invention.
Figure 15A:
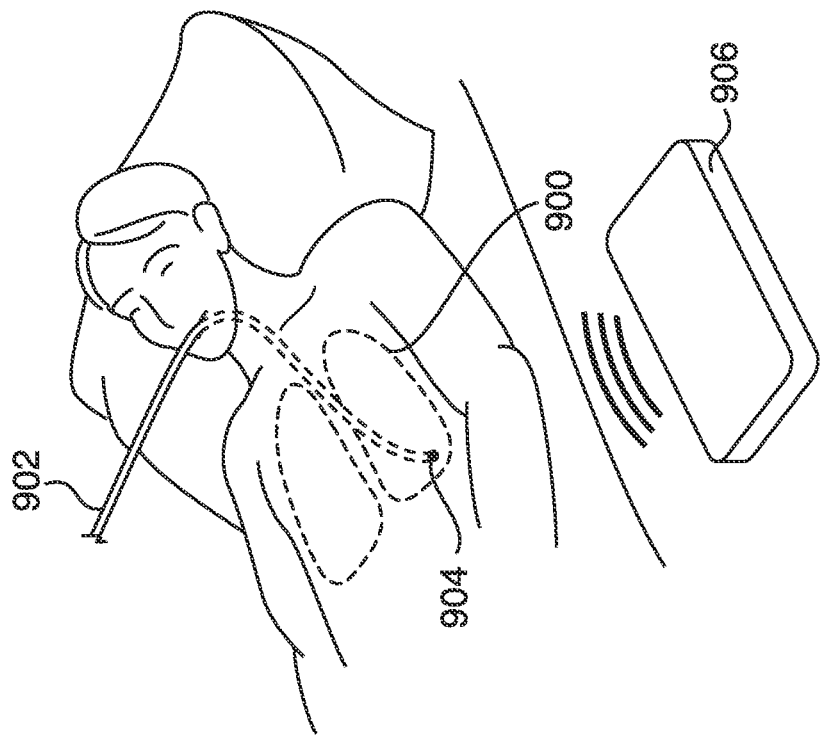

Referring now to FIG. 15A, in one embodiment first localization element 904 is attached to tissue in a region of the organ 900 of the patient. First localization element 904 may be placed, for example, percutaneously, endobronchially, or via the vasculature. As illustrated, first localization element may be wireless, however in other embodiments first localization element may be wired. In one embodiment, first localization element 904 is placed using an endolumenal device 902. In percutaneous (or other) methods, the leads of the first localization element may exit the patient and the device removed during or after a procedure (e.g., during resection of a tumor).

In one embodiment, first localization element 904 is positioned in the organ and may be registered to a segmented image dataset prior to any procedural resection or incision has occurred. Otherwise, pre-procedural images may not match the patient's anatomy (e.g., once an incision is made, the patient is insufflated for a VATS procedure, or the patient is otherwise re-positioned).

After the first localization element 904 is positioned in an organ and registered, as shown in FIG. 15B, the patient may then be manipulated in a manner that would potentially induce a physical change that would cause the patient's anatomy to not match a pre-procedure acquired segmented image dataset. A second localization element 908 (e.g., a pointer probe) may then be used to identify the location of the first localization element 904 from outside the patient's organ 900. Typically, second localization element 908 is placed near patient's organ 900 or other area of interest, e.g., via an incision or through a working port of a VATS procedure or otherwise in a position to locate first localization element 904.

Although the second localization element 908 will be outside the organ into which first localization element 904 is placed, it need not be outside the body of the patient. In certain embodiments of the present invention, second localization element 908 can be inserted into the patient through a surgical portal. In other embodiments, second localization element 908 will be outside the body of the patient. Optionally, and as illustrated in FIG. 15, in one embodiment a third localization element 906 may be used to locate first localization element 904 and second localization element 908 relative to third localization element 906, wherein the third localization element 906 may comprise a 3D localizing device (e.g., an electromagnetic field generator) with a 3D coordinate system. In another embodiment, third localization element 906 may be used to locate second localization element 908 relative to third localization element 906.

As illustrated in FIG. 15, in one embodiment, the organ to which first localization element 904 is attached is a lung. In other embodiments, however, first localization element 904 may be attached in another organ such as a kidney or the liver.

In certain embodiments, the first, second and (optional) third localization elements may all be elements of a tracking subsystem 20 (see FIG. 1). If tracking subsystem 20 is an electromagnetic tracking system, the third localization element would typically comprise an electromagnetic field generator (transmitter) that emits a series of electromagnetic fields designed to engulf the patient, and the first and second localization elements could be coils that would receive (receivers) an induced voltage that could be monitored and translated into a coordinate position. However, the positioning of the electromagnetic field generator (transmitter), and the first and second localization elements (receivers) may also be reversed, such that the first localization element is a generator and the second and third localization elements are receivers or the second localization element is a generator and the first and third localization elements are receivers. Thus in certain embodiments, first localization element 904 may be a receiver, while in other embodiments, first localization element 904 may be a receiver. In certain embodiments, second localization element 908 may be a receiver, while in other embodiments, second localization element 908 may be a receiver. In certain embodiments, third localization element 906 may be a receiver, while in other embodiments, third localization element 906 may be a receiver.

In one embodiment of the present invention, surgical instrument 12 (see FIG. 1) comprises a surgical catheter that is steerable (referred herein to as "steerable catheter") to gain access to, manipulate, remove or otherwise treat tissue within the body including, for example, heart or lung tissue. Generally, steerable catheters can be remotely manipulated via a steering actuator. In a typical medical procedure, the steering actuator is located outside of the patient's body and is manipulated in order to steer the steerable catheter to a desired location within the body.

In accordance with one embodiment of the present invention and referring now to FIG. 16, steerable catheter 200 comprises actuating handle 216 and elongate flexible shaft 230. Elongate flexible shaft 230 has proximal end portion 232, distal end portion 234, central longitudinal axis 207 extending from proximal end portion 232 to distal end portion 234, and outer wall 236 comprising a biocompatible material extending from proximal end portion 232 to distal end portion 234. In certain embodiments, the biocompatible material is a biocompatible polymer.

In certain embodiments, elongate flexible shaft comprises a flexible shaft portion 202 at its proximal end portion 232 and a steerable shaft portion 203 at its distal end portion 234. In other embodiments, elongate flexible shaft 230 comprises flexible shaft portion 202 at its distal end portion 234 and a steerable shaft portion at its proximal end portion 232. Flexible shaft portion 202 has a first stiffness and steerable shaft portion 203 has a second stiffness that is less than the first stiffness. Stated differently, flexible shaft portion 202 may be comprised of a more rigid material which has a first stiffness, while steerable shaft portion 203 may be comprised of a softer material having a second stiffness. In certain embodiments, flexible shaft portion 202 is formed from a relatively high-durometer material and steerable shaft portion 203 is formed from a less stiff, lower-durometer material than the flexible shaft portion. Additionally, flexible shaft portion 202 may be reinforced with a molded-in braided reinforcement material. In one alternative embodiment, flexible shaft portion 202 comprises a spring having a first coil diameter and steerable shaft portion 203 comprises a spring having a second coil diameter. The first coil diameter may be greater than the second coil diameter and, accordingly, the first coil diameter of the flexible shaft portion has a greater stiffness than the second coil diameter of the steerable shaft portion. In one embodiment, elongate flexible shaft 230, including flexible shaft portion 202 and steerable shaft portion 203, are preferably formed from a biocompatible material such as Pebax™, manufactured by Arkema.

Figure 17A:
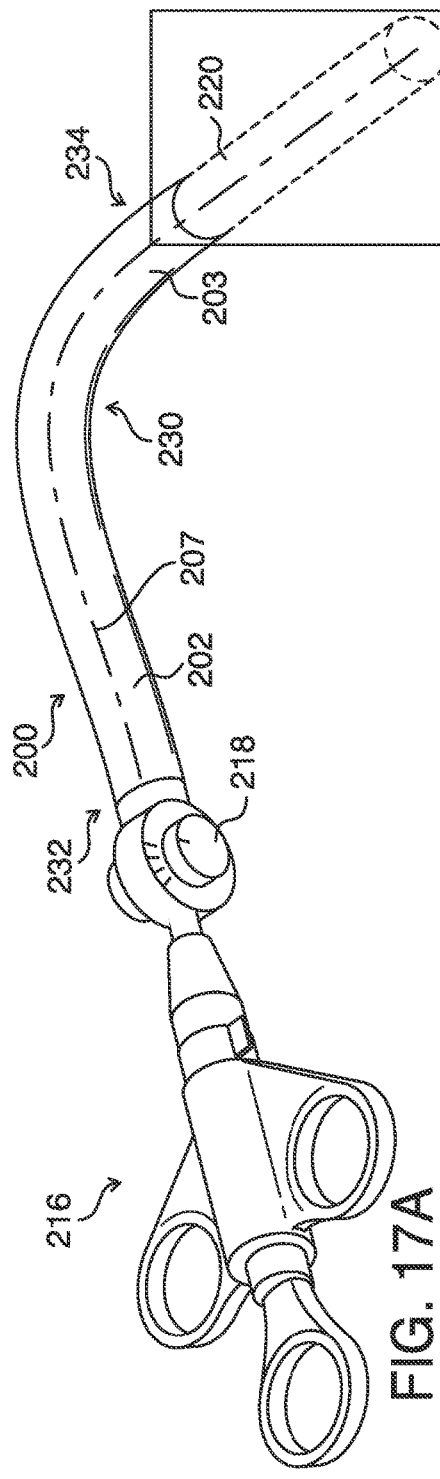
FIG. 17A shows a side perspective view of a steerable catheter and associated possible biopsy devices including a forceps device (FIG. 17B), an auger device (FIG. 17E), a boring bit device (FIG. 17C), a brush device (FIG. 17D), an aspiration needle device (FIG. 17F), and a side exiting tip component (FIG. 17G) according to various embodiment of the present invention.
Figure 17B:
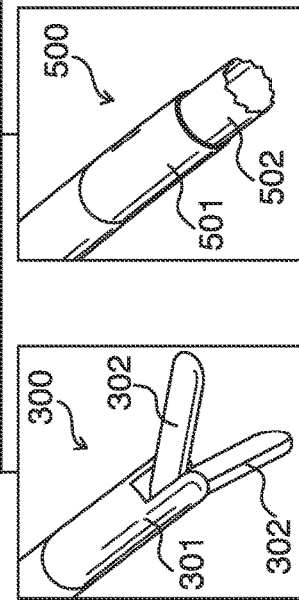
Figure 17C:
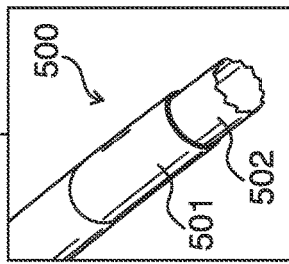
Figure 17D:
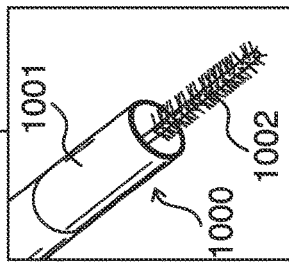

Biopsy device 220 is at distal end portion 234 of elongate flexible shaft 230 and, in certain embodiments, may be used to access or manipulate tissue. In one embodiment, biopsy device 220 is operated by actuation wire 212 (see FIG. 16A) which is housed within actuation channel 209 extending through elongate flexible shaft 230. Actuation wire 212 has a proximal end (not shown) attached to handle 216 and a distal end (not shown) attached to biopsy device 220. As illustrated in FIG. 17A and as described in greater detail elsewhere herein, a variety of biopsy devices 220 can be used with the steerable catheter, including, but not limited to, for example, a forceps device 17B, an auger device 17E, a boring bit device 17C, an aspiration needle device 17F, or a brush device 17D. In one embodiment, biopsy device 220 is comprised by a side exiting tip component 17G comprising a forceps device, and auger device, a boring bit device, a brush device, or an aspiration needle device as described in greater detail elsewhere herein.

Referring again to FIG. 16, steerable catheter 200 further includes a steering mechanism comprising steering actuator 218 (proximate actuating handle 216) and at least one pull wire 210 (see FIG. 16A) housed in elongate flexible shaft 230 and attached to steering actuator 218. In certain embodiments, manipulation of steering actuator 218 applies a tension to pull wire(s) 210 and effects a deflection of steerable shaft portion 203 (located at or near the distal end portion of elongate flexible shaft 230) relative to flexible shaft portion 202. In certain embodiments, pull wire 210 extends the entire length of elongate flexible shaft 230. In other embodiments, pull wire 210 may extend only into proximal end portion 232 of elongate flexible shaft 230. In yet other embodiments, pull wire 210 may extend only into distal end portion 234 of elongate flexible shaft 230. In certain embodiments, pull wire 210 is operably connected at its proximal end to steering actuator 218 and anchored at its distal end to biopsy device 220 mounted on distal end portion 234 of elongate flexible shaft 230. Thus, pull wire 210 passes through the flexible shaft portion and the steerable shaft portion of the elongate flexible shaft. The material for pull wire 210 may be any suitable material usable with a catheter, such as stainless steel wire.

Figure 18A:
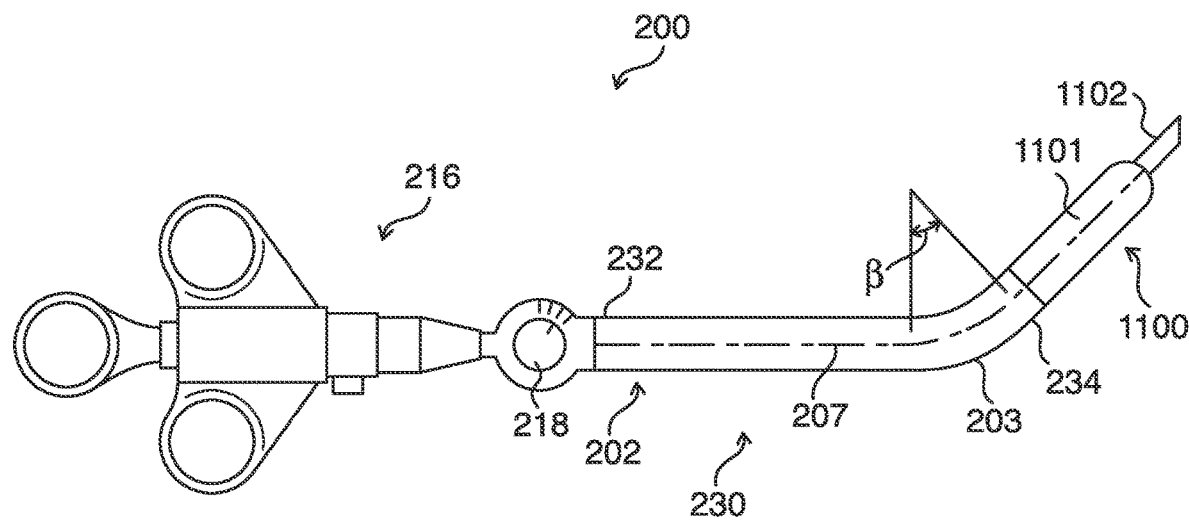
FIGS. 18A and 18B are a side views of a steerable catheter deflected by actuating the steering actuator according to an embodiment of the present invention.
Figure 18B:
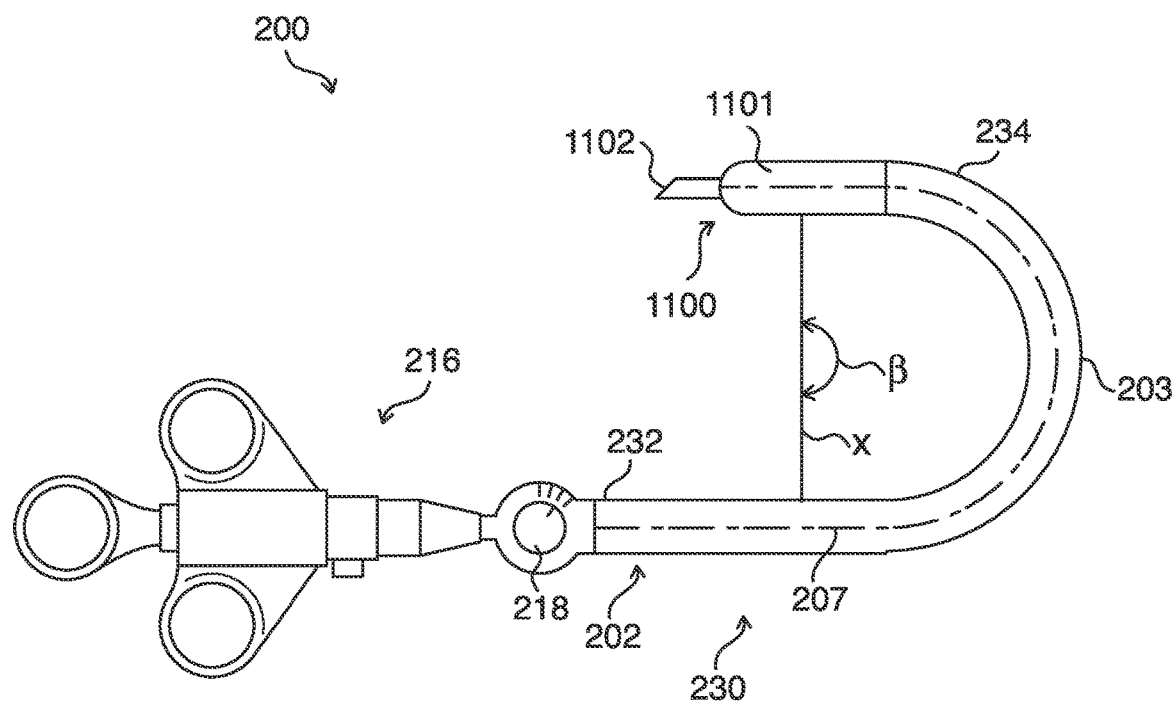

Referring now to FIG. 18A, distal end portion 234 may be deflected relative to proximal end portion 232 such that an arc β of at least 20 degrees may be introduced into elongate flexible shaft 230 by manipulation of steering actuator 218. As shown in FIGS. 18A and 18B, biopsy device is shown as an aspiration needle device 1100 (described in greater detail elsewhere herein). In other embodiments, as described in greater detail elsewhere herein, biopsy device 220 may comprise any of a range of other biopsy devices such as an auger device, a boring bit device, a brush device, a side exiting tip component, etc. In one embodiment, an arc of at least about 30 degrees (i.e., β is at least 30 degrees) may be introduced into elongate flexible shaft 230. By way of further example, an arc of at least about 40 degrees may be introduced into elongate flexible shaft 230. By way of further example, an arc of at least about 45 degrees may be introduced into elongate flexible shaft 230. By way of further example, an arc of at least about 60 degrees may be introduced into elongate flexible shaft 230. By way of further example, an arc of at least about 70 degrees may be introduced into elongate flexible shaft 230. By way of further example, an arc of at least about 80 degrees may be introduced into elongate flexible shaft 230. By way of further example, an arc of at least about 90 degrees may be introduced into elongate flexible shaft 230. By way of further example, an arc of at least about 100 degrees may be introduced into elongate flexible shaft 230. By way of further example, an arc of at least about 110 degrees may be introduced into elongate flexible shaft 230. By way of further example, an arc of at least about 120 degrees may be introduced into elongate flexible shaft 230. By way of further example, an arc of at least about 130 degrees may be introduced into elongate flexible shaft 230. By way of further example, an arc of at least about 140 degrees may be introduced into elongate flexible shaft 230. By way of further example, an arc of at least about 150 degrees may be introduced into elongate flexible shaft 230. By way of further example, an arc of at least about 160 degrees may be introduced into elongate flexible shaft 230. By way of further example, an arc of at least about 170 degrees may be introduced into elongate flexible shaft 230. By way of further example, an arc of about 180 degrees may be introduced into elongate flexible shaft 230.

As illustrated in FIG. 18B, in one embodiment, manipulation of steering actuator 218 introduces an arc β of at least 180 degrees into elongate flexible shaft 230. Distal end portion 234 may be moved such that a distance of no more than 1.5 inch separates two regions of elongate flexible shaft 230 located at opposing ends of a chord X connecting to two points separated by at least 180 degrees on the arc. In certain embodiments, a distance of no more than 1 inch separates two regions of elongate flexible shaft 230 located at opposing ends of chord X. In certain embodiments, a distance of no more than 0.75 inches separates two regions of elongate flexible shaft 230 located at opposing ends of chord X. In certain embodiments, a distance of no more than 0.5 inches separates two regions of elongate flexible shaft 230 located at opposing ends of chord X. In certain embodiments, a distance of no more than 0.25 inches separates two regions of elongate flexible shaft 230 located at opposing ends of chord X. In other embodiments, manipulation of steering actuator 218 introduces an arc β of at least 120 degrees into elongate flexible shaft 230. Distal end portion 234 may be moved such that a distance of no more than 1.5 inch separates two regions of elongate flexible shaft 230 located at opposing ends of a chord X connecting to two points separated by at least 120 degrees on the arc. In certain embodiments, a distance of no more than 1 inch separates two regions of elongate flexible shaft 230 located at opposing ends of chord X. In certain embodiments, a distance of no more than 0.75 inches separates two regions of elongate flexible shaft 230 located at opposing ends of chord X. In certain embodiments, a distance of no more than 0.5 inches separates two regions of elongate flexible shaft 230 located at opposing ends of chord X. In certain embodiments, a distance of no more than 0.25 inches separates two regions of elongate flexible shaft 230 located at opposing ends of chord X.

In another embodiment, elongate flexible shaft 230 of steerable catheter 200 houses more than one pull wire 210 attached to steering actuator 218. The use of multiple pull wires may be preferred in some embodiments over steerable catheters having a single pull wire. A steerable catheter having only one pull wire 210 attached to steering actuator 218 will typically bend in only one direction, commonly referred to as uni-directional steering. A steerable catheter capable of only uni-directional steering could be rotated, such that any point surrounding the distal end of the elongate flexible shaft may be reached by bending the catheter tip and rotating the catheter. Two or more pull wires (e.g., two, three, four, or even more) attached to steering actuator 218, however, could provide multi-directional steering thereby permitting the elongate flexible shaft to be deflected in two or more directions.

In one embodiment, elongate flexible shaft 230 comprises one or more lumens extending from proximal end portion 232 to distal end portion 234 of elongate flexible shaft 234 that may be used to deliver a medical device or therapy to a surgical site (e.g., fluids, biopsy devices, drugs, radioactive seeds, combinations thereof, or the like). In other embodiments, the lumen(s) may house additional structures such as electrical wires or optical fibers connected to biopsy device 220 on distal end portion 234 of elongate flexible shaft 230. In other embodiments, a vacuum pressure may be applied to the lumen(s) to assist removal of tissue or fluid. In certain embodiments, the lumen may be a working channel in which a biopsy device such as an aspiration needle is housed and operated, wherein the aspiration needle is described in greater detail elsewhere herein (see FIG. 33).

Referring now to FIG. 19, in another embodiment elongate flexible shaft 230 of steerable catheter 200 comprises articulated spline 204 containing a plurality of spline rings 206. Spline rings 206 are affixed in series to at least one hollow spline guide 208 and extend in the direction of longitudinal central axis 207. Articulated spline 204 may be covered in a casing 214 comprising a biocompatible material. In other embodiments, articulated spline 204 is at distal end portion 234 of elongate flexible shaft 230. In yet other embodiments, articulated spline 204 is at proximal end portion 232 of elongate flexible shaft 230. In yet other embodiments, steerable shaft portion 203 comprises articulated spline 204.

In one embodiment, as illustrated in FIG. 19, steerable catheter 200 further comprises forceps device 300 as the biopsy device 220. In other embodiments, as described in greater detail elsewhere herein, biopsy device 220 may comprise any of a range of other biopsy devices such as an auger device, a boring bit device, a brush device, a side exiting tip component, etc. Forceps device 300 comprises forceps housing 301, first and second forceps jaws 302, localization element 24 and localization element lead wire 103, wherein the first and second forceps jaws 302 are operably connected to actuation wire 212. The physician or other healthcare professional actuates forceps device 300 by manipulating handle 216 causing first and second forceps jaws 302 to pivot relative to one another, thereby closing first and second forceps jaws 302 thereby removing tissue. In certain embodiments, forceps device 300 may also comprise a tissue collection region where the removed tissue can be collected. In other embodiments, forceps device 300 can be equipped with, or used in conjunction with, a vacuum pressure (suction) may be used to pull the removed tissue into tissue collection region. In yet other embodiments, tissue collection region of forceps device 300 may have a viewing window through which the removed tissue can be inspected from outside forceps device 300 (see FIG. 27). In other embodiments, localization element 24 may be attached to actuation wire 212 such that movement of actuation wire 212 as handle 215 is manipulated causes coordinated movement of localization element 24 thereby providing an indication that forceps device 300 is being operated. A number of mechanically operated forceps devices are known in the prior art and can be adapted to operably connect to the actuation wire 212 of the steerable catheter 200. As described in greater detail elsewhere herein, biopsy device 220 may comprise any of a range of other biopsy devices such as an auger device, a boring bit device, an aspiration needle device, a brush device, a side exiting tip component, etc.

Referring now to FIG. 19A, hollow spline guides 208 are affixed to opposing inner surfaces of spline rings 206. Pull wires 210 are housed in hollow spline guides 208 with one pull wire housed within each hollow spline guide 208. The hollow spline guides 208 can be made of, for example, stainless steel or other metal, or from a hard polymeric material, such as polyimide or PTFE, or from a polymer lined metal tube, such as a Teflon lined stainless steel tube. Each hollow spline guide 208 may be made of a type of tube commonly used to fabricate hypodermic needles, e.g., a stainless steel tube having an outside diameter of about 0.050 inches or less, and more preferably about 0.018 inches or less. This tubing is sometimes referred to as "hypotube." By way of example, the guide tube may be a 26 gauge stainless steel hypodermic tube, with a nominal outside diameter of 0.0183 inches and a nominal wall thickness of 0.004 inches. The hollow spline guides 208 provide and exhibit high strength and resiliency that resists compression. In one embodiment, by way of example, hollow spline guides 208 are affixed to spline rings 206 by a laser weld. In another embodiment, by way of further example, hollow spline guides 208 are affixed to spline rings 206 by an epoxy. In another embodiment, by way of further example, hollow spline guides 208 are affixed to the spline rings 206 by solder. In another embodiment, by way of further example, hollow spline guides 208 are affixed to spline rings 206 by a brazed joint.

Typically, the outer diameter of elongate flexible shaft 230 of steerable catheter 200 is less than 5 mm. By way of example, in certain embodiments, the outer diameter of elongate flexible shaft 230 of steerable catheter 200 is less than 1 mm. By way of further example, in certain embodiments, the outer diameter of elongate flexible shaft 230 of steerable catheter 200 is less than 2 mm. By way of further example, in certain embodiments, the outer diameter of elongate flexible shaft 230 of steerable catheter 200 is less than 3 mm. By way of further example, in certain embodiments, the outer diameter of elongate flexible shaft 230 of steerable catheter 200 is less than 4 mm. By way of further example, in certain embodiments, the outer diameter of elongate flexible shaft 230 of steerable catheter 200 is less than 5 mm.

While in certain embodiments the steerable catheter 200 is non-navigated, other embodiments of the steerable catheter 200 are navigated. In certain embodiments in which steerable catheter 200 is navigated, a localization element 24 is positioned in elongate flexible shaft 230 or biopsy device 220, preferably at or near the distal end thereof. In certain embodiments, localization element 24 may comprise electromagnetic sensors. However, in other embodiments the steerable catheter 200 may be navigated wherein elongate flexible shaft 230 or biopsy device 220 may further comprise radiopaque markers visible via fluoroscopic imaging, or echogenic materials or patterns that increase visibility of the tip component under an ultrasonic beam. In yet other embodiments the steerable catheter 200 may be navigated wherein distal end portion 234 of elongate flexible shaft 230 or distal end of biopsy device 220 may further comprise radiopaque markers visible via fluoroscopic imaging, or echogenic materials or patterns that increase visibility of the tip component under an ultrasonic beam. In one embodiment, localization element 24 comprises a six (6) degree of freedom (6DOF) electromagnetic sensor. In another embodiment the localization element comprises a five (5) degree of freedom (5DOF) electromagnetic sensor. Using the localization element, the user can have the location of the biopsy device 220 is defined on the navigation screen.

In one embodiment, localization element 24 may be attached to actuation wire 212. Movement of actuation wire 212 as handle 216 is manipulated causes coordinated movement of localization element 24 thereby providing an indication that biopsy device 220 is being operated. In accordance with other embodiments, for example, a localization element as described herein (e.g., an electromagnetic (EM) sensor) is affixed (preferably permanently affixed, but may also be removable) to a biopsy device or medical instrument so that both the biopsy device or medical instrument (or component thereof) and the localization element move together, such that they can be imaged and viewed. In one embodiment, for example, biopsy device 220 is an aspiration needle and the needle tip and the sensor move together. In another embodiment, for example, biopsy device 220 is a brush, forceps, or forceps tissue capture mechanism and these components and the localization element move together. In these and other embodiments, handle 216 may be coupled with localization element 24, thus allowing movement tracking. These various embodiments allow the biopsy device or medical instrument (and components thereof) to be tracked using the localization element, improving overall accuracy and reliability.

Figure 20A:
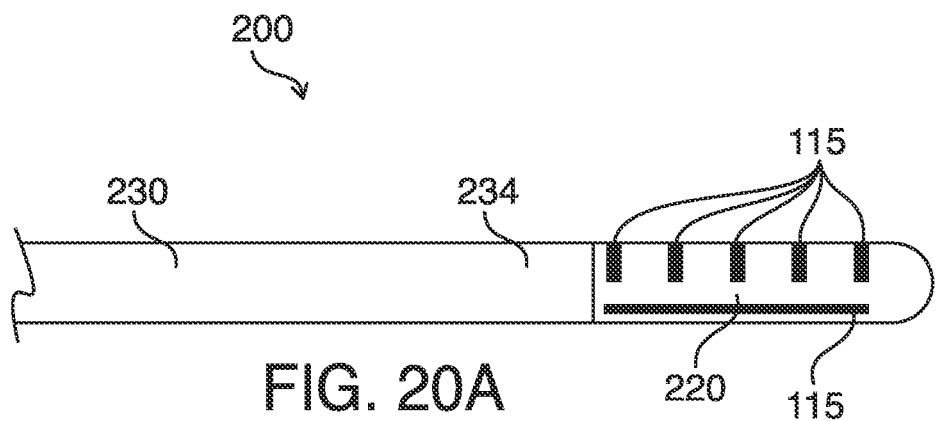
FIGS. 20A, 20B, and 20C show a side, top, and bottom view of the distal end portion of a steerable catheter wherein the biopsy device comprises an angled or directional pattern visible via fluoroscopic imaging according to an embodiment of the present invention.
Figure 20B:
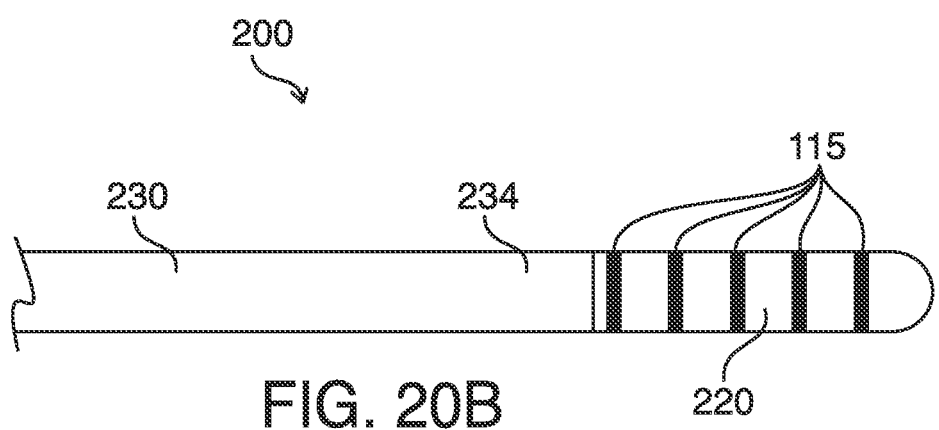
Figure 20C:
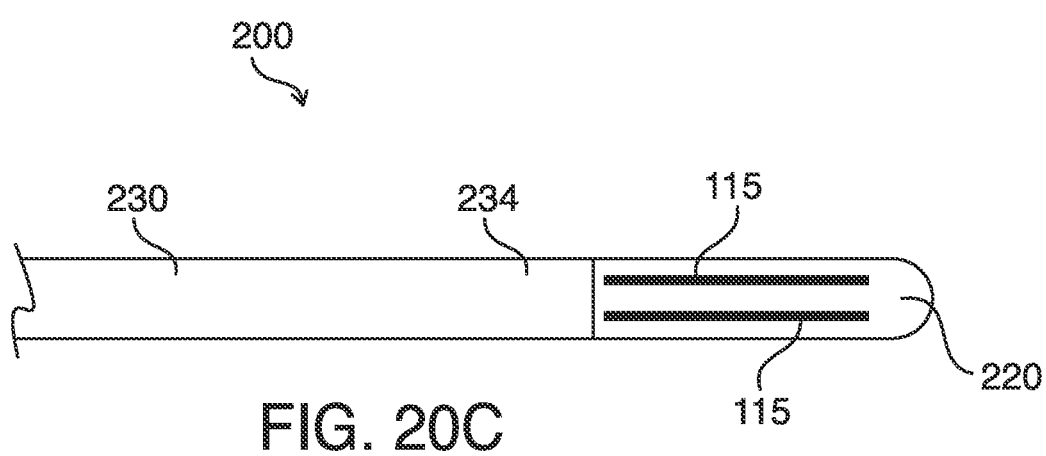

Referring now to FIGS. 20A, 20B and 20C, in one embodiment biopsy device 220 further comprises an angled or directionally arranged radiopaque marker pattern 115 that is visible via fluoroscopic imaging. The radiopaque marker pattern 115 may be made of stainless steel, tantalum, platinum, gold, barium, bismuth, tungsten, iridium, or rhenium, alloys thereof, or of other radiopaque materials known in the art. The radiopaque marker pattern 115 allows for tracking of the location and orientation of the biopsy device 220. Based upon the orientation of the radiopaque marker pattern 115 on the biopsy device 220 with respect to the incident fluoroscopic beam, a distinct image is visible on a fluoroscope. As the biopsy device 220 is navigated and rotated into position at the patient target, the orientation of the radiopaque marker pattern 115 with respect to the incident fluoroscopic beam will be altered resulting in a corresponding change to the fluoroscopic image, thereby allowing the user to know the location and orientation of the biopsy device 220. Accordingly, the user can then operate the biopsy device 220 at the desired patient target. In other embodiments, radiopaque marker pattern 115 may be at distal end portion 234 of elongate flexible shaft 230. In this embodiment, biopsy device 220 may comprise any of the biopsy devices described elsewhere herein (see, e.g., FIGS. 17A-17G).

Figure 21A:
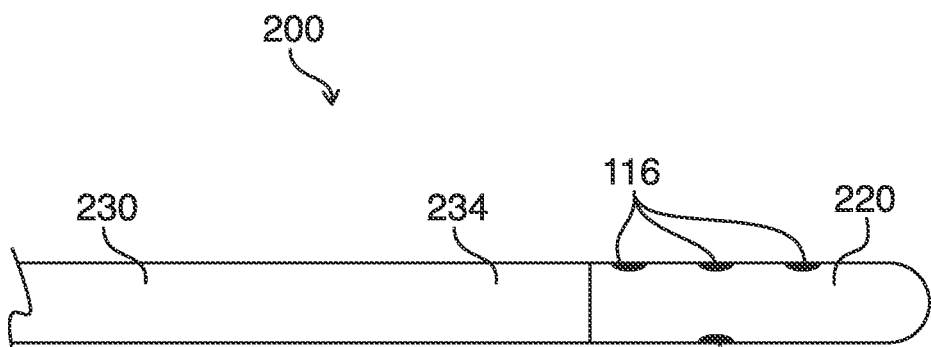
FIGS. 21A, 21B, and 21C show a side, top, and bottom view of the distal end portion of a steerable catheter wherein the biopsy device comprises markers visible via fluoroscopic imaging according to an embodiment of the present invention.
Figure 21B:
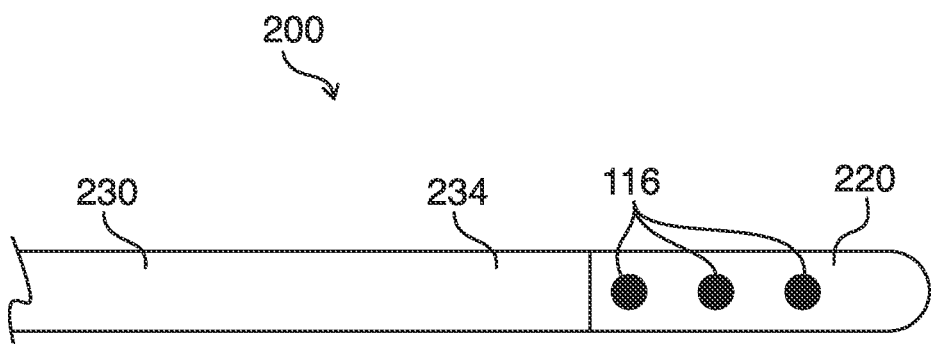
Figure 21C:
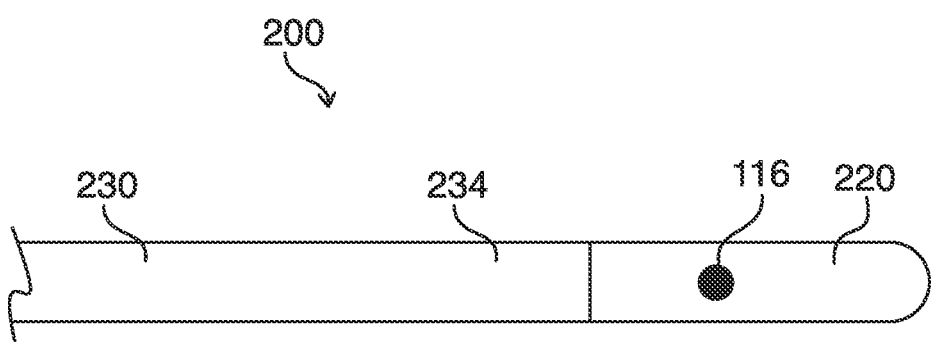

Referring now to FIGS. 21A, 21B, and 21C, in one embodiment biopsy device 220 further comprises generally circular radiopaque markers 116 placed around biopsy device 220, with 3 radiopaque markers on one side of biopsy device 220 and 1 radiopaque marker on the opposite side of biopsy device 220. By way of example, in certain embodiments, 4 radiopaque markers are placed on one side of biopsy device 220 and 2 radiopaque markers are placed on the opposite side of biopsy device 220. By way of further example, in certain embodiments, 5 radiopaque markers are placed on one side of biopsy device 220 and 3 radiopaque markers are placed on the opposite side of biopsy device 220. In other embodiments, circular radiopaque markers 116 may be at distal end portion 234 of elongate flexible shaft 230. In this embodiment, biopsy device 220 may comprise any of the biopsy devices described elsewhere herein (see, e.g., FIGS. 17A-17G).

Figure 22A:
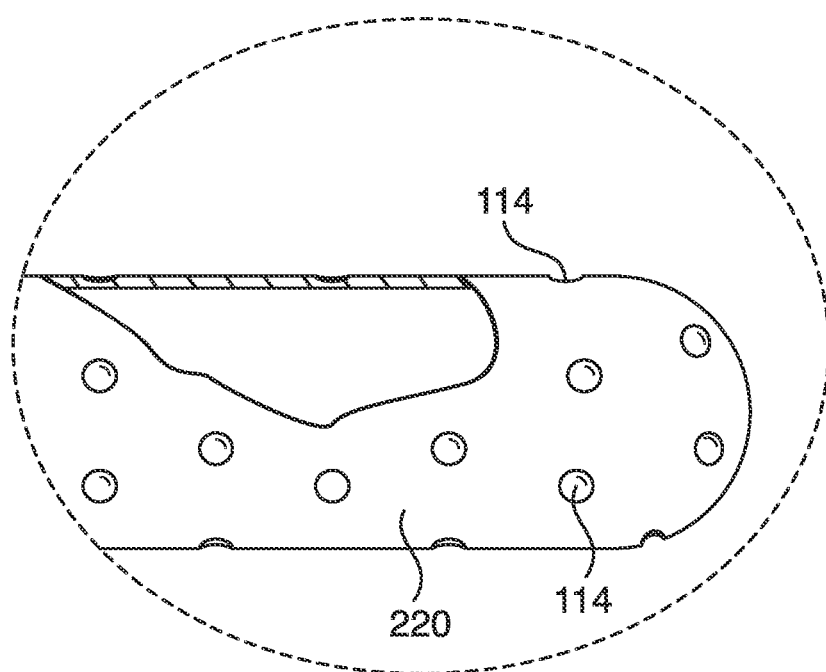
FIGS. 22 and 22A show a side view of the distal end portion of a steerable catheter wherein the biopsy device comprises an echogenic pattern of partially spherical indentations visible via ultrasonic imaging according to an embodiment of the present invention.
Figure 22:
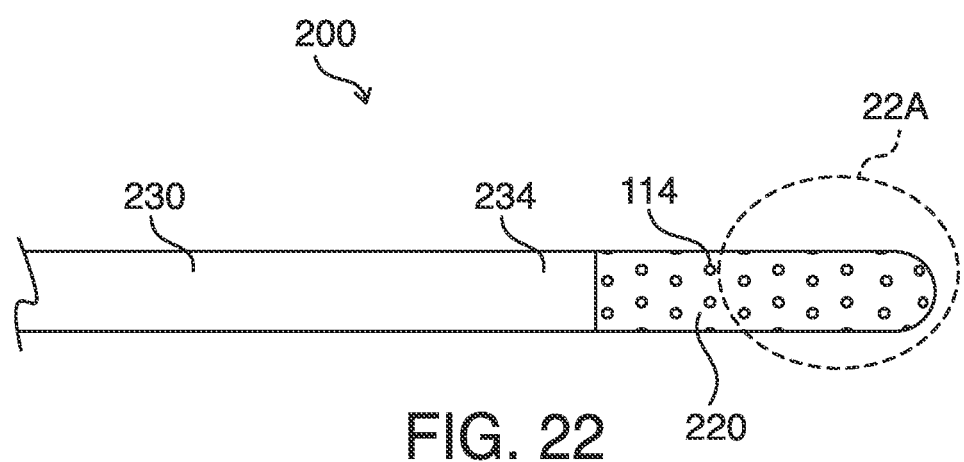
Figure 23A:
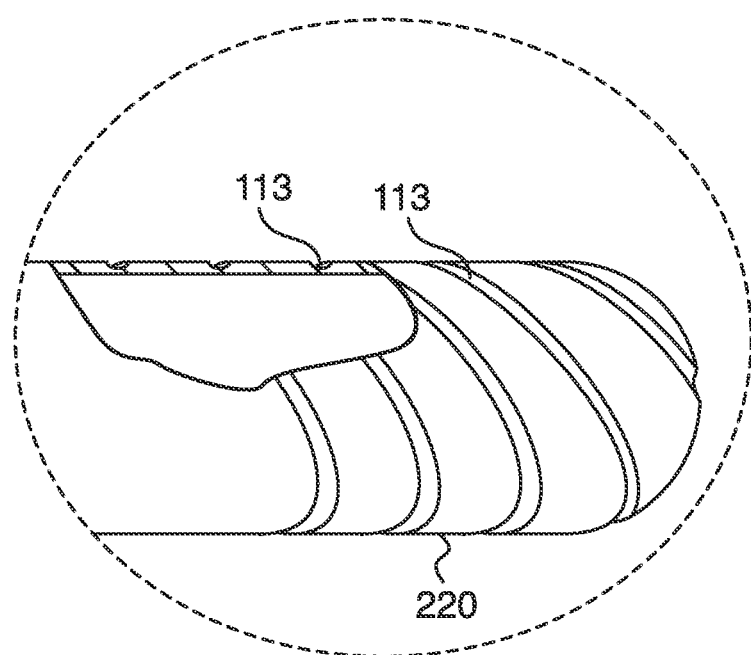
FIGS. 23 and 23A show a side view of the distal end portion of a steerable catheter wherein the biopsy device comprises an echogenic pattern that is visible via ultrasonic imaging according to an embodiment of the present invention.
Figure 23:
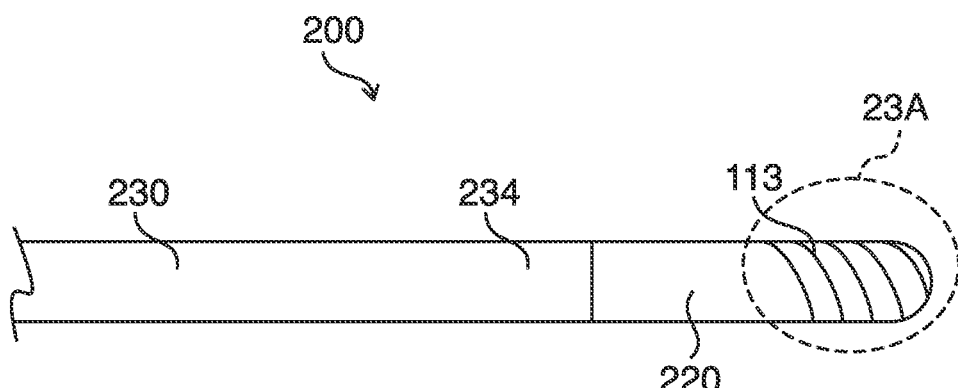

Referring now to FIGS. 22 and 23, in one embodiment biopsy device 220 further comprises an echogenic pattern that may be viewed via ultrasonic imaging. Several approaches of enhancing the ultrasonic signature of medical instruments through modification of the instrument surface reflectivity are known in the prior art and can be applied to embodiments of the present invention. In one embodiment, an echogenic pattern can be positioned around the side wall of biopsy device 220, such that the echogenic pattern fully encompasses the exterior circumference of biopsy device 220. In other embodiments, an echogenic pattern may be at distal end portion 234 of elongate flexible shaft 230. In this embodiment, biopsy device 220 may comprise any of the biopsy devices described elsewhere herein (see, e.g., FIGS. 17A-17G).

Referring now to FIGS. 22 and 22A, the echogenic pattern comprises a plurality of partially spherical indentations 114 on the exterior surface of biopsy device 220, such that the radius of the partially spherical indentations is less than the wavelength of the incident ultrasonic beam. The plurality of partially spherical indentations 114 cause constructive interference of the ultrasonic beam to affect an amplification of the reflecting beam along the line of the incident beam; such amplification may occur at any incident ultrasonic beam angle. In this embodiment, biopsy device 220 may comprise any of the biopsy devices described elsewhere herein (see, e.g., FIGS. 17A-17G).

Referring now to FIGS. 23 and 23A, the echogenic pattern comprises a plurality of grooves 113 cut into the exterior surface of biopsy device 220 that increase the reflective coefficient of biopsy device 220. The plurality of grooves 113 may cause constructive interference of the ultrasonic beam to affect an amplification of the reflecting beam along the line of the incident beam. In this embodiment, biopsy device 220 may comprise any of the biopsy devices described elsewhere herein (see, e.g., FIGS. 17A-17G).

In certain embodiments, as discussed herein, localization element 24 may be positioned at or near the distal end of biopsy device 220. Alternatively, in other embodiments, localization element 24 is positioned at or near the proximal end of biopsy device 220. In yet other embodiments, multiple localization elements 24 (e.g., 5DOF or 6DOF electromagnetic sensors) and/or radiopaque markers, echogenic patterns, etc. may be positioned at or near the proximal end of biopsy device 220. Alternatively, in other embodiments, multiple localization elements 24 (e.g., 5DOF or 6DOF electromagnetic sensors) and/or radiopaque markers, echogenic patterns, etc. may be positioned at or near the distal end of the biopsy device 220. In yet other embodiments, multiple localization elements 24 (e.g., 5DOF or 6DOF electromagnetic sensors) and/or radiopaque markers, echogenic patterns, etc. may be positioned at or near the proximal and distal ends of the biopsy device 220. In another embodiment of the present invention, biopsy device 220 contains no localization element 24. Alternatively, localization element 24 is positioned at or near distal end portion 234 of elongate flexible shaft 230. By positioning localization element 24 at or near distal end portion 234 of elongate flexible shaft 230, in certain embodiments, the biopsy device 220 could be made smaller or at a lesser cost. In this embodiment, biopsy device 220 may comprise any of the biopsy devices described elsewhere herein (see, e.g., FIGS. 17A-17G).

In yet other embodiments, forceps device 300 (see FIG. 17B) may be visible via fluoroscopic imaging wherein an angled or directionally arranged radiopaque marker pattern 115 is at or near the proximal end and/or the distal end of forceps device 300 (see FIGS. 20A, 20B, and 20C). In yet other embodiments, forceps device 300 may be visible via fluoroscopic imaging wherein a radiopaque marker pattern 115 comprising generally circular radiopaque markers 116 is placed around forceps device 300 (see FIGS. 21A, 21B, and 21C). In yet other embodiments, forceps device 300 may be visible via ultrasonic imaging wherein an echogenic pattern comprising a plurality of grooves 113 is in forceps device 300 (see FIG. 23). In yet other embodiments, forceps device 300 may be visible via ultrasonic imaging wherein an echogenic pattern comprising a plurality of partially spherical indentations 114 is in forceps device 300 (see FIG. 22).

Figure 24:
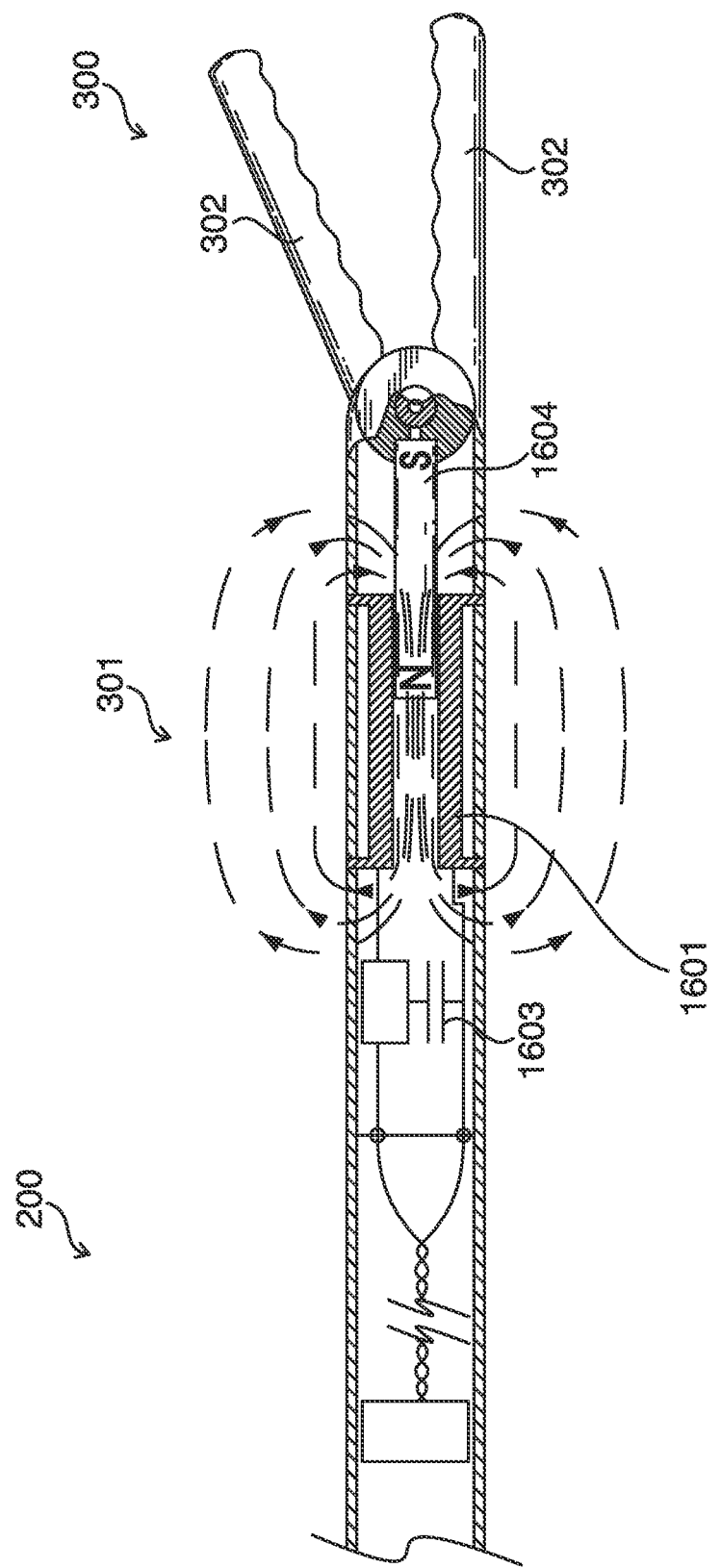
FIG. 24 is a side cutaway view of the distal end portion of a steerable catheter wherein the biopsy device comprises an actuatable sensor-equipped forceps device according to an embodiment of the present invention.

Referring now to FIG. 24, in an alternative embodiment, steerable catheter 200 comprises an alternative forceps device 300 as the biopsy device 220. Instead of a mechanical forceps device actuated by an actuation wire (see FIG. 19), first and second forceps jaws 302 are operated by a solenoid coil 1601. Solenoid coil 1601 is housed within in forceps housing 301 and when the solenoid is in an "active" mode, it is activated by energy stored in capacitor 1603 thereby actuating the first and second forceps jaws 302 via armature 1604. In a "passive" mode solenoid coil 1601 may act as a localization element 24 (e.g., an electromagnetic or other sensor). In other embodiments, other biopsy devices as described elsewhere herein (see, e.g., FIGS. 17A-17G), may be actuated or operated in a similar manner.

Figure 25A:
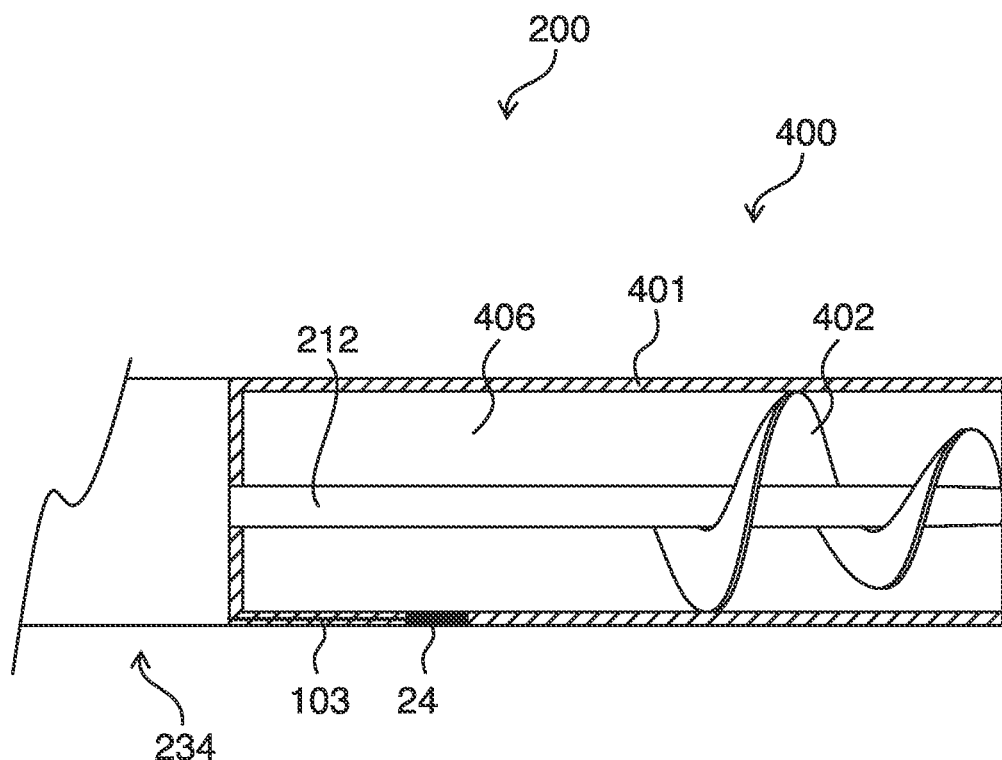
FIGS. 25A and 25B are side cutaway views of the distal end portion of a steerable catheter wherein the biopsy device comprises a navigated auger device according to an embodiment of the present invention.
Figure 25B:
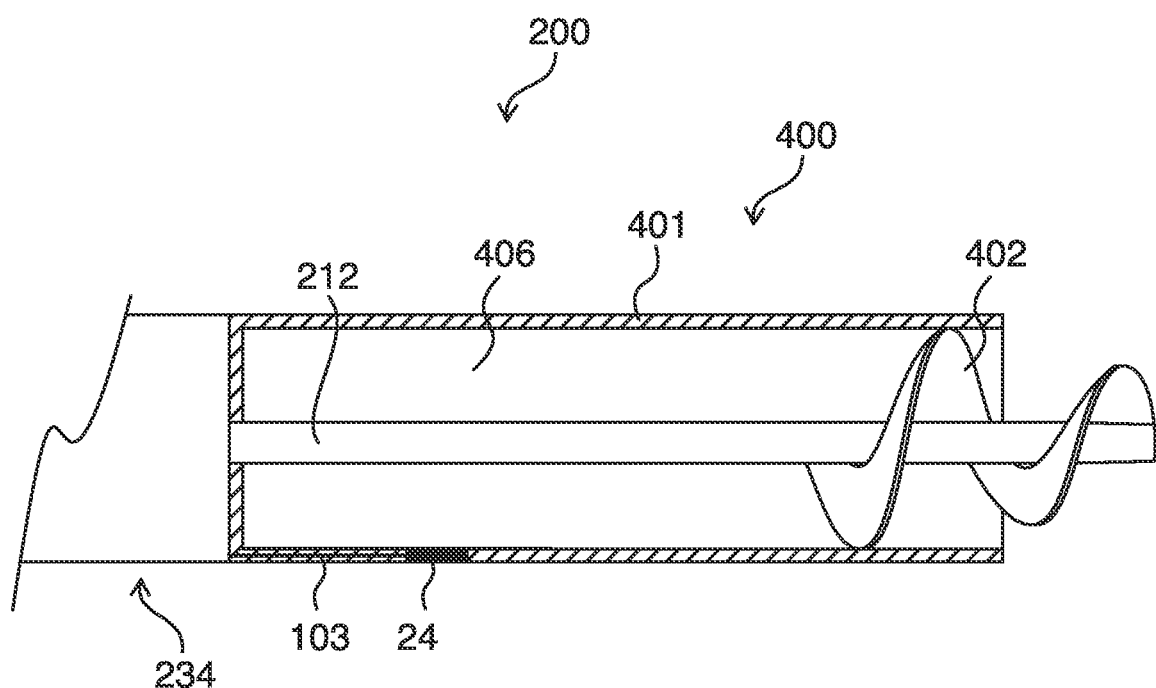
Figure 26A:
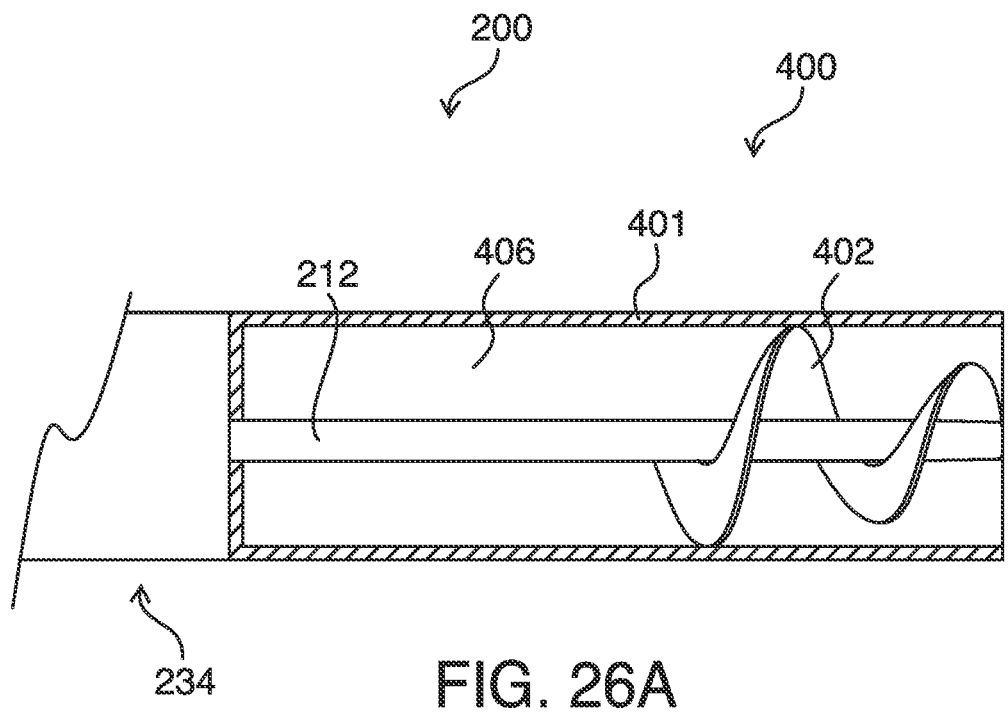
FIGS. 26A and 26B are side cutaway views of the distal end portion of a steerable catheter wherein the biopsy device comprises a non-navigated auger device according to an embodiment of the present invention.
Figure 26B:
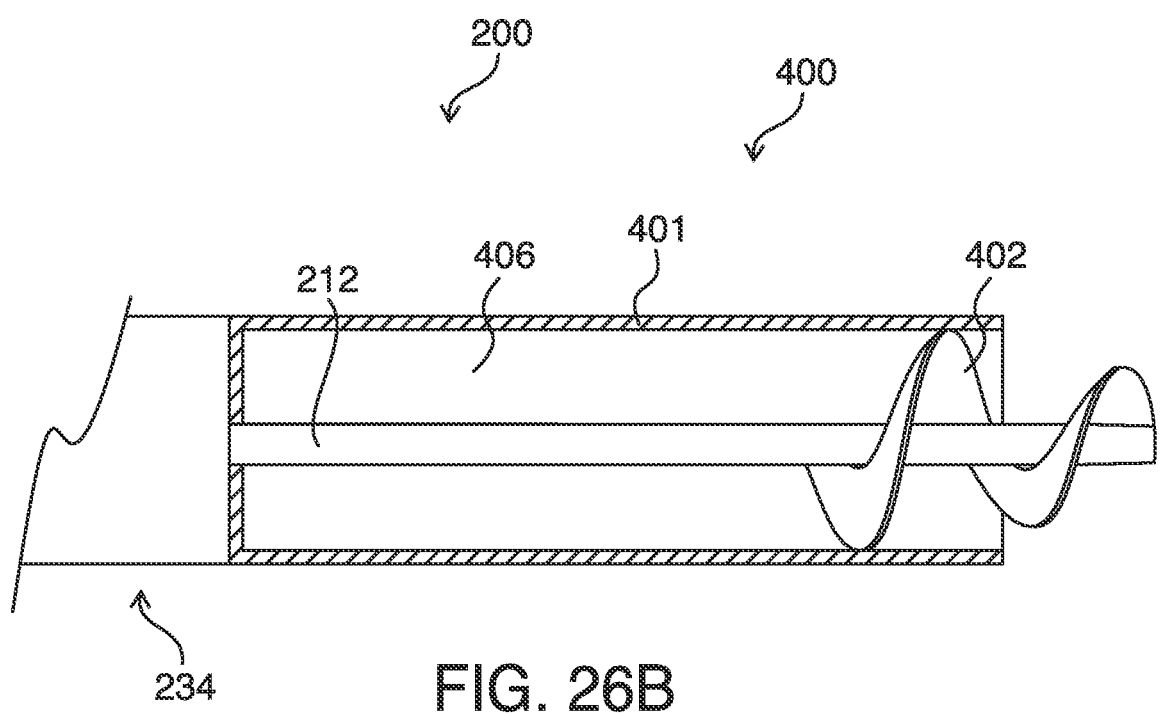

Referring now to FIGS. 25A and 25B, in an alternative embodiment, steerable catheter 200 comprises an auger device 400 as the biopsy device 220. Auger device 400 may be positioned proximate to the region (or tissue) of interest and is adapted to remove tissue from the respiratory system of a patient. In certain embodiments, auger device 400 may comprise an auger bit housing 401, and an auger bit 402 within the auger bit housing 401. Auger bit 402 has a base and a tip, and a tissue collection region 406 at the base of the auger bit 402, wherein the auger bit 402 may be operably connected to the actuation wire 212. Auger bit 402 may be helical in shape. Auger bit housing 401 has a closed proximal end attached to distal end portion 234 of elongate flexible shaft 230 and an open distal end. The proximal end of auger bit housing 401 has a hole through which the actuation wire extends toward the open distal end. In certain embodiments, auger bit housing 401 and auger bit 402 can be made of, for example, stainless steel or other metal, plastic, for example PVC, or from a hard polymeric material. In one particular embodiment, the auger bit 402 has a constant diameter from the base to the tip. In another embodiment, the diameter of auger bit 402 decreases from the base to the tip. In this particular embodiment, as illustrated in FIG. 25B, auger bit 402 is extendable out the open distal end of auger bit housing 401 and rotatable by manipulation of the actuation wire 212 at handle 216 (not shown). Auger device 400 may be navigated via the inclusion of a localization element 24 with a sensor lead 103 extending to proximal end portion 232 of elongate flexible shaft 230. In other embodiments, localization element 24 may be attached to actuation wire 212 such that movement of actuation wire 212 as handle 216 is manipulated causes coordinated movement of localization element 24 thereby providing an indication that auger device 400 is being operated. In other embodiments, localization element 24 may be attached to auger bit 402. Once the target tissue of a patient's respiratory system is reached by steerable catheter 200, the physician or other healthcare professional actuates auger device 400 by manipulating handle 216 which actuates actuating wire 212 thereby causing auger bit 402 to extend and rotate, removing tissue from the patient. Rotation of auger bit 402 draws the removed tissue into the auger bit housing 401 and into tissue collection region 406. In other embodiments, a vacuum pressure may be used to pull the removed tissue into tissue collection region 406. In yet other embodiments as illustrated by FIGS. 26A and 26B, auger device 400 may have no localization element.

Figure 27:
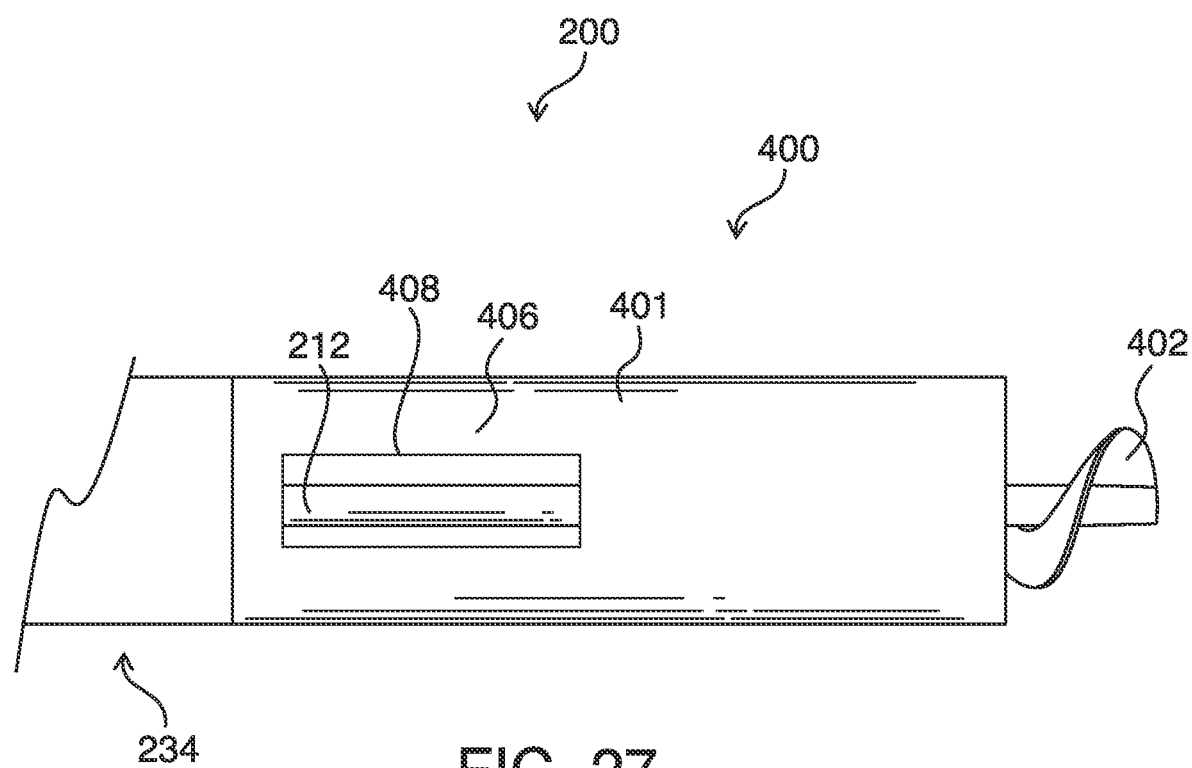
FIG. 27 is a side view of the distal end portion of a steerable catheter wherein the biopsy device comprises an auger device having wherein the tissue collection region comprises a viewing window according to an embodiment of the present invention.

As shown in FIG. 27, in another embodiment of auger device 400, tissue collection region 406 of auger device 400 has a viewing window 408. Viewing window 408 allows for inspection, e.g., via bronchoscope or other viewing or sensing device such as described herein while the steerable catheter 200 is still in the patient's body, of when the tissue collection region 406 is full or a sufficient sample size has been collected. In other embodiments, the removed tissue can be viewed through viewing window 408 after the steerable catheter 200 has been removed from the patient's body or it can be viewed by a bronchoscope inserted into the patient's body.

In yet other embodiments, auger device 400 may be visible via fluoroscopic imaging wherein an angled or directionally arranged radiopaque marker pattern 115 is at or near the proximal end and/or the distal end of auger device 400 (see FIGS. 20A, 20B, and 20C). In yet other embodiments, auger device 400 may be visible via fluoroscopic imaging wherein a radiopaque marker pattern 115 comprising generally circular radiopaque markers 116 is placed around auger device 400 (see FIGS. 21A, 21B, and 21C). In yet other embodiments, auger device 400 may be visible via ultrasonic imaging wherein an echogenic pattern comprising a plurality of grooves 113 is in auger device 400 (see FIG. 23). In yet other embodiments, auger device 400 may be visible via ultrasonic imaging wherein an echogenic pattern comprising a plurality of partially spherical indentations 114 is in auger device 400 (see FIG. 22).

Figure 28A:
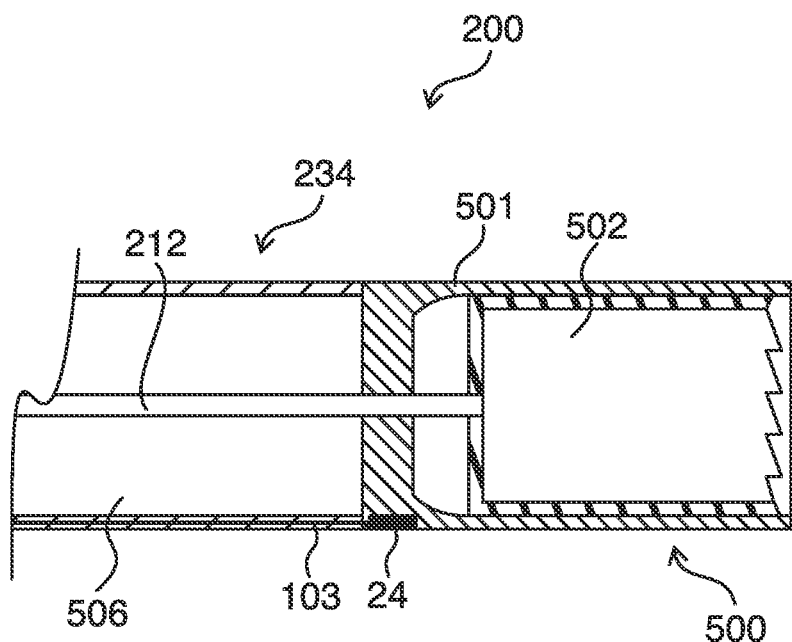
FIGS. 28A and 28B are side cutaway views of the distal end portion of a steerable catheter wherein the biopsy device comprises a navigated boring bit device according to an embodiment of the present invention.
Figure 28B:
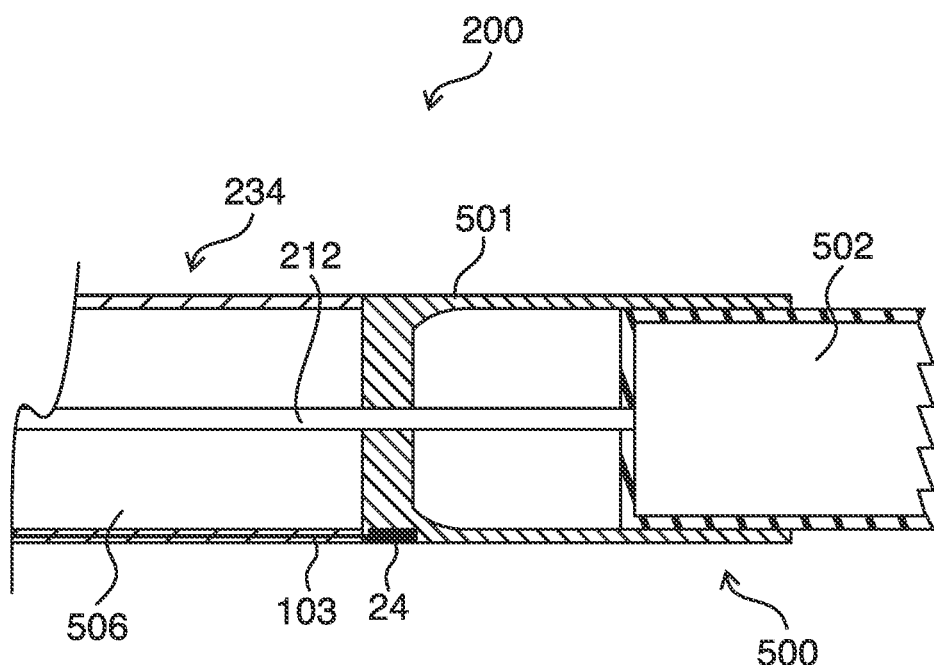
Figure 30A:
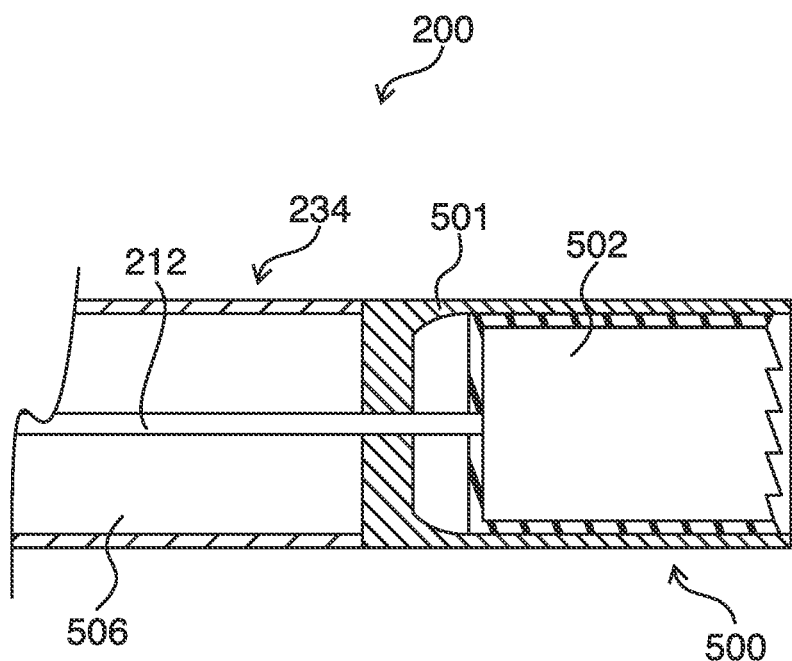
FIGS. 30A and 30B are side cutaway views of the distal end portion of a steerable catheter wherein the biopsy device comprises a non-navigated boring bit according to an embodiment of the present invention.
Figure 30B:
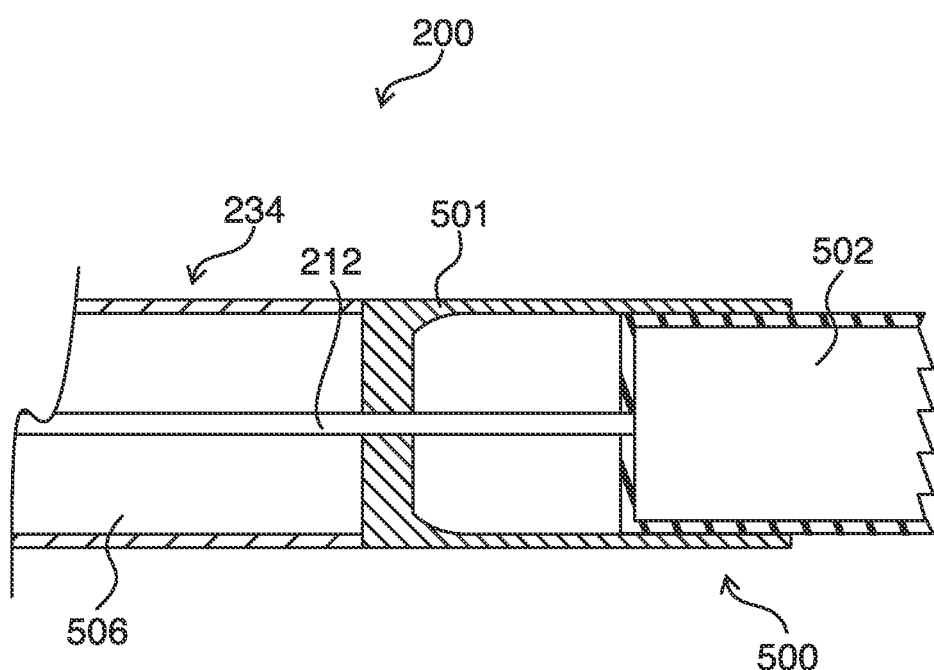

Referring now to FIGS. 28A and 28B, in an alternative embodiment, steerable catheter 200 comprises a boring bit device 500 as the biopsy device 220. Boring bit device 500 may be positioned proximate to the region (or tissue) of interest and is adapted to remove tissue from the respiratory system of a patient. Additionally, in certain embodiments, elongate flexible shaft 200 further comprises a vacuum channel 506. In certain embodiments, boring bit device 500 may comprise a boring bit housing 501 and a boring bit 502 within boring bit housing 501. Boring bit 502 may comprise a hollow cylinder having a closed proximal end and an open distal end having a plurality of cutting teeth around the circumference of the cylinder, wherein boring bit 502 may be operably connected to actuation wire 212. Boring bit housing 501 and boring bit 502 can be made of, for example, stainless steel or other metal, plastic, for example PVC, or from a hard polymeric material. Boring bit device 500 may be navigated via the inclusion of an attached localization element 24 with a sensor lead 103 extending to the proximal end portion 232 of elongate flexible shaft 230. In other embodiments, localization element 24 may be attached to actuation wire 212 such that movement of actuation wire 212 as handle 216 is manipulated causes coordinated movement of localization element 24 thereby providing an indication that boring bit device 500 is being operated. In other embodiments, localization element 24 may be attached to boring bit 502. In this particular embodiment, as illustrated in FIG. 28B, boring bit 502 is extendable out the open distal end of boring bit housing 501 and rotatable by manipulation of the actuation wire 212 at handle 216 (not shown). Once the target tissue of a patient's respiratory system is reached by steerable catheter 200, the physician or other healthcare professional actuates boring bit device 500 by manipulating handle 216 which actuates actuating wire 212 thereby causing boring bit 502 to extend and rotate, removing tissue from the patient. In certain embodiments, boring bit device 500 may also comprise a tissue collection region where the removed tissue can be collected. In yet other embodiments, tissue collection region of boring bit device 500 may have a viewing window through which the removed tissue can be inspected from outside boring bit device 500 (see FIG. 27). In certain embodiments, boring bit device 500 may have no localization element as illustrated in FIGS. 30A and 30B.

Figure 29:
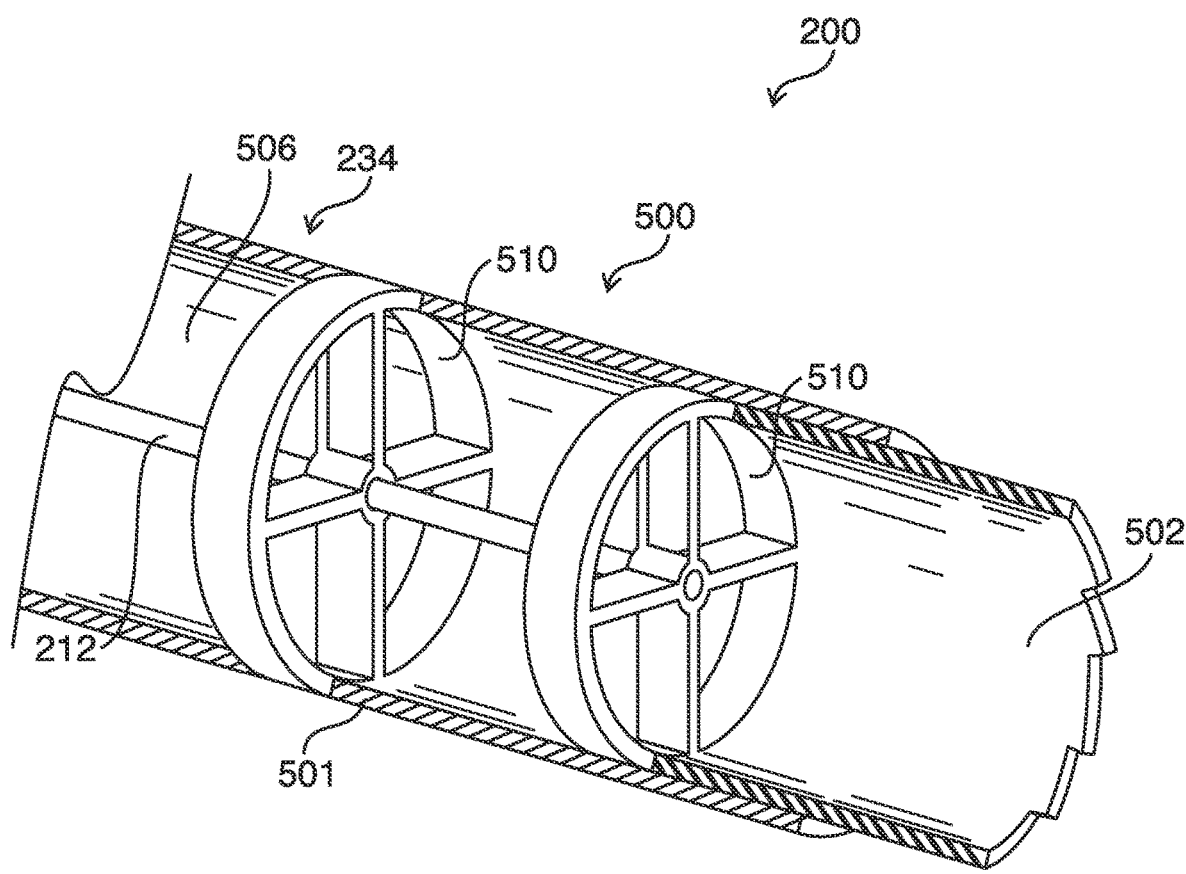
FIG. 29 is a side perspective cutaway view of the distal end portion of a steerable catheter wherein the biopsy device comprises a boring bit device according to an embodiment of the present invention.

FIG. 29 illustrates another embodiment where, boring bit housing 501 may have at least one opening 510 in the proximal end attached to distal end portion 234 of elongate flexible shaft 230 and an open distal end through which the boring bit 502 is extended. Additionally, in this embodiment, the proximal end of boring bit 502 may have at least one opening 510. The proximal end of boring bit housing 501 has a hole through which the actuation wire 212 extends toward the open distal end. In this particular embodiment, boring bit 502 is extendable out the open distal end of the boring bit housing 501 and rotatable by manipulation of the actuation wire 212 at handle 216 (not shown). Once the target tissue of a patient's respiratory system is reached by the steerable catheter 200, the physician or other healthcare professional actuates boring bit device 500 by manipulating handle 216 which actuates actuating wire 212 thereby causing boring bit 502 to extend and rotate, removing tissue from the patient. Additionally, a vacuum pressure may be applied at proximal end portion 232 of elongate flexible shaft 230 wherein this pressure acts on the vacuum channel 506, the at least one opening 510 in the proximal end of boring bit housing 501, and the at least one opening 510 in the proximal end of boring bit 502 to aid in the removal of the patient's tissue. In other embodiments, wherein boring bit device 500 may further comprise a tissue collection region, the applied vacuum pressure may be used to pull the removed tissue into tissue collection region.

Figure 31A:
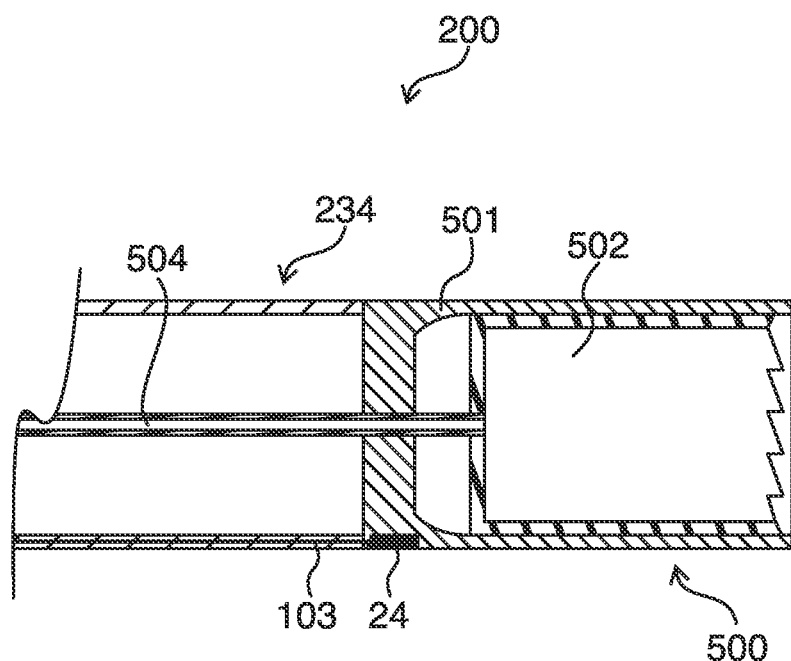
FIGS. 31A and 31B are side cutaway views of the distal end portion of a steerable catheter wherein the biopsy device comprises a navigated boring bit device wherein the actuation wire is hollow and to which a vacuum pressure is applied to assist in the removal of tissue according to an embodiment of the present invention.
Figure 31B:
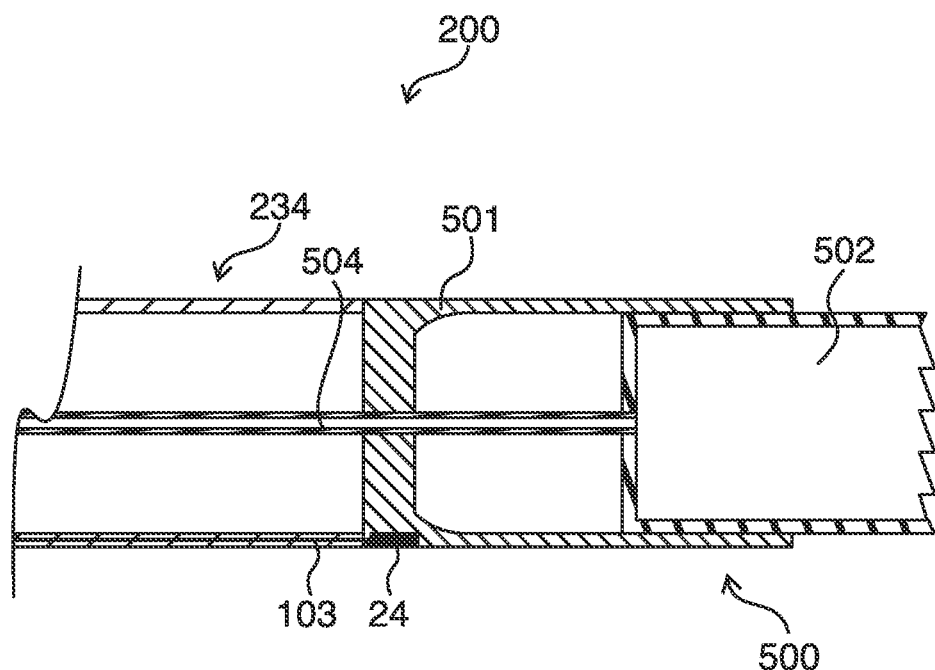
Figure 32:
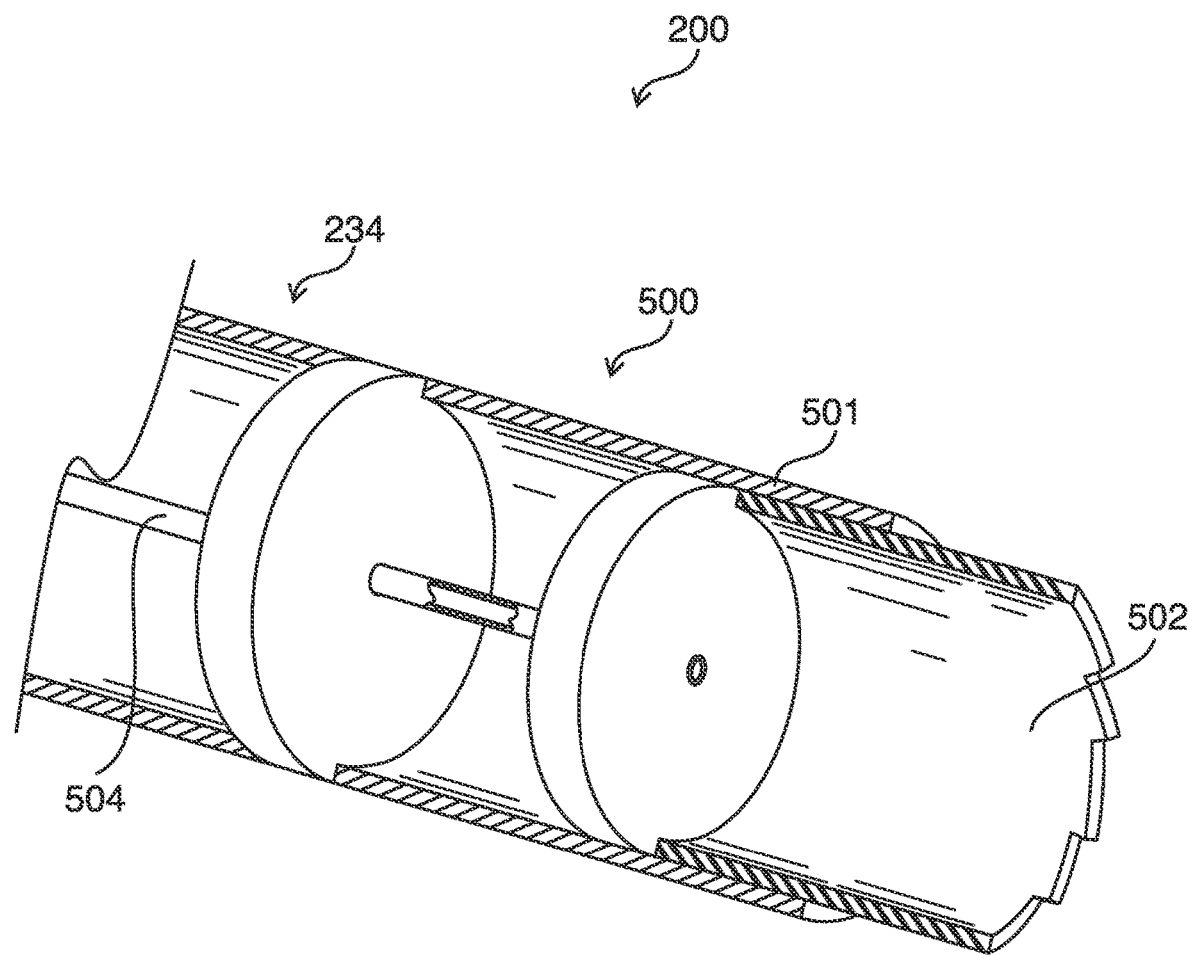
FIG. 32 is a side perspective cutaway view of the distal end portion of a steerable catheter wherein the biopsy device comprises a boring bit device wherein the actuation wire is hollow and to which a vacuum pressure is applied to assist in the removal of tissue according to an embodiment of the present invention.

In another embodiment, as illustrated by FIGS. 31A and 31B, boring bit housing 501 has closed proximate end attached to the distal end portion 234 of elongate flexible shaft 230 and an open distal end through which boring bit 502 is extended. The proximal end of boring bit housing 501 has a hole through which the actuation wire 504 extends toward the open distal end. Additionally, in this embodiment, actuation wire 504 is hollow. In this particular embodiment, as illustrated in FIG. 32, boring bit 502 is extendable out the open distal end of boring bit housing 501 and rotatable by manipulation of hollow actuation wire 504 at handle 216. Once the target tissue of a patient's respiratory system is reached by steerable catheter 200, the physician or other healthcare professional actuates the boring bit device 500 by manipulating handle 216 which actuates hollow actuating wire 504 thereby causing boring bit 502 to extend and rotate, removing tissue from the patient. Additionally, a vacuum pressure may be applied at proximal end portion 232 of elongate flexible shaft 230 wherein this pressure acts on hollow actuation wire 504 to aid in the removal of the patient's tissue.

In yet other embodiments, boring bit device 500 may be visible via fluoroscopic imaging wherein an angled or directionally arranged radiopaque marker pattern 115 is at or near the proximal end and/or the distal end of boring bit device 500 (see FIGS. 20A, 20B, and 20C). In yet other embodiments, boring bit device 500 may be visible via fluoroscopic imaging a radiopaque marker pattern 115 comprising generally circular radiopaque markers 116 is placed around boring bit device 500 (see FIGS. 21A, 21B, and 21C). In yet other embodiments, boring bit device 500 may be visible via ultrasonic imaging wherein an echogenic pattern comprising a plurality of grooves 113 is in boring bit device 500 (see FIG. 23). In yet other embodiments, boring bit device 500 may be visible via ultrasonic imaging wherein an echogenic pattern comprising a plurality of partially spherical indentations 114 is in boring bit device 500 (see FIG. 22).

Figure 33:
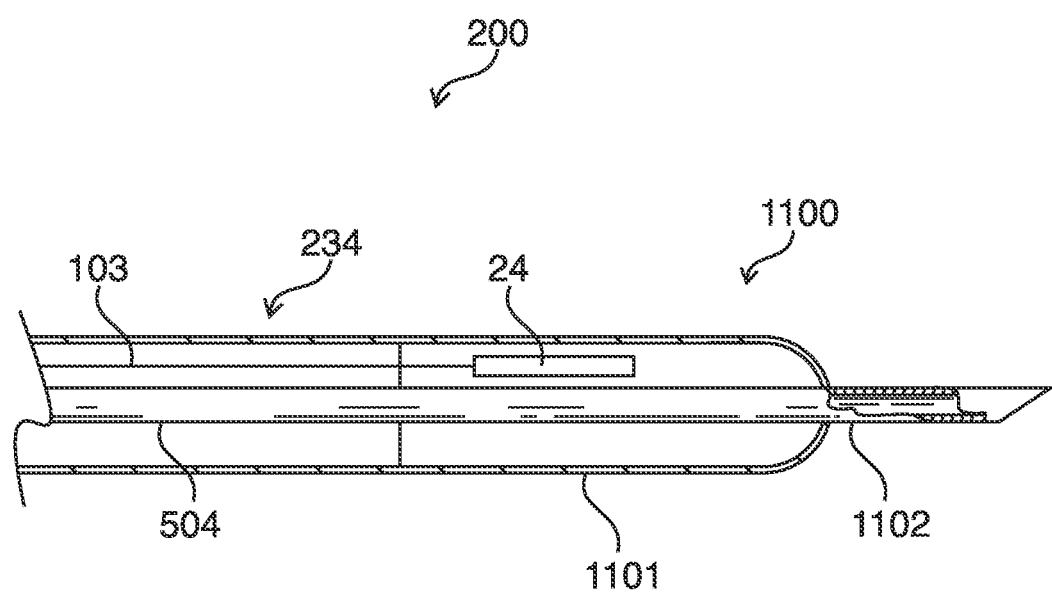
FIG. 33 is a side cutaway view of the distal end portion of a steerable catheter wherein the biopsy device comprises an aspiration needle according to an embodiment of the present invention.

Referring now to FIG. 33, in an alternative embodiment, steerable catheter 200 comprises an aspiration needle device 1100 as the biopsy device 220. Aspiration needle device 1100 may be positioned proximate to the region (or tissue) of interest and is adapted to remove tissue from the respiratory system of a patient. In certain embodiments, aspiration needle device 1100 may comprise an aspiration needle housing 1101 and an aspiration needle 1102 within aspiration needle housing 1101. Aspiration needle device 1100 may be navigated via the inclusion of an attached localization element 24 with a sensor lead 103 extending to proximal end portion 232 of elongate flexible shaft 230. In other embodiments, localization element 24 may be attached to hollow actuation wire 504 such that movement of hollow actuation wire 504 as handle 216 is manipulated causes coordinated movement of localization element 24 thereby providing an indication that aspiration needle device 1100 is being operated. In other embodiments, localization element 24 may be attached to aspiration needle 1102. In certain embodiments, aspiration needle device 1100 may have no localization element. In certain embodiments, aspiration needle 1102 may be between 18 and 22 ga. Aspiration needle housing 1101 and aspiration needle 1102 can be made of, for example, nitinol, stainless steel or other metal, plastic, for example PVC, or from a hard polymeric material. In certain embodiments, aspiration needle 1102 may be a flexible needle. In other embodiments, aspiration needle 1102 may be a relatively rigid (non-flexible) needle. In yet other embodiments, aspiration needle 1102 may comprise a shape memory alloy, as described in greater detail elsewhere herein. There are a number of mechanically operated aspiration needle devices that are known in the prior art and can be adapted to operably connect to a hollow actuation wire of the steerable catheter 200. In additional embodiments, the aspiration needle device comprises a single biopsy device that is attached at the proximal end portion 232 of elongate flexible shaft 230 and extends to the distal end portion 234 of elongate flexible shaft 232. Aspiration needle device 1100 may be navigated via the inclusion of an attached localization element 24 with a sensor lead 103 extending to proximal end portion 232 of elongate flexible shaft 230. Once the target tissue of a patient's respiratory system is reached by steerable catheter 200, the physician or other healthcare professional actuates aspiration needle device 1100 by manipulating handle 216 which actuates the actuating wire 504 thereby causing aspiration needle 1102 to extend and pierce tissue in the patient. Additionally, a vacuum pressure may be applied at proximal end portion 232 of elongate flexible shaft 230 wherein this pressure acts on hollow actuation wire 504 to aid in the removal of the patient's tissue. In another embodiments, aspiration needle device 1100 comprises a single biopsy device that is attached at proximal end portion 232 of elongate flexible shaft 230 and extends to distal end portion 234 of elongate flexible shaft 230, the physician or other healthcare professional actuates aspiration needle device 1100 by manipulating handle 216 which causes aspiration needle 502 to extend and pierce tissue from the patient. Additionally, a vacuum pressure may be applied at proximal end portion 232 of elongate flexible shaft 230 wherein this pressure acts on aspiration needle 1102 to aid in the removal of the patient's tissue. In certain embodiments, aspiration needle device 1100 may also comprise a tissue collection region where the removed tissue can be collected. In other embodiments, the applied vacuum pressure may be used to pull the removed tissue into tissue collection region. In yet other embodiments, tissue collection region of aspiration needle device 1100 may have a viewing window through which the removed tissue can be inspected from outside aspiration needle device 1100 (see FIG. 27).

In yet other embodiments, aspiration needle device 1100 may be visible via fluoroscopic imaging wherein an angled or directionally arranged radiopaque marker pattern 115 is at or near the proximal end and/or the distal end of aspiration needle device 1100 (see FIGS. 20A, 20B, and 20C). In yet other embodiments, aspiration needle device 1100 may be visible via fluoroscopic imaging wherein a radiopaque marker pattern 115 comprising generally circular radiopaque markers 116 is placed around aspiration needle device 1100 (see FIGS. 21A, 21B, and 21C). In yet other embodiments, aspiration needle device 1100 may be visible via ultrasonic imaging wherein an echogenic pattern comprising a plurality of grooves 113 is in aspiration needle device 1100 (see FIG. 23). In yet other embodiments, aspiration needle device 1100 may be visible via ultrasonic imaging wherein an echogenic pattern comprising a plurality of partially spherical indentations 114 is in aspiration needle device 1100 (see FIG. 22).

Figure 34A:
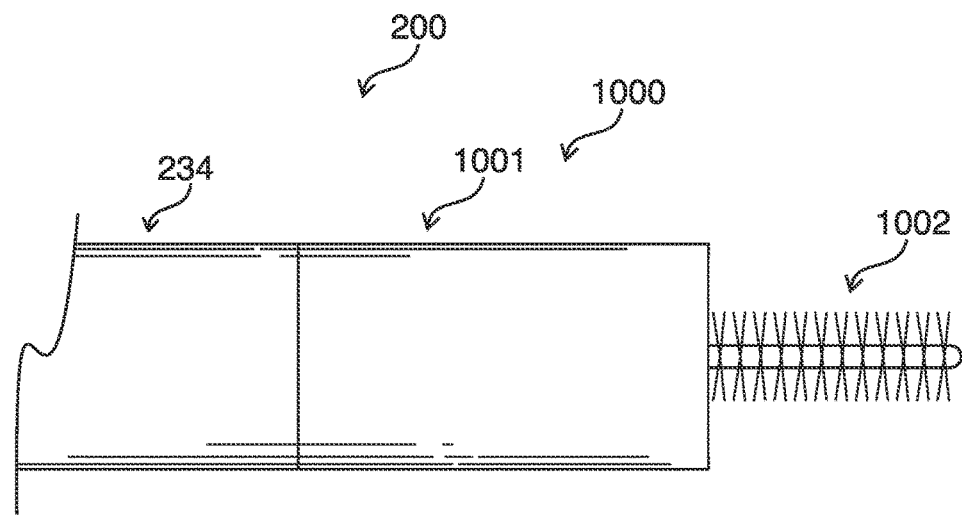
FIGS. 34A and 34B show a side view and a side perspective cutaway view of the distal end portion of a steerable catheter wherein the biopsy device comprises a brush device according to an embodiment of the present invention.
Figure 34B:
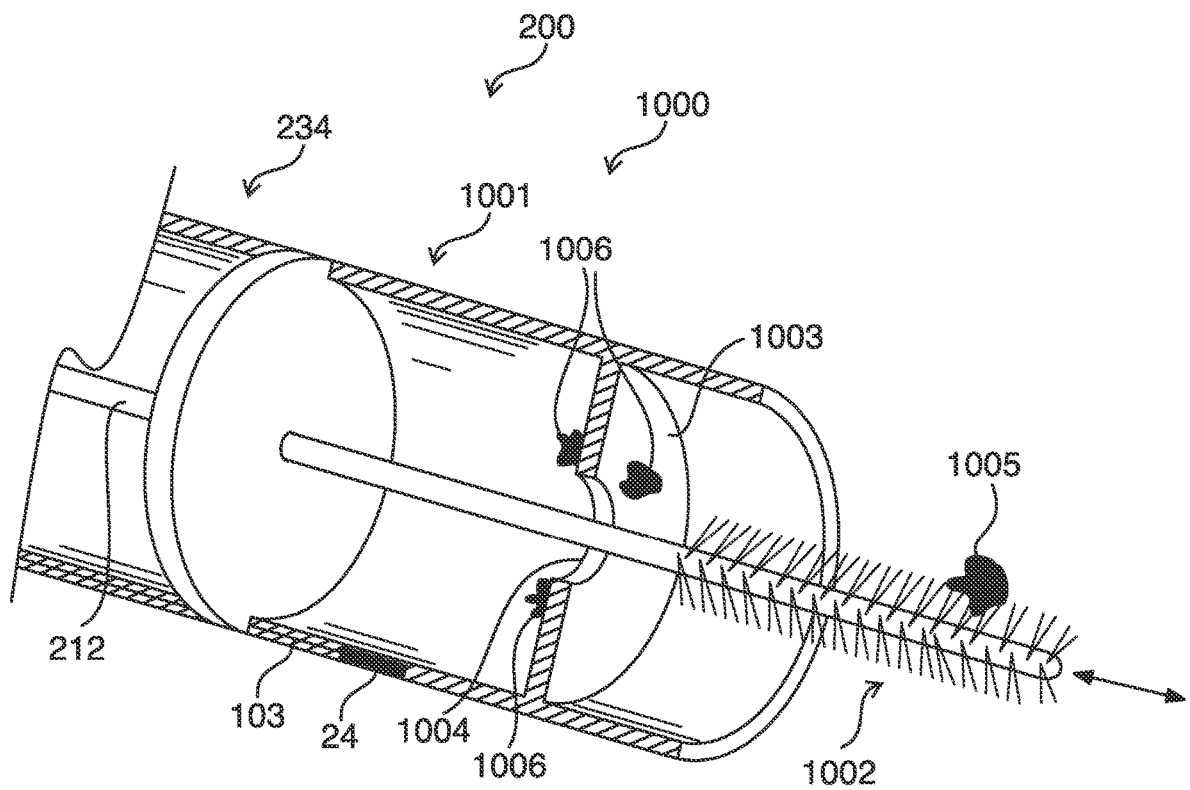

Referring now to FIGS. 34A and 34B, in an alternative embodiment, steerable catheter 200 comprises a brush device 1000 as the biopsy device 220. Brush device 1000 may be positioned proximate to the region (or tissue) of interest and is adapted to remove tissue from the respiratory system of a patient. In certain embodiments, brush device 1000 may comprise a brush housing 1001 and a brush 1002 wherein brush 1002 comprises a plurality of bristles affixed to an actuation wire 212. Brush housing 1001 may have a closed proximal end attached to the distal end portion 234 of elongate flexible shaft 230 and an open distal end. Additionally brush housing 1001 may have an internal wall 1003 with an aperture 1004 having a diameter less than that of the diameter of brush 1002. The proximal end of brush housing 1001 has a hole through which the actuation wire 212 extends toward the open distal end. Brush housing 1001 can be made of, for example, stainless steel or other metal, plastic, for example PVC, or from a hard polymeric material. Brush 1002 is extendable out the open distal end of brush housing 1001 and rotatable by manipulation of the actuation wire 212 at handle 216. Brush device 1000 may be navigated via the inclusion of an attached localization element 24 with a sensor lead 103 extending to proximal end portion 232 of elongate flexible shaft 230. In other embodiments, localization element 24 may be attached to actuation wire 212 such that movement of actuation wire 212 as handle 216 is manipulated causes coordinated movement of localization element 24 thereby providing an indication that brush device 1000 is being operated. In other embodiments, localization element 24 may be attached to brush 1002. In certain embodiments, brush device 1000 may have no localization element. Once the target tissue of a patient's respiratory system is reached by steerable catheter 200, the physician or other healthcare professional actuates brush device 1000 by manipulating handle 216 which actuates actuating wire 212 thereby causing brush 1002 to extend and rotate, removing tissue 1005 from the patient. The physician or other healthcare professional may then withdraw brush 1002 into brush housing 1001 whereby removed tissue 1006 is scraped from brush 1002 by aperture 1004. Additionally, in another embodiment, elongate flexible shaft 230 further comprises a vacuum channel and the proximal end of brush housing 1001 further comprises at least one hole to which a vacuum pressure can be applied. Additionally, a vacuum pressure may be applied at proximal end portion 232 of elongate flexible shaft 230 wherein this pressure acts on the vacuum channel and the at least one opening in the proximal end of brush housing 1001 to aid in the removal of the patient's tissue. In certain embodiments, brush device 1000 may also comprise a tissue collection region where the removed tissue can be collected. In other embodiments, the applied vacuum pressure may be used to pull the removed tissue into tissue collection region. In yet other embodiments, tissue collection region of brush device 1000 may have a viewing window through which the removed tissue can be inspected from outside brush device 1000 (see FIG. 27).

In yet other embodiments, brush device 1000 may be visible via fluoroscopic imaging wherein an angled or directionally arranged radiopaque marker pattern 115 is at or near the proximal end and/or the distal end of brush device 1000 (see FIGS. 20A, 20B, and 20C). In yet other embodiments, brush device 1000 may be visible via fluoroscopic imaging wherein a radiopaque marker pattern 115 comprising generally circular radiopaque markers 116 is placed around brush device 1000 (see FIGS. 21A, 21B, and 21C). In yet other embodiments, brush device 1000 may be visible via ultrasonic imaging an echogenic pattern comprising a plurality of grooves 113 is in brush device 1000 (see FIG. 23). In yet other embodiments, brush device 1000 may be visible via ultrasonic imaging wherein an echogenic pattern comprising a plurality of partially spherical indentations 114 is in brush device 1000 (see FIG. 22).

In another embodiment of a brush device, as brush is pushed out of the brush housing the brush is squeezed through a smaller opening to collect the sampled tissue that was trapped when extended. When fully extended, the brush device end would be open so that the brush can be retracted and the sampled tissue can be pulled into the instrument. The brush device would then close as the brush is extended out and the sampled tissue could be scraped/squeezed from the brush bristles and collected in a reservoir. In certain embodiments, a vacuum pressure may be added to this device in conjunction or in lieu of the scrapping process to clean the brush.

In yet another embodiment, biopsy device 220 is extendable is extendable along a path from a position within the outer wall 236 through a side exit to a position outside the outer wall 236 at an angle of at least 30 degrees relative to the longitudinal axis, wherein the path of biopsy device 220 can be calibrated to the location of an electromagnetic localization sensor positioned at the distal end portion of the elongate flexible shaft and displayed by a surgical instrument navigation system. Various embodiments of biopsy devices exiting from the side of the elongate catheter body can be seen in FIG. 37.

In these and other embodiments, a portion of biopsy device 220 may be bent at an angle relative longitudinal axis 207. A bend in biopsy device 220, may allow the physician or other healthcare professional to rotate biopsy device 220 and sample the region (or tissue) of interest via several different pathways or positions. This may also increase the amount of region (or tissue) of interest that may be sampled in a single pass, and may improve targeting of regions (or tissue) of interest to be sampled. Moreover, a bend in biopsy device 220 may assist in targeting a region that is not necessarily directly in a patient pathway (e.g., an airway), but may be next to the pathway, thus enabling the physician or other healthcare professional to direct biopsy device 220 to a desired location off the axis of the airway.

The method or procedure of guiding the steerable catheter 200 of certain embodiments to a desired target tissue in the respiratory system of a patient comprises: (i) inserting a flexible lumen into the patient, (ii) inserting into the flexible lumen steerable catheter 200, (ii) navigating steerable catheter 200 through the respiratory system of the patient, (iii) manipulating steering actuator 218 to cause a deflection in longitudinal axis 207, and (iv) performing a medical procedure at the region (or tissue) of interest. In embodiments where steerable catheter 200 is a navigated catheter, the method or procedure of guiding the steerable catheter 200 of certain embodiments to a desired target tissue of a patient includes the additional steps of: (i) displaying an image of the region of the patient, (ii) detecting a location and orientation of localization element 24, and (iii) displaying, in real-time, biopsy device 220 on the image by superimposing a virtual representation of steerable catheter 200 and biopsy device 220 on the image based upon the location and orientation of localization element.

A method or procedure of guiding steerable catheter 200 of certain embodiments to a desired target tissue in the respiratory system of a patient may comprise inserting a flexible lumen into the patient, and inserting into the flexible lumen steerable catheter 200. Steerable catheter 200 may then be navigated to the region of interest and steering actuator 218 may be manipulated to cause a deflection in longitudinal axis 207. Medical procedure may then be performed at the region (or tissue) of interest. In embodiments where steerable catheter 200 is a navigated catheter, the method or procedure of guiding steerable catheter 200 of certain embodiments to a region (or tissue) of interest may comprise the additional steps of displaying an image of the region (or tissue) of interest and detecting a location and orientation of localization element 24. Then biopsy device 220 may be displayed, in real-time, on the image by superimposing a virtual representation of steerable catheter 200 and biopsy device 220 on the image based upon the location and orientation of localization element 24.

In one embodiment of the present invention, surgical instrument 12 (see FIG. 1) comprises a surgical catheter having a side exit (referred to herein as "side exiting catheter") which may be used in a medical procedure to gain access to, manipulate, remove or otherwise treat tissue within the body including, for example, heart or lung tissue. Generally, surgical catheters of the present invention have a distal end portion which can be remotely manipulated via a proximally located handle.

Figure 35:
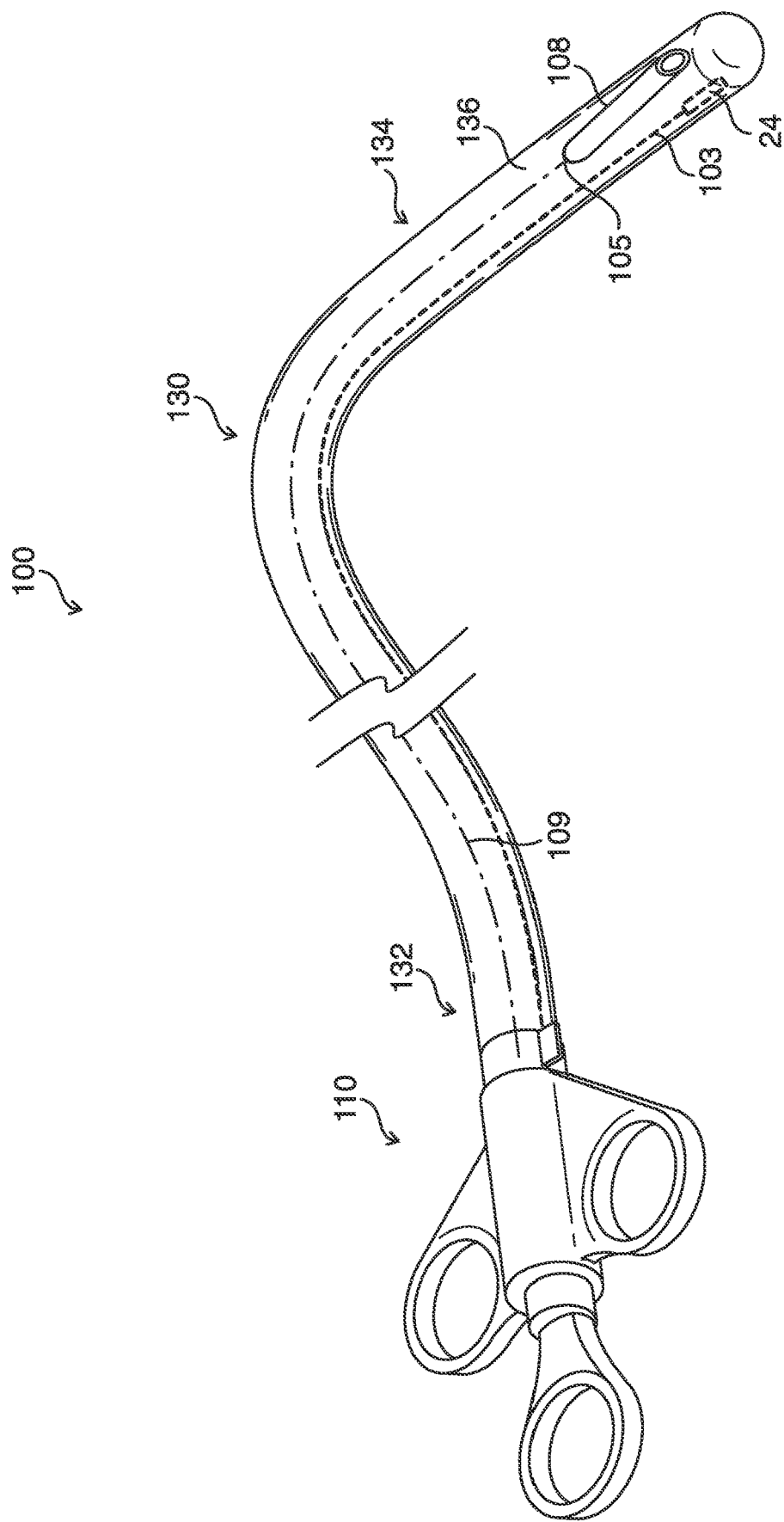
FIG. 35 is a front perspective view of the surgical catheter with a side exiting medical instrument according to an embodiment of the present invention.

In accordance with one embodiment of the present invention and referring now to FIG. 35, side exiting catheter 100 comprises actuating handle 110 and elongate flexible shaft 130. Elongate flexible shaft 130 has proximal end portion 132, distal end portion 134, longitudinal axis 109 extending from proximal end portion 132 to distal end portion 134, outer wall 136 comprising a biocompatible material extending from proximal end portion 132 to distal end portion 134, and a side exit 105 at distal end portion 134 of elongate flexible shaft. In certain embodiments, the biocompatible material is a biocompatible polymer. The stiffness properties of elongate flexible shaft 130 allow elongate flexible shaft 130 to be advanced in patient 13 in a desired direction to a desired region (or tissue of interest) via the application of torsional or linear force applied to handle 110 at proximal end portion 132 of elongate flexible shaft 134.

A localization element 24 may be positioned at distal end portion 134 of elongate flexible shaft 130. In general any of a number of localization elements 24 may be used, including, but not limited to, for example, electromagnetic sensors, radiopaque markers visible via fluoroscopic imaging, or echogenic materials or patterns that increase visibility of the tip component under an ultrasonic beam. In this embodiment, localization element 24 comprises a six (6) degree of freedom (6DOF) electromagnetic sensor. In other embodiments, localization element 24 comprises a five (5) degree of freedom (5DOF) electromagnetic sensor. A localization element lead 103 extends from localization element 24 to proximal end portion 132 of elongate flexible shaft 130. In an alternative embodiment, localization element 24 and the electromagnetic field generator may be reversed, such that localization element 24 positioned at distal end portion 134 of elongate flexible shaft 130 emits a magnetic field that is sensed by external sensors.

Side exiting catheter 100 further comprises medical instrument 108 that may be extended from a position within outer wall 136 and through side exit 105 to a position outside outer wall 136 of elongate flexible shaft 130 by manipulation of handle 110. For ease of illustration, only the portion of medical instrument 108 that is extended outside elongate flexible shaft 130 appears in FIG. 35; the remaining portion of medical instrument 108 which is attached to handle 110 is hidden from view (see FIGS. 51A and 51B). In one embodiment, medical instrument 108 extends through side exit 105 along a path at an angle of at least 10 degrees relative to longitudinal axis 109.

In certain embodiments, by using localization element 24 (which in certain embodiments comprises a 6DOF sensor as described herein), the physician or other healthcare professional can have the location and direction of side exit 105 of elongate flexible shaft 130 displayed by surgical instrument navigation system 10. A real time two- or three-dimensional virtual reconstruction of side exit 105 and several centimeters of distal end portion 132 of elongate flexible shaft 130 may be displayed by surgical instrument navigation system 10. Visualization of the location and orientation of side exit 105 may allow for more intuitive advancement of side exiting catheter 100 to a region (or tissue) of interest. An image plane may be generated that is at side exit 105, as opposed to a point or position distal to distal end portion 134 of elongate flexible shaft 130. In certain embodiments, this may allow easier targeting of lesions, or other region(s) (or tissue) of interest, that may not be directly in the airway or other pathways, but rather partially or even completely outside of the airway or other pathways. In accordance with an exemplary method of using the device, side exiting catheter 100 may be steered slightly past the region (or tissue) of interest to align side exit 105. Medical instrument 108 (e.g., forceps, needle, brush, fiducial delivery device, etc.) may then be extended out elongate flexible shaft 130 through side exit 105. The directional aspect of distal end portion 134 and medical instrument 108 can be viewed on display 18 (see FIG. 1) and a simulated medical instrument can be shown to demonstrate to the physician or other healthcare professional which region (or tissue) of interest will be sampled. These applications may be particularly useful in the sampling of lymph nodes that are outside the patient airways. In some embodiments, for example, side exiting catheter 100 may be capable of creating an endobronchial ultrasound (EBUS)-like view. For example, an image plane oriented with side exit 105 plane may be created and medical instrument 108 may be shown sampling the region (or tissue) of interest on this plane. In various alternative embodiments, the image(s) may be oriented in a plane or orthogonally. Additionally in other embodiments, various curve fitting algorithms may be provided based upon the type and flexibility of the elongate flexible shaft used. These algorithms enable estimated curved trajectories of elongate flexible shaft 130 to be displayed to assist the physician or other healthcare professional.

In accordance with another embodiment, systems and methods may be used to provide the initial location of a localization element (e.g., an electromagnetic sensor) in a surgical instrument (e.g., a steerable surgical catheter, a side exiting catheter, a steering or shape sensing device such as a robotic articulating arm, fiber optic shape tracking device, or micro-actuator/flex systems, etc.). In one embodiment, a calibration jig system may be employed. The calibration jig system comprises at least three reference localization elements (e.g., electromagnetic sensors) positioned substantially in a plane and a tool/calibration channel may be positioned in a known location relative to the localization element plane. A surgical instrument may then be inserted into the tool/calibration channel and the surgical instrument pathway shape may be recorded along with the localization element(s) (e.g., 5DOF and/or 6DOF electromagnetic sensors) in the surgical instrument with respect to the location of the reference localization elements in the localization element plane. By using this calibration jig system, the alignment of the localization element(s) within the surgical instrument may be determined relative to the alignment of the surgical instrument. Additionally, or alternatively, other sensing mechanisms that report position and/or shape can be correlated relative to the reference localization element coordinates and therefore may define the complete or substantially complete physical coordinate system. Because the position of the jig tool channel is known relative to the position of the reference localization elements, the position of sensing mechanisms placed within the surgical instrument may be determined relative to the calibration jig and therefore relative to each other.

Figure 36:
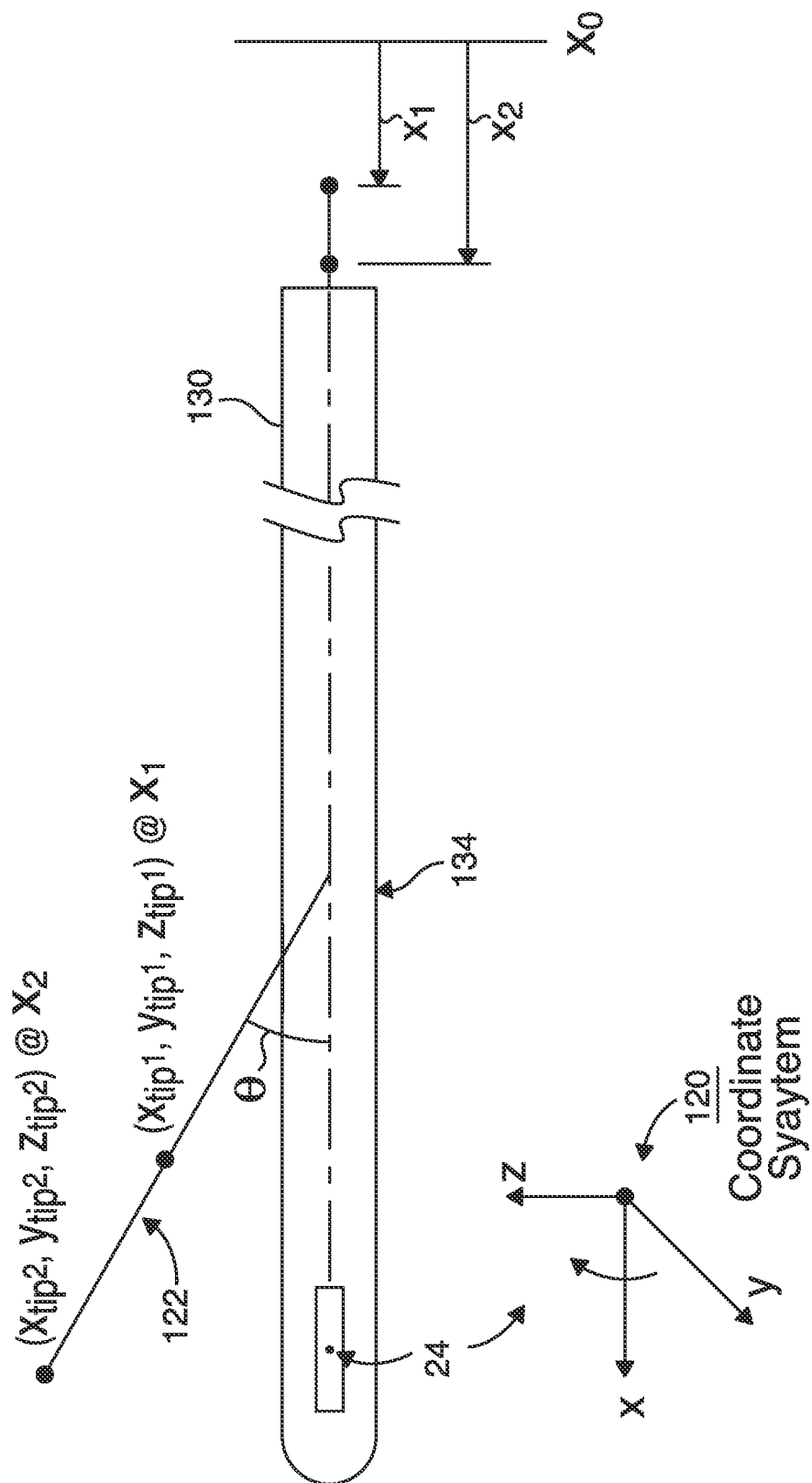
FIG. 36 is a side view illustrating the calibration of path of the medical instrument as it extends out the side exit of the surgical catheter according to an embodiment of the present invention.

In certain embodiments, as illustrated in FIG. 36, after calibration of the alignment of localization element 24 (e.g., an electromagnetic sensor) in side exiting catheter 100 using the calibration jig system, path 122 of a medical instrument (not shown) may be calibrated relative to the position of localization element 24. During calibration, the location/coordinates of the tip of medical instrument 108 will be measured relative to the position of localization element 24 for an initial position $X_0$. After medical instrument 108 is advanced in elongate flexible shaft 130 a distance $X_1$ to extend medical instrument 108 through side exit 105 to a position outside the elongate flexible shaft 130 the location/coordinates of the tip of medical instrument 108 can be measured at $x_{tip1}$, $y_{tip1}$, and $z_{tip1}$ relative to local coordinate system 120 of localization element 24. Similarly, after medical instrument 108 is advanced in elongate flexible shaft 130 a distance $X_2$ to extend medical instrument 108 to a further position outside the elongate flexible shaft 130 the location/coordinates of the tip of medical instrument 108 can be measured at $x_{tip2}$, $y_{tip2}$, $z_{tip2}$ relative to local coordinate system 120 of localization element 24. As medical instrument 108 extends through side exit 105 (see FIG. 35) the path 122 of medical instrument 108 is at angle Θ relative to longitudinal axis 109. As such, the location/coordinates of the tip of medical instrument 108 can be measured at a plurality of positions (e.g., 2, 3, 4, or more) within and outside elongate flexible shaft 130. The calibration can be along the range of distances for which medical instrument 108 may be advanced. Accordingly, after path 122 of medical instrument 108 is determined, the path 122 can be displayed by surgical instrument navigation system 10 (see FIG. 1) as a virtual path to aid the physician or other healthcare professional in extending the medical instrument to the desired region (or tissue) of interest.

Referring again to FIG. 35, in one embodiment, medical instrument 108 can be a flexible instrument, which in certain embodiments, may be an aspiration needle. In certain embodiments, the flexible instrument may be comprised of flexible nitinol. In another embodiment, medical instrument 108 can be constructed of a flexible coil having a stainless steel tip. In yet another embodiment, medical instrument 108 may be a relatively rigid (non-flexible). In yet other embodiments, medical instrument 108 may comprise a shape memory alloy, as described in greater detail elsewhere herein. As illustrated in FIG. 37, medical instrument 108 may comprise a variety of biopsy devices at the end 140 of medical instrument 108, including, but not limited to, for example, a forceps device 37A, an auger device 37D, a boring bit device 37B, and a brush device 37C. In addition to biopsy devices, in yet other embodiments, a variety of medical instruments may be used such as fiducial delivery devices, diagnostic imaging devices (such as OCT), or therapy devices (such as an ablation device, an RF emitter, a microwave emitter, a laser device, a device to deliver a radioactive seed, a cryogenic therapy delivery device, a drug delivery device, or a fluid delivery device, among others), or combinations thereof, and the like. In other embodiments, medical instrument 108 may be used to deliver therapy to a surgical site (e.g., fluids, drugs, radioactive seeds, combinations thereof, or the like).

Figure 38:
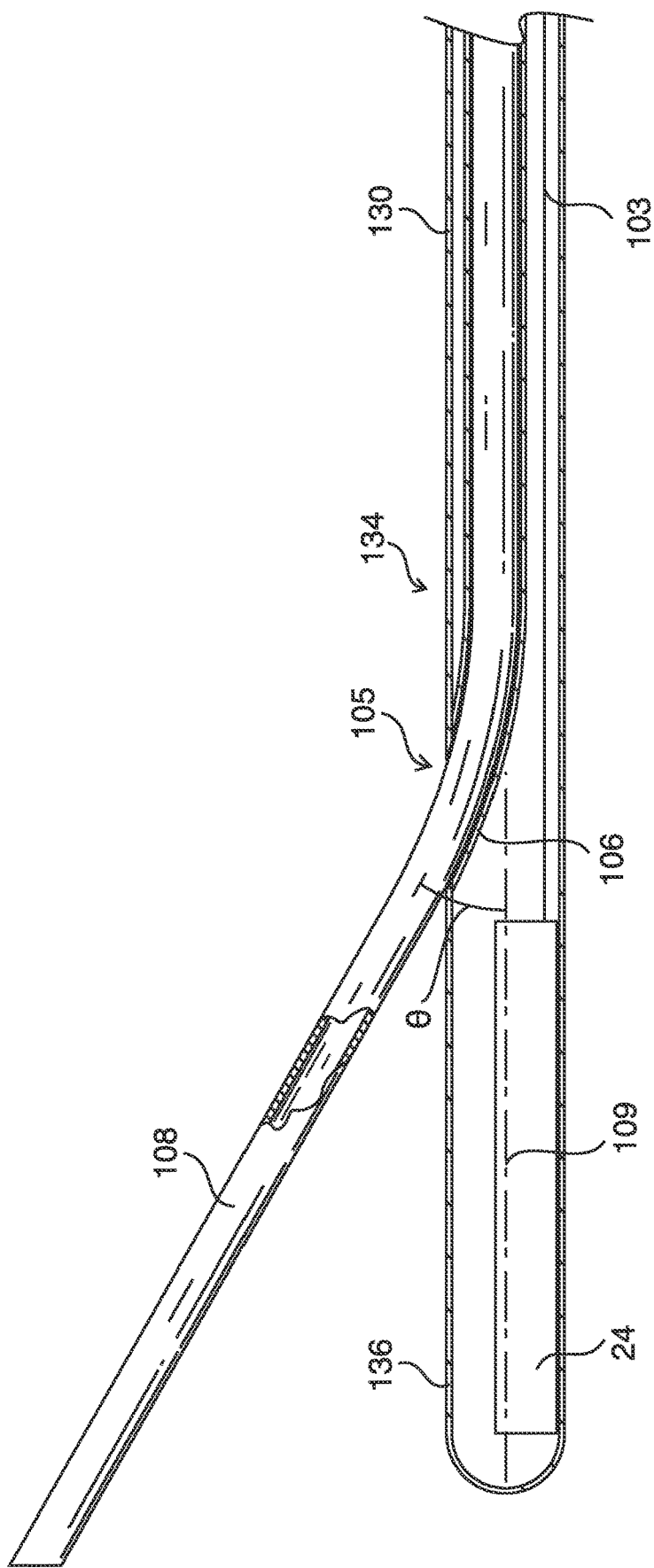
FIG. 38 is a side cutaway view of the surgical catheter with a medical instrument extended through the side exit, wherein the medical instrument is an aspiration needle, and a localization element is at the distal end portion of an elongate flexible shaft according to an embodiment of the present invention.

In one embodiment, as illustrated by FIG. 38, medical instrument 108 extends through side exit 105 along a path at an angle Θ of at least 10 degrees relative to longitudinal axis 109. Typically, medical instrument 108 extends through side exit 105 along a path at an angle from about 10 degrees to about 70 degrees relative to longitudinal axis 109. By way of example, in certain embodiments, medical instrument 108 extends through side exit 105 along a path at an angle of about 10 degrees relative to longitudinal axis 109. By way of further example, in certain embodiments, medical instrument 108 extends through side exit 105 along a path at an angle of about 15 degrees relative to longitudinal axis 109. By way of further example, in certain embodiments, medical instrument 108 extends through side exit 105 along a path at an angle of about 20 degrees relative to longitudinal axis 109. By way of further example, in certain embodiments, medical instrument 108 extends through side exit 105 along a path at an angle of about 25 degrees relative to longitudinal axis 109. By way of further example, in certain embodiments, medical instrument 108 extends through side exit 105 along a path at an angle of about 30 degrees relative to longitudinal axis 109. By way of further example, in certain embodiments, medical instrument 108 extends through side exit 105 along a path at an angle of about 35 degrees relative to longitudinal axis 109. By way of further example, in certain embodiments, medical instrument 108 extends through side exit 105 along a path at an angle of about 40 degrees relative to longitudinal axis 109. By way of further example, in certain embodiments, medical instrument 108 extends through side exit 105 along a path at an angle of about 45 degrees relative to longitudinal axis 109. By way of further example, in certain embodiments, medical instrument 108 extends through side exit 105 along a path at an angle of about 50 degrees relative to longitudinal axis 109. By way of further example, in certain embodiments, medical instrument 108 extends through side exit 105 along a path at an angle of about 55 degrees relative to longitudinal axis 109. By way of further example, in certain embodiments, medical instrument 108 extends through side exit 105 along a path at an angle of about 60 degrees relative to longitudinal axis 109. By way of further example, in certain embodiments, medical instrument 108 extends through side exit 105 along a path at an angle of about 65 degrees relative to longitudinal axis 109. By way of further example, in certain embodiments, medical instrument 108 extends through side exit 105 along a path at an angle of about 70 degrees relative to longitudinal axis 109.

Figure 39:
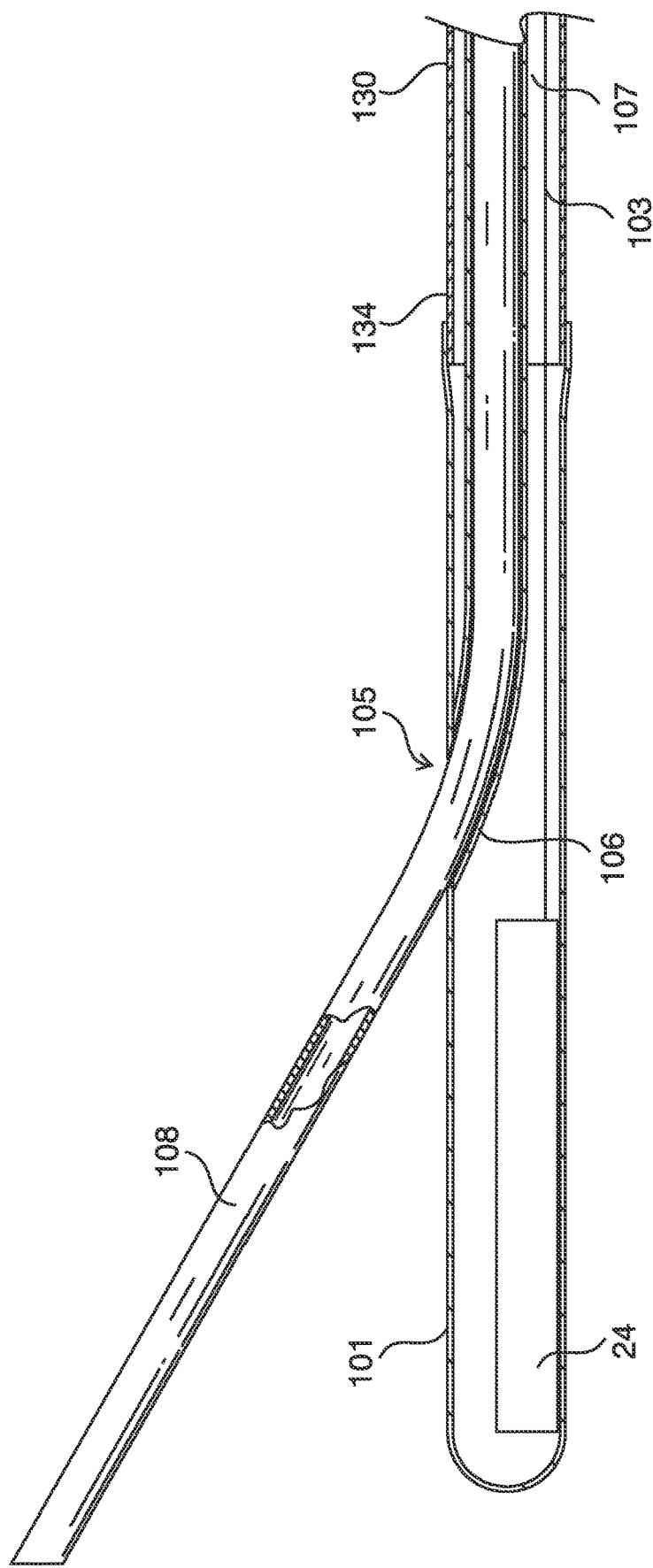
FIG. 39 is a side cutaway view of the surgical catheter with a medical instrument extended through the side exit and a localization element is at the tip of the side exiting tip component according to an embodiment of the present invention.

Referring now to FIG. 39, another embodiment of the side exiting catheter is shown wherein a side exiting tip component 101 is at distal end portion 134 of elongate flexible shaft 130. Side exiting tip component 101 has a proximal and a distal end and a side exit 105. In certain embodiments, localization element(s) 24 is positioned at or near the proximal end and/or near the distal end of side exiting tip component 101. In this embodiment, medical instrument 108 extends through channel 106 of side exiting tip component 101 and channel 107 of elongate flexible shaft 130. Additionally, a medical instrument 108 is shown extended through side exit 105 along a path at an angle.

Figure 40:
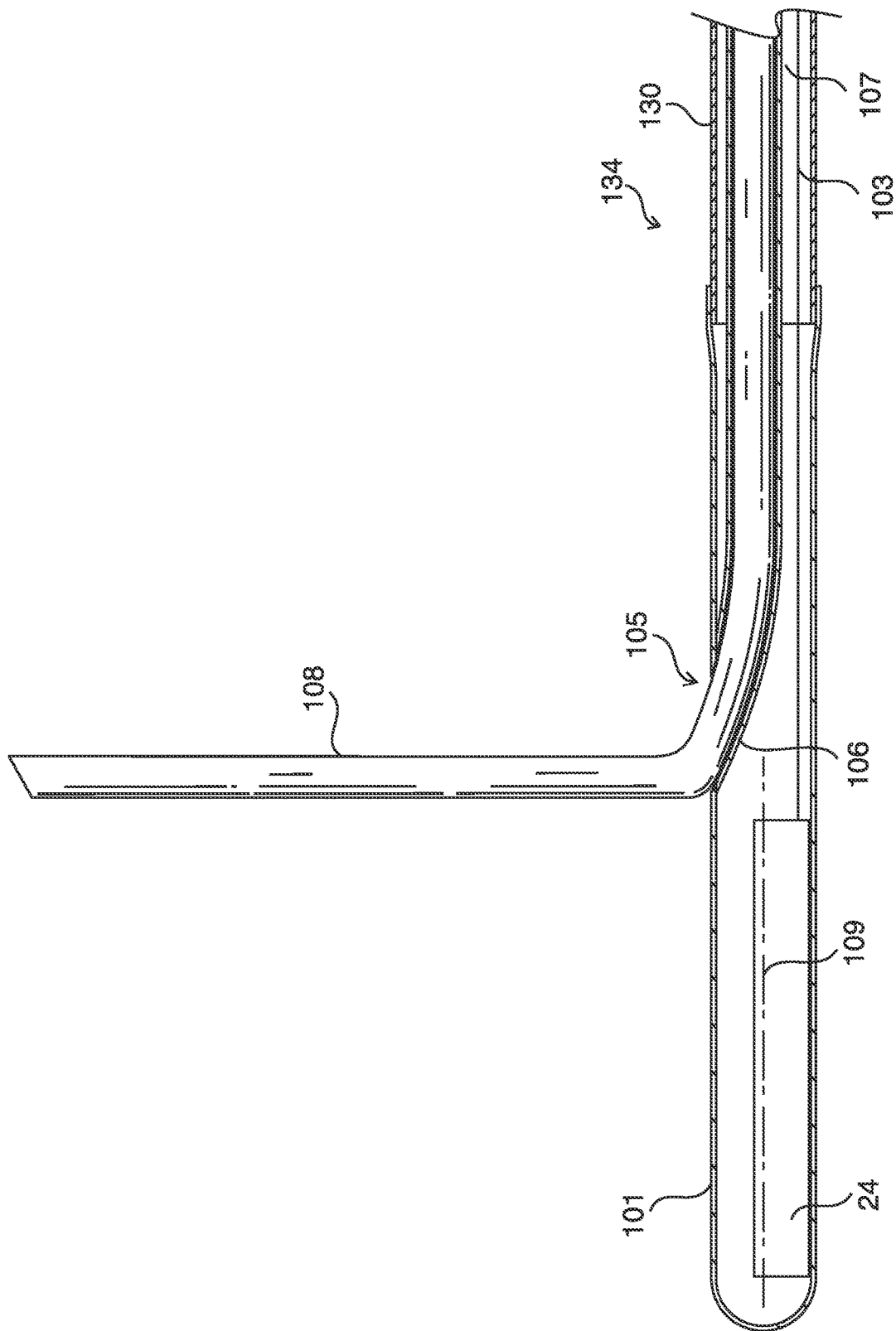
FIG. 40 is a side cutaway view of the surgical catheter wherein the medical instrument comprises a shape memory alloy extended out of the side exit according to an embodiment of the present invention.

In yet another embodiment, side exiting tip component 101 may comprise medical instrument 108 formed from a shape memory alloy which transitions between a first and second shape upon the application or release of stress. In certain embodiments, medical instrument 108 may be made of a superelastic material such as Nickel-Titanium (Ni—Ti) alloy (commercially available as nitinol) that has a martensitic to austenitic transformation temperature below body temperature and below normal room temperature. In other embodiments, other suitable shape memory materials for medical instrument 108 can include elastic biocompatible metals such as stainless steel, titanium, and tantalum or superelastic or psuedoelastic copper alloys, such as Cu—Al—Ni, Cu—Al—Zi, and Cu—Zi. When formed, medical instrument 108 comprising shape memory alloy will have a bend at a desired location with a bend angle (i.e., the first shape) and when housed within elongate flexible shaft 130, medical instrument 108 becomes relatively straight (i.e., the second shape). When medical instrument 108 is advanced and extends through side exit 105, the stress is removed and medical instrument 108 will return back to its preformed (first) shape. Accordingly, medical instrument 108 comprising shape memory alloy may be able to interact with regions (or tissues) of interest at additional angles than can be achieved the by a medical instrument 108 comprising a non-shape memory material extending through side exit 105. As illustrated in FIG. 40, the longitudinal axis of the portion of medical instrument 108 extending outside distal end portion 134 is at an angle of approximately 90 degrees relative to the longitudinal axis 109.

In yet another embodiment, medical instrument 108 comprising shape memory alloy may be used with a catheter having an exit at the distal end, wherein medical instrument 108 exits the catheter along a longitudinal axis. By using a medical instrument comprising a shape memory alloy with a catheter having an exit along a longitudinal axis, a physician or other healthcare provider is able to target lesions, or other targets, that may not be directly in the airway or other pathways, but rather partially or even completely outside of the airway or other pathways. Such targeting may not be possible with a catheter having an exit at the distal end and non-shape memory instruments. Similar to FIG. 37, medical instrument 108 comprising shape memory alloy may comprise a variety of biopsy devices, including, but not limited to, for example, a forceps device 37A, an auger device 37D, a boring bit device 37B, a brush device 37C, and an aspiration needle device. In addition to biopsy devices, in yet other embodiments, a variety of shape memory instruments may be used such as fiducial delivery devices, diagnostic imaging devices (such as OCT), therapy devices (such as an ablation device, an RF emitter, a microwave emitter, a laser device, a device to deliver a radioactive seed, a cryogenic therapy delivery device, a drug delivery device, or a fluid delivery device, among others), or combinations thereof, and the like.

As shown by FIGS. 41A, 41B, 41C and 41D, in various embodiments of medical instrument 108 used in steerable catheter 100, wherein medical instrument 108 is in the extended position it may be disposed at various angles relative to longitudinal axis 109 of elongate flexible shaft 130 at side exit 105. By way of example, in certain embodiments, wherein medical instrument 108 is in the extended position it may be disposed at least about 20 degrees relative to longitudinal axis 109 of elongate flexible shaft 130 at side exit 105. By way of further example, in certain embodiments, wherein medical instrument 108 is in the extended position it may be disposed at least about 30 degrees relative to longitudinal axis 109 of elongate flexible shaft 130 at side exit 105. By way of further example, in certain embodiments, wherein medical instrument 108 is in the extended position it may be disposed at least about 40 degrees relative to longitudinal axis 109 of elongate flexible shaft 130 at side exit 105. By way of further example, in certain embodiments, wherein medical instrument 108 is in the extended position it may be disposed at least about 50 degrees relative to longitudinal axis 109 of elongate flexible shaft 130 at side exit 105. By way of further example, in certain embodiments, wherein medical instrument 108 is in the extended position it may be disposed at least about 60 degrees relative to longitudinal axis 109 of elongate flexible shaft 130 at side exit 105. By way of further example, in certain embodiments wherein medical instrument 108 is in the extended position it may be disposed at least about 70 degrees relative to longitudinal axis 109 of elongate flexible shaft 130 at side exit 105. By way of further example, in certain embodiments, wherein medical instrument 108 is in the extended position it may be disposed at least about 80 degrees relative to longitudinal axis 109 of elongate flexible shaft 130 at side exit 105. By way of further example, in certain embodiments wherein medical instrument 108 is in the extended position it may be disposed at least about 90 degrees relative to longitudinal axis 109 of elongate flexible shaft 130 at side exit 105. By way of further example, in certain embodiments, wherein medical instrument 108 is in the extended position it may be disposed at least about 100 degrees relative to longitudinal axis 109 of elongate flexible shaft 130 at side exit 105. By way of further example, in certain embodiments wherein medical instrument 108 is in the extended position it may be disposed at least about 110 degrees relative to longitudinal axis 109 of elongate flexible shaft 130 at side exit 105. By way of further example, in certain embodiments, wherein medical instrument 108 is in the extended position it may be disposed at least about 120 degrees relative to longitudinal axis 109 of elongate flexible shaft 130 at side exit 105. By way of further example, in certain embodiments, wherein medical instrument 108 is in the extended position it may be disposed at least about 130 degrees relative to longitudinal axis 109 of elongate flexible shaft 130 at side exit 105. By way of further example, in certain embodiments, wherein medical instrument 108 is in the extended position it may be disposed at least about 140 degrees relative to longitudinal axis 109 of elongate flexible shaft 130 at side exit 105. By way of further example, in certain embodiments, wherein medical instrument 108 is in the extended position it may be disposed at least about 150 degrees relative to longitudinal axis 109 of elongate flexible shaft 130 at side exit 105. By way of further example, in certain embodiments, wherein medical instrument 108 is in the extended position it may be disposed at least about 160 degrees relative to longitudinal axis 109 of elongate flexible shaft 130 at side exit 105. By way of further example, in certain embodiments, wherein medical instrument 108 is in the extended position it may be disposed at least about 170 degrees relative to longitudinal axis 109 of elongate flexible shaft 130 at side exit 105. By way of further example, in certain embodiments, wherein medical instrument 108 is in the extended position it may be disposed at about 180 degrees relative to longitudinal axis 109 of elongate flexible shaft 130 at side exit 105.

Figure 17G:
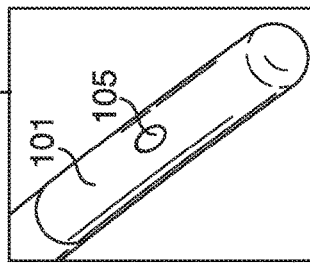
Figure 17F:
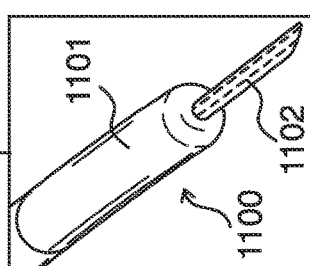
Figure 17E:
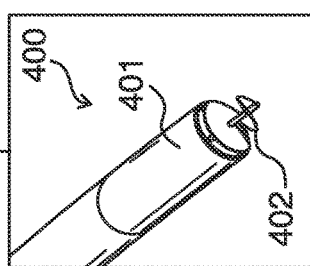

As shown in FIG. 17G, in an embodiment of the present invention, elongate flexible shaft 130 of side exiting catheter 100 can be steerable wherein elongate flexible shaft 130 comprises a steering mechanism comprising a steering actuator 218 at proximal end portion 132 and a pull wire connected to steering actuator 218 wherein distal end portion 134 may be moved relative to proximal end portion 132 by manipulating steering actuator 218 to apply a tension to the pull wire. Referring now to FIG. 41E, medical instrument 108 is shown in the extended position through side exit 105 of a steerable catheter comprising elongate flexible shaft 230. Medical instrument 108 extends through side exit 105 along a path at an angle Θ of at least 10 degrees relative to longitudinal axis 207. As described in greater detail elsewhere herein, in one embodiment, manipulation of steering actuator 218 (see FIGS. 18A and 18B) introduces an arc of β degrees into elongate flexible shaft 230. Distal end portion 234 may be moved to a distance that separates two regions of elongate flexible shaft 230 located at opposing ends of a chord X connecting to two points separated by β degrees on the arc.

Typically, the outer diameter of elongate flexible shaft 130 of side exiting catheter 100 is less than 5 mm. By way of example, in certain embodiments, the outer diameter elongate flexible shaft 130 of side exiting catheter 100 is less than 1 mm. By way of further example, in certain embodiments, the outer diameter of elongate flexible shaft 130 of side exiting catheter 100 is less than 2 mm. By way of further example, in certain embodiments, the outer diameter of elongate flexible shaft 130 of side exiting catheter 100 is less than 3 mm. By way of further example, in certain embodiments, the outer diameter of elongate flexible shaft 130 of side exiting catheter 100 is less than 4 mm. By way of further example, in certain embodiments, the outer diameter of elongate flexible shaft 130 of side exiting catheter 100 is less than 5 mm.

However, in other embodiments, in addition to, or in place of, localization element 24, side exiting catheter 100 may be navigated wherein elongate flexible shaft 130 or medical instrument 108 may further comprise radiopaque markers visible via fluoroscopic imaging, or echogenic materials or patterns that increase visibility of the tip component under an ultrasonic beam. In yet other embodiments, side exiting catheter 100 may be navigated via other types of sensors, such as conductive localization elements, fiber optic localization elements, or any other type of localization element.

Figure 42A:
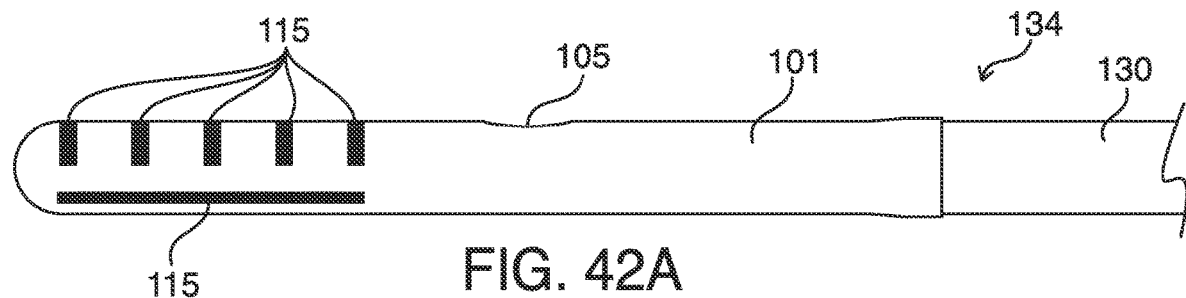
FIGS. 42A, 42B, and 42C are a side, top, and bottom view of the surgical catheter comprising an angled or directional pattern visible via fluoroscopic imaging according to an embodiment of the present invention.
Figure 42B:
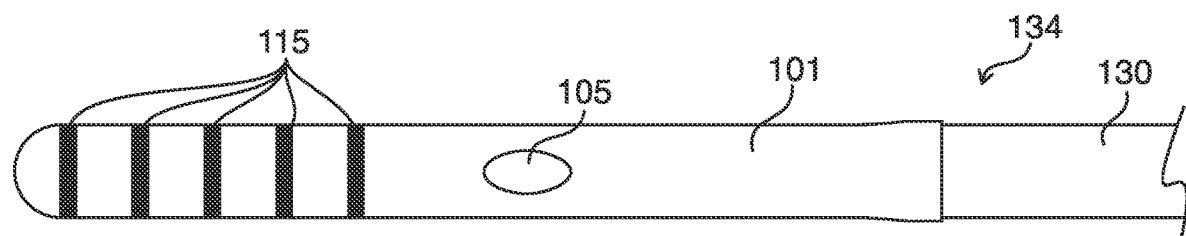
Figure 42C:
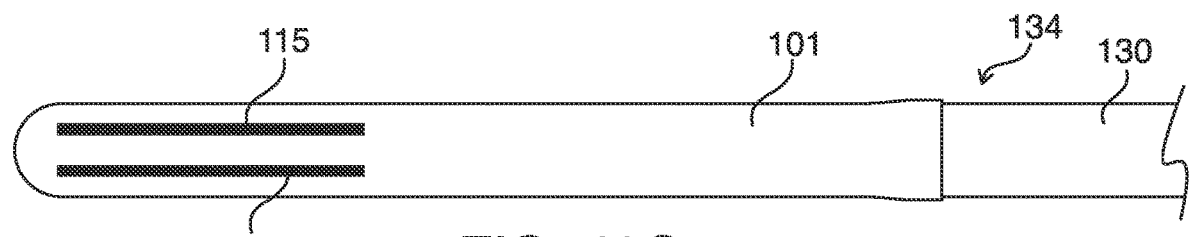

In one embodiment, side exiting tip component 101, illustrated by FIGS. 42A, 42B, and 42C, may be visible via fluoroscopic imaging. An angled or directionally arranged radiopaque marker pattern 115 at or near the proximal end and/or the distal end of side exiting tip component 101. The radiopaque marker pattern 115 may be made of stainless steel, tantalum, platinum, gold, barium, bismuth, tungsten, iridium, or rhenium, alloys thereof, or of other radiopaque materials known in the art. Radiopaque marker pattern 115 allows for tracking of the location and orientation of side exit 105. Based upon the orientation of radiopaque marker pattern 115 with respect to the incident fluoroscopic beam, a distinct image is visible on a fluoroscope. As side exiting catheter 100 is navigated and rotated into position at the region (or tissue) of interest, the orientation of radiopaque marker pattern 115 with respect to the incident fluoroscopic beam will be altered resulting in a corresponding change to the fluoroscopic image, thereby allowing the physician or other healthcare professional to know the location and orientation of side exit 105. Accordingly, the physician or other healthcare professional can then extend medical instrument 108 at the region (or tissue) of interest. Additionally, radiopaque marker pattern 115 may assist the physician or other healthcare professional in avoiding the passage of the elongate flexible shaft 130 and the medical instrument 108 into healthy tissue, a blood vessel, or other undesired patient area. In other embodiments, radiopaque marker pattern 115 may be on distal end portion 134 of elongate flexible shaft 130 of side exiting catheter 100. In one embodiment radiopaque marker pattern 115 may replace a six (6) degree of freedom (6DOF) electromagnetic sensor. In other embodiments, radiopaque marker pattern 115, may supplement a six (6) degree of freedom (6DOF) electromagnetic sensor.

Figure 43A:
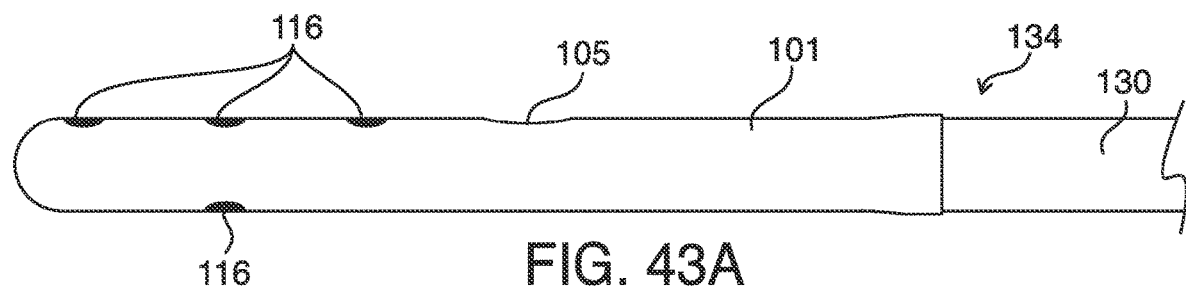
FIGS. 43A, 43B, and 43C are a side, top, and bottom view of the surgical catheter comprising markers visible via fluoroscopic imaging according to an embodiment of the present invention.
Figure 43B:
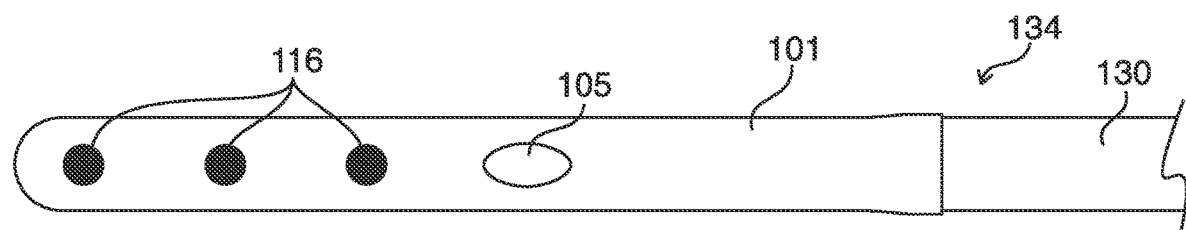
Figure 43C:

As illustrated in FIGS. 43A, 43B, and 43C, in another embodiment radiopaque marker pattern 115 comprises generally circular radiopaque markers 116 placed around side exiting tip component 101, with 3 radiopaque markers on one side of side exiting tip component 101 and 1 radiopaque marker on the opposite side of side exiting tip component 101. By way of example, in certain embodiments, 4 radiopaque markers are placed on one side of side exiting tip component 101 and 2 radiopaque markers are placed on the opposite side of side exiting tip component 101. By way of further example, in certain embodiments, 5 radiopaque markers are placed on one side of side exiting tip component 101 and 3 radiopaque markers are placed on the opposite side of side exiting tip component 101. In other embodiments, radiopaque marker pattern 115 may be on distal end portion 134 of elongate flexible shaft 130 of side exiting catheter 100.

Figure 44A:
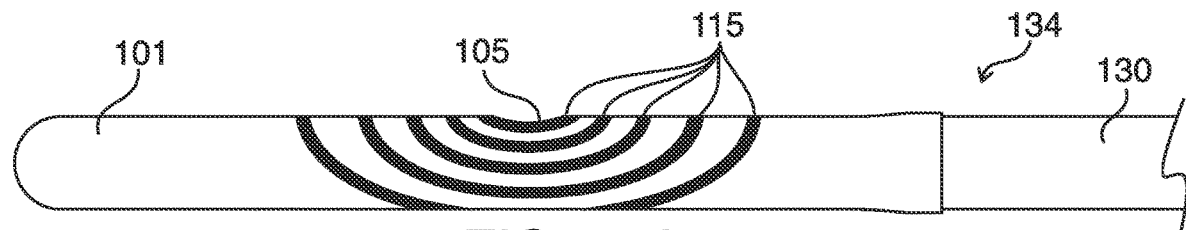
FIGS. 44A, 44B, and 44C are a side, top, and bottom view of the surgical catheter comprising rings visible via fluoroscopic imaging according to an embodiment of the present invention.
Figure 44B:
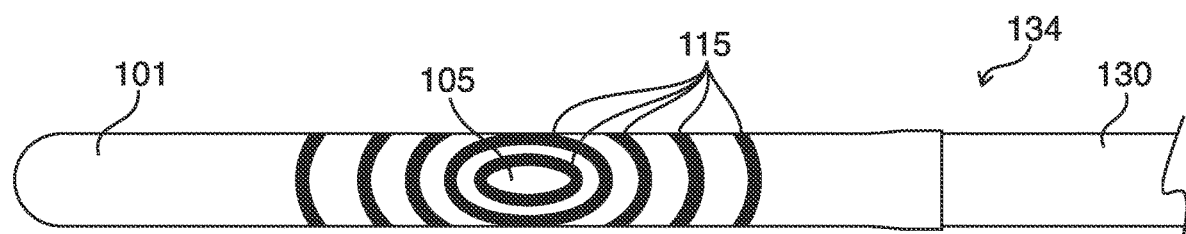
Figure 44C:

In yet another embodiment, at least one ring of radiopaque material 115 may surround side exit 105. By way of example, in one embodiment illustrated in FIGS. 44A, 44B, and 44C, side exit 105 of side exiting tip component 101 is surrounded by a first ring of radiopaque material 115 that is concentric to and in immediate connection with side exit 105 of the side exiting tip component 101. This first ring of radiopaque material 115 is further surrounded by additional separate rings that are concentric to side exit 105 and the first ring of radiopaque material 115. By way of example, in certain embodiments, side exit 105 is surrounded by 1 ring of radiopaque material 115. By way of further example, in certain embodiments, side exit 105 is surrounded by 2 rings of radiopaque material 115. By way of further example, in certain embodiments, side exit 105 is surrounded by 3 rings of radiopaque material 115. By way of further example, in certain embodiments, side exit 105 is surrounded by 4 rings of radiopaque material 115. By way of further example, in certain embodiments, side exit 105 is surrounded by 5 rings of radiopaque material 115. By way of further example, in certain embodiments, side exit 105 is surrounded by 6 rings of radiopaque material 115. In other embodiments, radiopaque marker pattern 115 may be on distal end portion 134 of elongate flexible shaft 130.

In certain embodiments, all or a portion of side exiting tip component 101 and/or distal end portion 134 of elongate flexible shaft 130 of side exiting catheter 100 may be echogenic such that it may be viewed via ultrasonic imaging. Several approaches of enhancing the ultrasonic signature of medical devices through modification of the device surface reflectivity are known in the prior art and can be applied to certain embodiments of the present invention. In one embodiment, an echogenic pattern can be positioned around the side exiting tip component 101 and/or around distal end portion 134 of elongate flexible shaft 130, such that the echogenic pattern covers the exterior circumference of side exiting tip component 101 and/or distal end portion 134 of elongate flexible shaft 130. Typically an echogenic pattern is on the exterior surface of side exiting tip component 101 defined as a length from the distal end of side exiting tip component 101 toward the proximal end of side exiting tip component 101. By way of example, in one embodiment, the echogenic pattern has a length of about 1 cm from the distal end of side exiting tip component 101. By way of further example, in another embodiment, the echogenic pattern has a length of about 2 cm from distal end of the side exiting tip component 101.

In one embodiment, as illustrated by FIG. 45 and FIG. 45A, the echogenic pattern comprises a plurality of grooves 113 are cut into the exterior surface of side exiting tip component 101 such that the grooves increase the reflective coefficient of side exiting tip component 101. The plurality of grooves 113 cause constructive interference of the ultrasonic beam to affect an amplification of the reflecting beam along the line of the incident beam. In other embodiments, plurality of grooves 113 may be in distal end portion 134 of elongate flexible shaft 130 of side exiting catheter 100.

By way of further example, another embodiment of side exiting tip component 101 with an echogenic pattern is shown in FIG. 46 and FIG. 46A. In this embodiment, the echogenic pattern comprises a plurality of partially spherical indentations 114 on the exterior surface of side exiting tip component 101, such that the radius of the partially spherical indentations is less than the wavelength of the incident ultrasonic beam. The plurality of partially spherical indentations 114 cause constructive interference of the ultrasonic beam to affect an amplification of the reflecting beam along the line of the incident beam; such amplification occurs at any incident ultrasonic beam angle. In other embodiments, plurality of partially spherical indentations 114 may be in distal end portion 134 of elongate flexible shaft 130 of side exiting catheter 100.

Figure 47:
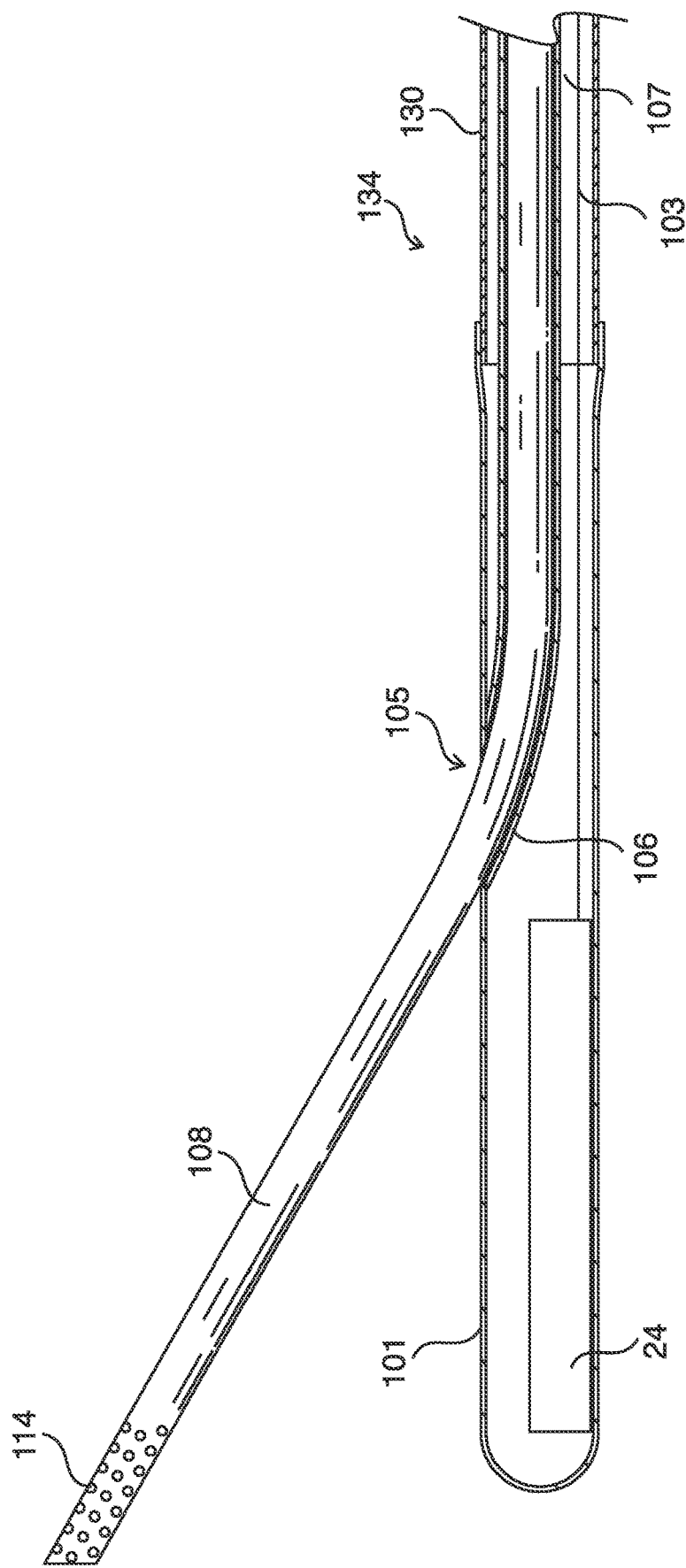
FIG. 47 is a side cutaway view of the surgical catheter comprising an echogenic pattern visible via ultrasonic imaging that is on the medical instrument according to an embodiment of the present invention.

In certain embodiments, as shown in FIG. 47, all or a portion of medical instrument 108 may be echogenic such that it may be viewed via ultrasonic imaging. Several approaches of enhancing the ultrasonic signature of medical devices through modification of the device surface reflectivity are known in the prior art and can be applied to certain embodiments of the present invention.

Figure 48:
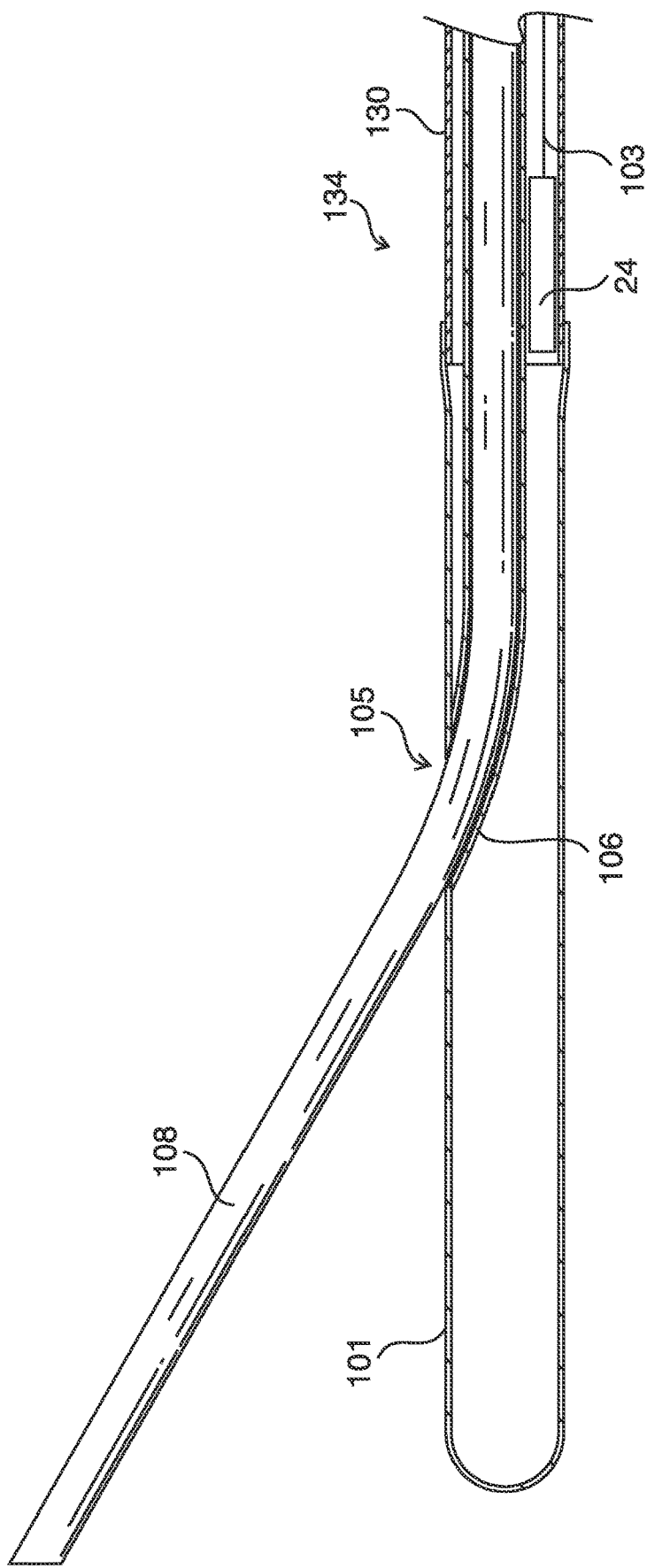
FIG. 48 is a side cutaway view of the surgical catheter with a medical instrument extended through the side exit and a localization element in the distal end portion of the elongate flexible shaft according to an embodiment of the present invention.

In certain embodiments, as discussed herein, localization element 24 is positioned at or near distal end portion 134 of elongate flexible shaft 130. In one embodiment, as shown in FIG. 48, localization element 24 comprises a six (6) degree of freedom (6DOF) electromagnetic sensor in the distal end portion 134 of the elongate flexible shaft 130. A localization element lead 103 extends from localization element 24 to proximal end portion 132 (not shown) of elongate flexible shaft 130. By way of further example, in another embodiment, an angled or directional pattern may be on the outside of elongate flexible shaft 130 that is visible via fluoroscopic imaging. Accordingly, embodiments of the present invention are not limited to one type and position of localization elements 24. In certain embodiments, a combination of different localization element 24 types or a series of the same localization element 24 types may positioned at or near distal end portion 134 of elongate flexible shaft 130 of side exiting catheter 100.

Figure 49A:
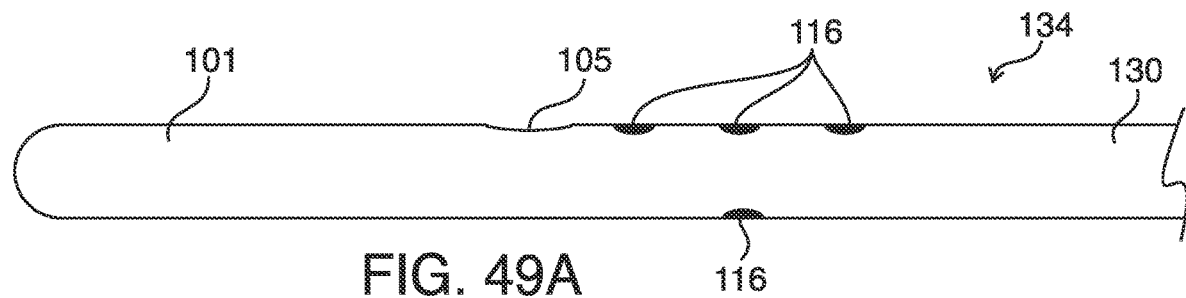
FIGS. 49A, 49B, and 49C show a side, top, and bottom view of the surgical catheter comprising an angled or directional pattern visible via fluoroscopic imaging according to an embodiment of the present invention.
Figure 49B:
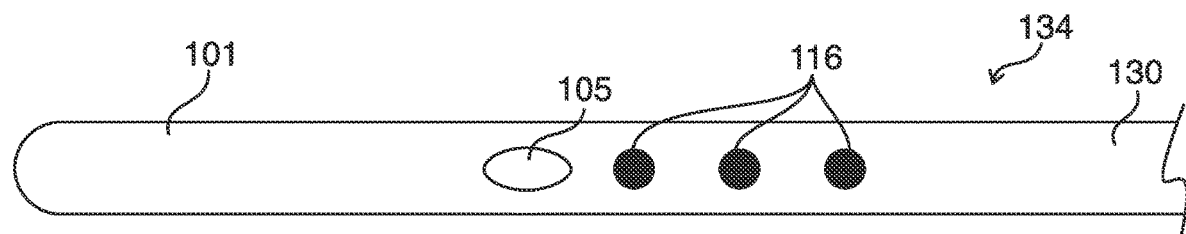
Figure 49C:

Another embodiment, with a radiopaque marker pattern positioned at or near the distal portion 134 of the elongate flexible shaft 130 is illustrated by FIGS. 49A, 49B, and 49C. In this embodiment a radiopaque marker pattern 115 comprising generally circular radiopaque markers 116 may be placed around distal end portion 134 of elongate flexible shaft 130, with 3 markers on one side of the distal end portion 134 of elongate flexible shaft 130 and 1 marker on the opposite side of distal end portion 134 of elongate flexible shaft 130. By way of example, in certain embodiments, 4 markers are placed on one side of distal end portion 134 of elongate flexible shaft 130 and 2 markers are placed on the opposite side of distal end portion 134 of elongate flexible shaft 130. By way of example, in certain embodiments, 5 markers are placed on one side of distal end portion 134 of elongate flexible shaft 130 and 3 markers are placed on the opposite side of distal end portion 134 of elongate flexible shaft 130 of side exiting catheter 100.

A method or procedure of guiding the side exiting catheter 100 of certain embodiments to a desired target tissue in the respiratory system of a patient may comprise displaying an image of the region of the patient, inserting a flexible lumen into the patient, and inserting into the flexible lumen side exiting catheter 100. Side exiting catheter 100 typically comprises an electromagnetic localization element at distal end portion 134. Side exiting catheter may then be navigated to the region of interest and the location and orientation of the electromagnetic localization element is detected. Then medical instrument 108 may be displayed, in real-time, on the image by superimposing a virtual representation of side exiting catheter 100 and medical instrument 108 on the image based upon the location and orientation of localization element 24. Then a medical procedure may be performed at the region (or tissue) of interest. In certain embodiments, side exiting catheter 100 further comprises an elongate flexible shaft 130 having a proximal end portion 132, an opposite distal end portion 134, a longitudinal axis 109, and an outer wall 136 comprising a biocompatible material extending from proximal end portion 132 to distal end portion 134. Side exiting catheter 100 may also comprise a handle 110 attached to proximal end portion 132, and a medical instrument 108 housed within distal end portion 134 of elongate flexible shaft 130 that is extendable along a path from a position within outer wall 136 through side exit 105 to a position outside outer wall 136 at an angle of at least 30 degrees relative to the longitudinal axis 109.

Figure 50A:
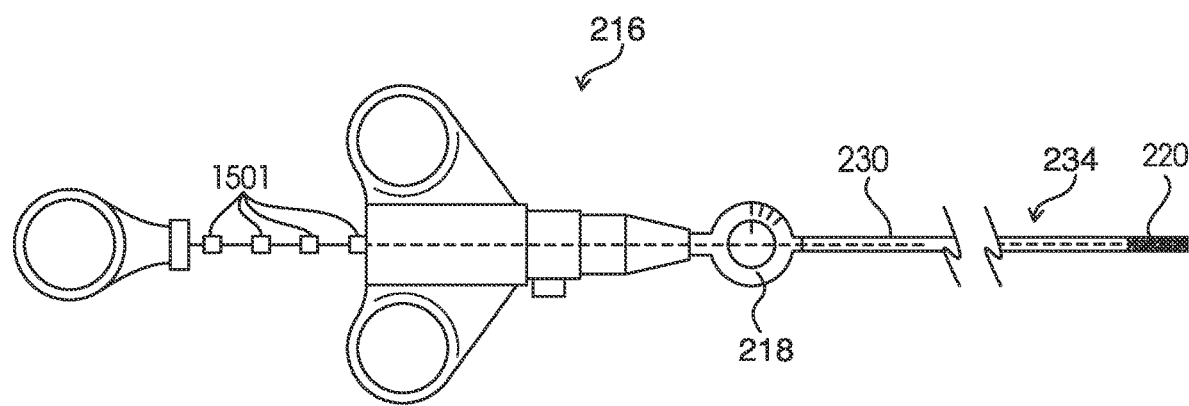
FIGS. 50A and 50B are side views of a port offset device according to an embodiment of the present invention.
Figure 50B:
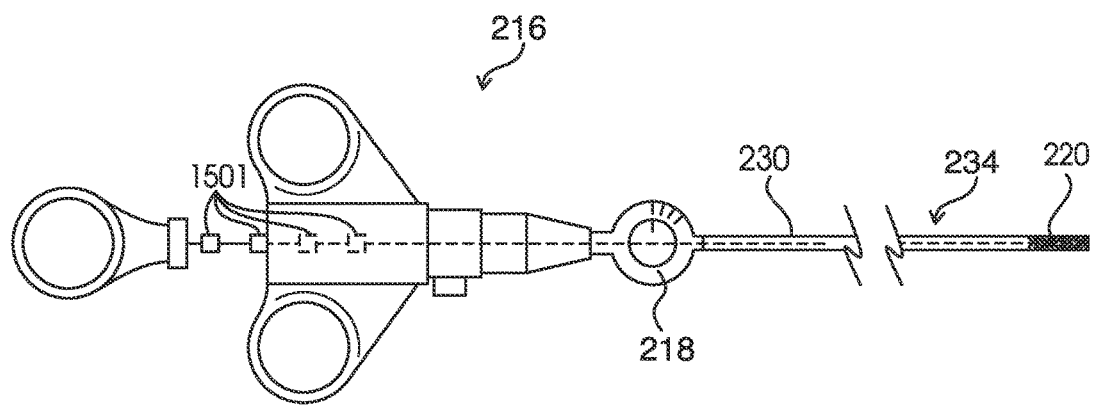

As illustrated in FIGS. 50A and 50B, another embodiment of the present invention includes an offset device to control the extension of a biopsy device or medical instrument. The offset device may comprise, for example, features (e.g., offsets) that snap-on or may be otherwise affixed to handle 216 that are capable of holding a biopsy device 220 in a known or preset (i.e., predetermined) location to maintain the biopsy device 220 extension and free the hands of the physician or other healthcare professional. In one embodiment, for example, the offset device includes one or more offset portions that can be adjusted by combining and/or removing multiple offset segments. In another embodiment, for example, the offset device includes one or more offset portions that can be adjusted by the removal of one or more removable offset segments separated by perforations (i.e., in a disposable fashion). In yet another embodiment, the offset device includes an offset that is capable of adjustment using a screw mechanism (i.e., the length of the offset can be adjusted by screwing the offset in and out). In various embodiments, each offset can be represented on the navigation screen showing offset distance from the distal end portion of the elongate flexible shaft. This representation is accomplished via sensors on the offset devices that would register the selected offset position. In additional embodiments, sensors (e.g., electromagnetic sensors, proximity sensors, limit switch sensors) at the handle may register the presence or contact with an offset device such that the extension depth of the biopsy device can be measured and represented on the navigation screen. The surgical catheter, in various embodiments, may include one or more offsets, two or more offsets, three or more offsets, four or more offsets, or five or more offsets. In other embodiments, more than five offsets may be included (e.g., 6-12 offsets, 6-18 offsets, 6-24 offsets, or more). An embodiment of offset device wherein the biopsy device is a brush is shown in FIGS. 50A and 50B. Another embodiment of the offset device wherein the medical instrument is a side exiting tip component is shown in FIGS. 51A and 51B.

As illustrated in FIGS. 50A and 50B, handle 216 attached to elongate flexible shaft 230 of steerable catheter 200 may include one or more offset devices 1501. The offset device(s) 1501 may be capable of holding the biopsy device 220, depicted as a brush, in place and provide a substantially fixed distance or length of extension out of elongate flexible shaft 230 to take a biopsy. As shown, multiple offsets 1501 can be provided in stages that allow extension of biopsy device 220 (e.g., at 1 cm, 2 cm, 3 cm, and so on) whereby the physician or other healthcare professional can adjust the offsets by removal or repositioning (removed offsets 1501R, for example, are depicted in dashed lines within the port in FIG. 50B). Thus, FIG. 50A shows biopsy device 220 prior to extension, whereas FIG. 50B shows biopsy device extended (e.g., 2 cm of extension) by the removal or repositioning of two offsets 1501R.

Figure 51A:
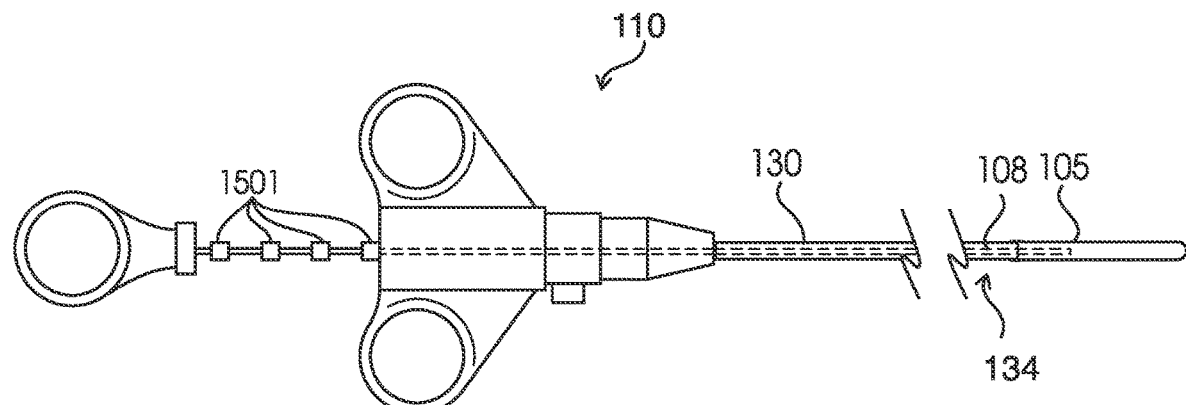
FIGS. 51A and 51B are side views of a port offset device according to an embodiment of the present invention.
Figure 51B:
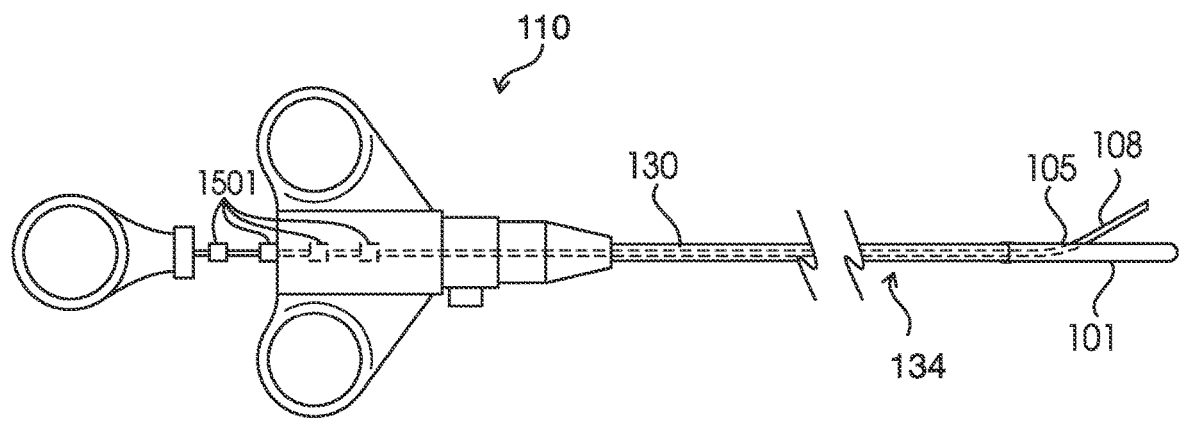

As shown in FIGS. 51A and 51B, another embodiment of the present invention is directed to an offset device for use with a medical instrument 108 that exits the side of elongate flexible shaft 130 of side exiting catheter 100. Handle 110 attached to elongate flexible shaft 130 may include one or more offset devices 1501. The offset device(s) 1501 may be capable of holding the medical instrument 108, depicted as an aspiration needle, in place and provide a substantially fixed distance or length of extension out of elongate flexible shaft 130 to take a biopsy. As shown, multiple offsets 1501 can be provided in stages that allow extension of medical instrument 108 (e.g., at 1 cm, 2 cm, 3 cm, and so on) out the side exit 105 of the elongate flexible shaft 130 whereby the physician or other healthcare professional can adjust the offsets by removal or repositioning (removed offsets 1501R, for example, are depicted in dashed lines within the port in FIG. 51B). Thus, FIG. 51A shows medical instrument 108 prior to extension, whereas FIG. 51B shows medical instrument 108 extended (e.g., 2 cm of extension) out side exit 105 of the elongate flexible shaft 130 by the removal or repositioning of two offsets 1501R.

Typically, biopsy device 220 may be extended a distance (extended distance) correlated to movement of handle 216 wherein extended distance may be from about 0.5 cm to about 4.0 cm. By way of example, in certain embodiments, the extended distance is at least about 0.5 cm. By way of further example, in certain embodiments, the extended distance is at least about 1.0 cm. By way of further example, in certain embodiments, the extended distance is at least about 1.5 cm. By way of further example, in certain embodiments, the extended distance is at least about 2.0 cm. By way of further example, in certain embodiments, the extended distance is at least about 2.5 cm. By way of further example, in certain embodiments, the extended distance is at least about 3.0 cm. By way of further example, in certain embodiments, the extended distance is at least about 3.5 cm. By way of further example, in certain embodiments, the extended distance is about 4.0 cm.

Typically, medical instrument 108 may be advanced a distance (advanced distance) correlated to movement of handle 110 wherein advanced distance may be from about 0.5 cm to about 4.0 cm. By way of example, in certain embodiments, the advanced distance is at least about 0.5 cm. By way of further example, in certain embodiments, the advanced distance is at least about 1.0 cm. By way of further example, in certain embodiments, the advanced distance is at least about 1.5 cm. By way of further example, in certain embodiments, the advanced distance is at least about 2.0 cm. By way of further example, in certain embodiments, the advanced distance is at least about 2.5 cm. By way of further example, in certain embodiments, the advanced distance is at least about 3.0 cm. By way of further example, in certain embodiments, the advanced distance is at least about 3.5 cm. By way of further example, in certain embodiments, the advanced distance is about 4.0 cm.

Figure 52A:
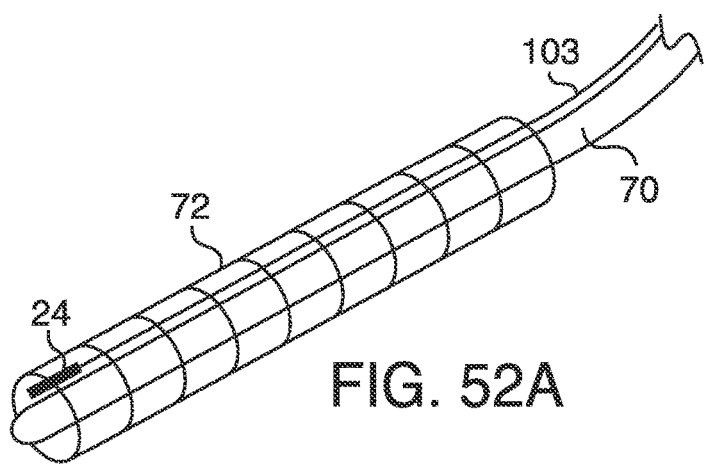
FIGS. 52A, 52B, 52C, and 52D are perspective views of affixing localization elements to existing surgical instruments according to an embodiment of the present invention.
Figure 52B:
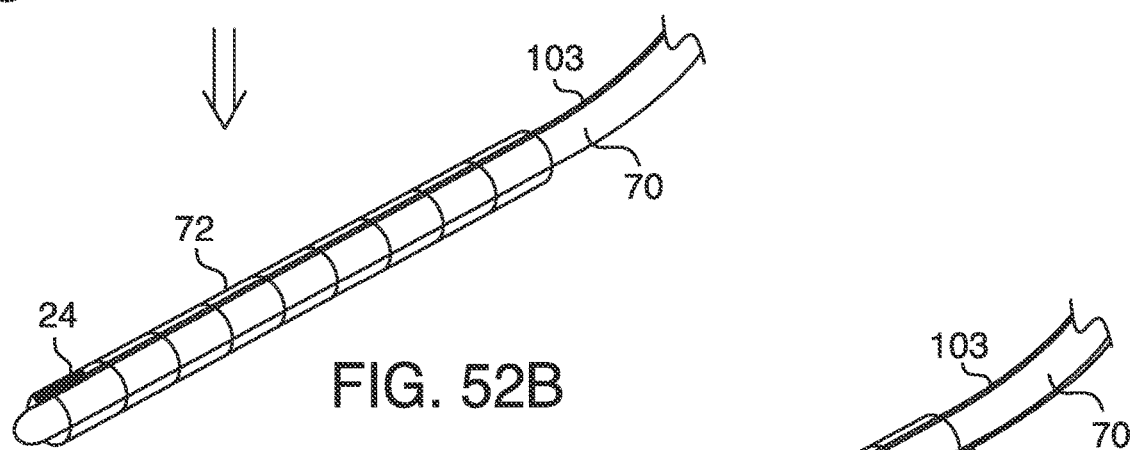
Figure 52C:
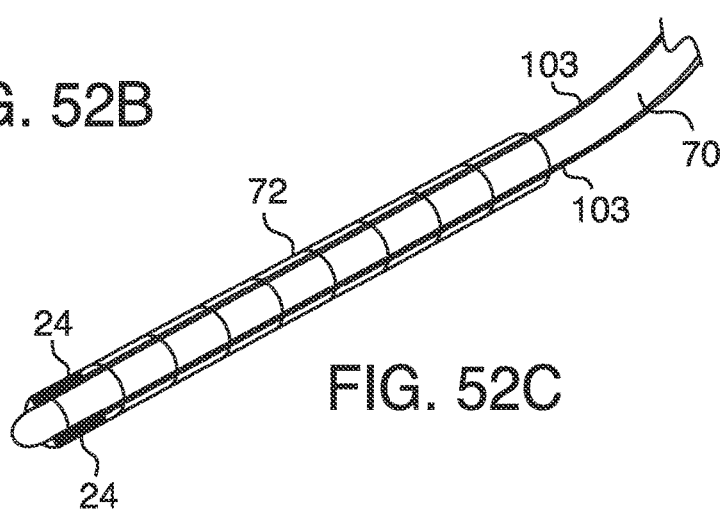
Figure 52D:
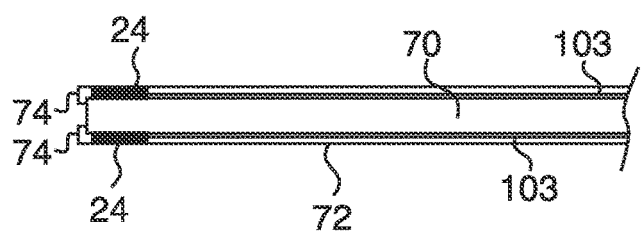

In another embodiment, as shown in FIGS. 52A, 52B, 52C, and 52D, a localization element 24 (e.g., electromagnetic sensor) can be attached to an existing, non-navigated surgical instrument or device 70 (e.g., steerable catheter, non-steerable catheter, bronchoscope, forceps device, auger device, boring bit device, aspiration needle device, brush device, side exiting tip component, etc.) for use in the systems and methods described herein. In one embodiment, as illustrated in FIG. 52A, a plastic or polymer sheath or condom 72 is placed over a localization element lead wire 103 and localization element 24. Then, as illustrated in FIG. 52B, the sheath or condom 72 may then be shrink-fitted to surgical instrument or device 70 via the application of a temperature differential. Typically the application of a heat treatment causes sheath or condom 72 to shrink to surgical instrument or device 70 and localization element lead wire/ localization element combination, thus converting existing, non-navigated surgical instrument or device 70 to a navigated surgical instrument or device 70. While heat treating is a common way to apply a temperature differential, it is understood that the existing, non-navigated surgical instrument or device 70 can be cooled before the plastic or polymer sheath or condom 72 is placed over existing, non-navigated surgical instrument or device 70. In another embodiment, as shown in FIG. 52C more than one localization element 24 may be attached to an existing, non-navigated surgical instrument or device 70 using a stretchable plastic or polymer sheath or condom 72. As illustrated in FIG. 52D, the stretchable plastic or polymer sheath or condom 72 may extend past the end of surgical instrument or device 70 such that a lip 74 is created when the sheath or condom 72 is affixed to non-navigated surgical instrument or device 70. This lip 74 may assist in registration of surgical instrument or device 70. In other embodiments, localization element 24 may be wireless, such that a localization element lead wire 103 is not required.

Other embodiments include, for example, a plastic or polymer sheath or condom that is custom sized to fit over an existing, non-navigated surgical instrument or device 70 and may be placed over a localization element lead wire 103 and localization element 24 to add a localization element 24 (e.g., an electromagnetic sensor), thus converting existing, non-navigated surgical instrument or device 70 to a navigated surgical instrument or device 70. In this embodiment, the plastic or polymer sheath or condom may be held in place on the existing, non-navigated surgical instrument or device 70 by a friction fit. In yet other embodiments, an elastic or stretchable plastic or polymer sheath or condom may be expanded and placed over a localization element lead wire 103 and localization element 24 to add a localization element 24 (e.g., an electromagnetic sensor), thus converting the existing, non-navigated surgical instrument or device 70 to a navigated surgical instrument or device 70. In this embodiment, the elastic or stretchable plastic or polymer sheath or condom may also be held in place on the existing, non-navigated surgical instrument or device 70 by a friction fit.

In yet other embodiments, a localization element 24 may be affixed to an existing, non-navigated surgical instrument or device 70 with tape. In certain embodiments, localization element 24 may be wireless. In other embodiments, localization element 24 may be affixed to an existing, non-navigated surgical instrument or device 70 via an adhesive.

In addition to or in place of localization element 24, steerable catheter 200 and/or side exiting catheter 100 may be equipped with one or more sensing devices at or near the distal end portion of the elongate flexible shaft and/or at the biopsy device 220 or medical instrument 108 of the respective catheters described herein. Additional sensing devices may include electrodes for sensing depolarization signals occurring in excitable tissue such as the heart, nerve or brain. In one embodiment, for use in cardiac applications, the sensing device may include at least one electrode for sensing internal cardiac electrogram (EGM) signals. In other embodiments, the sensing device may be an absolute pressure sensor to monitor blood pressure. In still other embodiments, surgical instrument 12 may be equipped with other sensing devices including physiological detection devices, localization elements, temperature sensors, motion sensors, optical coherence tomography (OCT) sensors, endobronchial ultrasound (EBUS) sensors, or Doppler or ultrasound sensors that can detect the presence or absence of blood vessels.

The accompanying Figures and this description depict and describe certain embodiments of a navigation system (and related methods and devices) in accordance with the present invention, and features and components thereof. It should also be noted that any references herein to front and back, right and left, top and bottom and upper and lower are intended for convenience of description, not to limit the present invention or its components to any one positional or spatial orientation.

It is noted that the terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. Thus, a method, an apparatus, or a system that "comprises," "has," "contains," or "includes" one or more items possesses at least those one or more items, but is not limited to possessing only those one or more items Individual elements or steps of the present methods, apparatuses, and systems are to be treated in the same manner. Thus, a step that calls for modifying a segmented image dataset for a region of a respiratory system to match the corresponding anatomy of a patient's respiratory system, that includes the steps of: (i) forming a respiratory-gated point cloud of data that demarcates anatomical features in a region of a patient's respiratory system at one or more discrete phases within a respiration cycle of a patient, (ii) density filtering the respiratory-gated point cloud, (iii) classifying the density filtered respiratory-gated point cloud according to anatomical points of reference in a segmented image dataset for the region of the patient's respiratory system, and (iv) modifying the segmented image dataset to correspond to the classified anatomical points of reference in the density filtered respiratory-gated point cloud, but also covers the steps of (i) comparing the registered respiratory-gated point cloud to a segmented image dataset to determine the weighting of points comprised by the classified respiratory-gated point cloud, (ii) distinguishing regions of greater weighting from regions of lesser weighting, and (iii) modifying the segmented image dataset to correspond to the classified respiratory-gated point cloud.

The terms "a" and "an" are defined as one or more than one. The term "another" is defined as at least a second or more. The term "coupled" encompasses both direct and indirect connections, and is not limited to mechanical connections.

Those of skill in the art will appreciate that in the detailed description above, certain well known components and assembly techniques have been omitted so that the present methods, apparatuses, and systems are not obscured in unnecessary detail.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the elongate flexible shafts, biopsy device, medical instruments, and localization elements can be constructed from any suitable material, and can be a variety of different shapes and sizes, not necessarily specifically illustrated, while still remaining within the scope of the invention.

What is claimed is:

1. A method of modifying a segmented image dataset for a region of a respiratory system to match the corresponding anatomy of a patient's respiratory system, the method comprising:
   (i) forming a respiratory-gated point cloud of data by moving a catheter having a fiber optic localization element through a plurality of locations in the patient's respiratory system, wherein the respiratory-gated point cloud of data demarcates anatomical features in a region of a patient's respiratory system at one or more discrete phases within a respiration cycle of the patient,
   (ii) density filtering the respiratory-gated point cloud,
   (iii) classifying the density filtered respiratory-gated point cloud according to anatomical points of reference in a segmented image dataset for the region of the patient's respiratory system,
   (iv) continuously modifying the segmented image dataset to correspond to the classified anatomical points of reference in the density filtered respiratory-gated point cloud to produce simulated real-time, intra-procedural images illustrating the orientation and shape of the anatomical features in the region of a patient's respiratory system, and (vii) detecting center locations of selected imaged anatomical features by applying a centroid finding algorithm to selected points of the density filtered respiratory-gated point cloud.

2. The method of claim 1 wherein the discrete phases are expiration, inspiration and discrete phases there-between.

3. The method of claim 1 wherein the segmented image dataset is from a first discrete phase of the patient's respiration cycle and the respiratory-gated point cloud is from a second and different discrete phase of the patient's respiration cycle.

4. The method of claim 1 wherein the segmented image dataset is a skeletonized segmented image dataset.

5. A method of simulating the movement of a patient's respiratory system in the patient's respiration cycle during respiration comprising:
(i) forming a respiratory-gated point cloud of data by moving a catheter having a fiber optic localization element through a plurality of locations in the patient's respiratory system, wherein the respiratory-gated point cloud of data demarcates anatomical features in a region of a patient's respiratory system at one or more discrete phases within a respiration cycle of a patient,
(ii) density filtering the respiratory-gated point cloud,
(iii) classifying the density filtered respiratory-gated point cloud according to anatomical points of reference in a segmented image dataset for the region of the patient's respiratory system,
(iv) creating a cine loop comprising a plurality of modified segmented image datasets through multiple modifications of the segmented image dataset to correspond to a plurality of classified anatomical points of reference in the respiratory-gated point cloud over the respiration cycle,
(v) displaying the cine loop comprising the plurality of modified segmented image datasets over the patient's respiration cycle, and
(vi) detecting center locations of selected imaged anatomical features by applying a centroid finding algorithm to selected points of the density filtered respiratory-gated point cloud.

6. The method of simulation of claim 5 wherein displaying the cine loop comprising the plurality of modified segmented image datasets over the patient's respiration cycle is synchronized with the patient's respiration cycle.

7. A method of preparing a segmented image dataset to match the anatomy of a patient's respiratory system, the method comprising:
(i) forming a respiratory-gated point cloud of data by moving a catheter having a fiber optic localization element through a plurality of locations in the patient's respiratory system, wherein the respiratory-gated point cloud of data demarcates anatomical features in a region of a patient's respiratory system at one or more discrete phases within a respiration cycle of the patient,
(ii) density filtering the respiratory-gated point cloud,
(iii) classifying the density filtered respiratory-gated point cloud according to anatomical points of reference in a segmented image dataset for the region of the patient's respiratory system,
(iv) registering the classified respiratory-gated point cloud to the segmented image dataset,
(v) comparing the classified respiratory-gated point cloud to a segmented image data set to determine the weighting of points comprised by the respiratory-gated point cloud,
(vi) distinguishing regions of greater weighting from regions of lesser weighting and optionally increasing the data set comprised by the respiratory-gated point cloud for regions of lesser weighting,
(vii) continuously modifying the registered segmented image dataset to correspond to the classified anatomical points of reference in the respiratory-gated point cloud to produce simulated real-time, intra-procedural images illustrating the orientation and shape of the anatomical features in the region of a patient's respiratory system, and
(viii) detecting center locations of selected imaged anatomical features by applying a centroid finding algorithm to selected points of the respiratory-gated point cloud.

8. The method of claim 7 wherein registering the respiratory-gated point cloud to the segmented image data set comprises:
registering the respiratory-gated point cloud representing at least one branch of the patient's respiratory system to corresponding anatomical points of reference in the registered segmented image data set representing the branch(es) of the patient's respiratory system.

9. The method of claim 7 wherein the respiratory-gated point cloud is registered to a plurality of branches of the patient's respiratory system, wherein the plurality of branches comprise the trachea, the right main bronchus, and the left main bronchus.

10. The method of claim 7 wherein the discrete phases are expiration, inspiration and discrete phases there-between.

11. The method of claim 7 wherein the segmented image dataset is from a first discrete phase of the patient's respiration cycle and the respiratory-gated point cloud is from a second and different discrete phase of the patient's respiration cycle.

12. A non-transitory processor-readable medium storing code representing instructions to cause a processor to perform a process, the code comprising code to carry out one or more elements of the method of claim 1.

13. A non-transitory processor-readable medium storing code representing instructions to cause a processor to perform a process, the code comprising code to carry out one or more elements of the method of claim 5.

14. A non-transitory processor-readable medium storing code representing instructions to cause a processor to perform a process, the code comprising code to carry out one or more elements of the method of claim 7.

* * * * *